(12) United States Patent
Burgey et al.

(10) Patent No.: US 6,387,911 B1
(45) Date of Patent: May 14, 2002

(54) PYRAZINONE THROMBIN INHIBITORS

(75) Inventors: Christopher Burgey, Philadelphia; Richard C. Isaacs, Harleysville; Bruce D. Dorsey, Maple Glen; Kyle A. Robinson, Elkins Park; Donnette Staas, Lansdale; Philip E. Sanderson, Philadelphia; James Barrow, Harleysville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 19 days.

(21) Appl. No.: 09/717,566

(22) Filed: Nov. 21, 2000

Related U.S. Application Data

(60) Provisional application No. 60/216,889, filed on Jul. 7, 2000, and provisional application No. 60/167,070, filed on Nov. 23, 1999.

(51) Int. Cl.$^7$ ................... A61K 31/497; C07D 401/12; C07D 401/14
(52) U.S. Cl. ................... 514/255.05; 544/405
(58) Field of Search ............... 544/405, 17; 514/255.05

(56) References Cited

U.S. PATENT DOCUMENTS

| | | |
|---|---|---|
| 5,260,307 A | 11/1993 | Ackermann et al. |
| 5,405,854 A | 4/1995 | Ackermann et al. |
| 5,455,348 A | 10/1995 | Austel et al. |
| 5,459,142 A | 10/1995 | Tone et al. |
| 5,510,369 A | 4/1996 | Lumma et al. |
| 5,744,486 A | 4/1998 | Sanderson et al. |
| 5,866,573 A | 2/1999 | Sanderson et al. |
| 5,981,546 A | 11/1999 | Duggan et al. |

FOREIGN PATENT DOCUMENTS

| | | |
|---|---|---|
| EP | 0262096 A1 | 3/1988 |
| EP | 0 509 769 A2 | 10/1992 |
| WO | WO 94/25051 | 11/1994 |
| WO | WO 96/11697 | 4/1996 |
| WO | WO 96/31504 | 10/1996 |
| WO | WO 96/32110 | 10/1996 |
| WO | WO 97/01338 | 1/1997 |
| WO | WO 97/40024 | 10/1997 |
| WO | WO 98/31670 | 7/1998 |
| WO | WO 98/42342 | 10/1998 |
| WO | WO 99/11267 | 3/1999 |
| WO | WO 99/59591 | 11/1999 |
| WO | WO 00/69834 | 11/2000 |

OTHER PUBLICATIONS

Peter R. Bernstein, et al., "Nonpeptidic Inhibitors of Human Leukocyte Elastase . . ." *J. Med. Chem.*, vol. 37, 1994, pp. 3313–3326.

Sanderson, et al., "Preparation of 3–amino–2–pyrazinone–1–acetamide derivatives as thrombin inhibitors," *Chem. Abstracts* (The Amer. Chem. Soc.), vol. 128, No. 3, pp. 532–533, 22922r, Jan. 19, 1998.

Kitazawa, et al., "Preparation of 1,4–disubstituted cyclic amino derivatives as serotonin antagonists," Database CA on Stn., *Chem Abs.*, vol. 129: 302552 (1998).

Semple et al., "Design, synthesis, and evolution of a novel, selective, and orally bioavailable class of thrombin inhibitors: . . .", *J. Med. Chem.*, vol. 39, pp. 4531–4536 (1996).

Sanderson, et al., "An efficacious, orally bioavailable, pyridinone acetamide thrombin inhibitor", *Bioorganic Medicinal Chemistry Letters*, vol. 8, pp. 817–822, (1998).

*Primary Examiner*—Emily Bernhardt
(74) *Attorney, Agent, or Firm*—Richard S. Parr; Melvin Winokur

(57) ABSTRACT

Compounds of the invention are useful in inhibiting thrombin and associated thrombotic occlusions having the following structure:

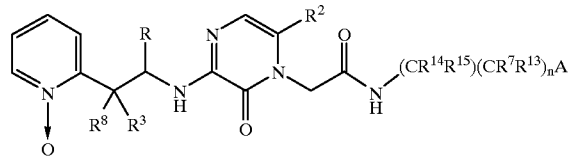

or a pharmaceutically acceptable salt thereof, wherein A is

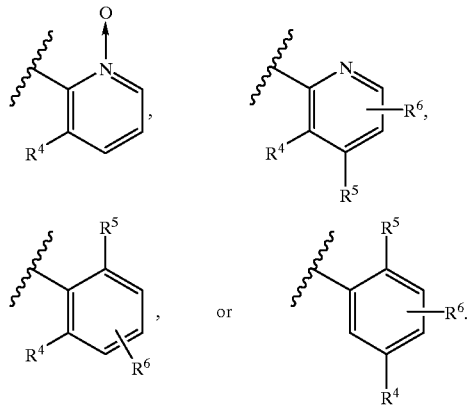

14 Claims, No Drawings

PYRAZINONE THROMBIN INHIBITORS

CROSS-REFERENCE TO RELATED APPLICATIONS

This application claims the benefit of U.S. Provisional Application No. 60/167,070, filed Nov. 23, 1999, and U.S. Provisional Application No. 60/216,889, filed Jul. 7, 2000.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., J. Med. Chem., Vol. 37, pages 1259–1261 (1994) describes orally active, non-peptidic inhibitors of human leukocyte elastase which contain trifluoromethylketone and pyridinone moieties.

H. Mack et al., J. Enzyme Inhibition, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

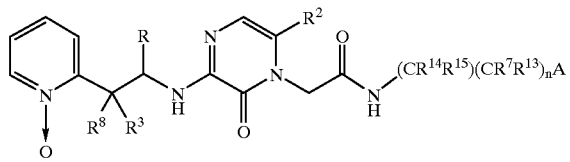

wherein
A is

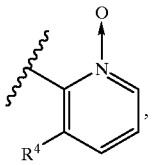 , 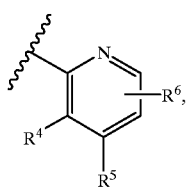

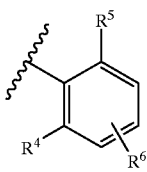 , or 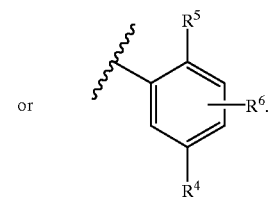

$n=0-1$;

R is
  hydrogen,
  $C_{1-4}$ alkyl unsubstituted or substituted with halogen, $OR^9$, $N(R^9)_2$, $COOR^9$; $CON(R^9)_2$ aryl, or a heterocyclic ring, wherein $R^9$ is independently hydrogen or $C_{1-4}$ alkyl;

$R^2$ is
  hydrogen,
  $C_{1-4}$ alkyl,
  $CF_3$,
  halogen,
  cyano, or
  cyclo $C_{3-7}$ alkyl;

$R^3$, $R^7$, $R^8$, and $R^{13}$ are independently chosen from
  hydrogen,
  halogen,
  $C_{1-4}$ alkyl;

$R^{14}$ and $R^{15}$ are independently chosen from
  hydrogen,
  $C_{1-2}$ alkyl, and
  $C_{1-2}$ alkyl substituted with $OR^{16}$ or $COOR^{16}$, wherein $R^{16}$ is hydrogen or $C_{1-4}$ alkyl; and $R^4$, $R^5$ and $R^6$ are independently chosen from
  hydrogen,
  halogen,
  hydroxy,
  $C_{1-4}$ alkyl,
  $C_{1-4}$ alkoxy,
  cyano,
  $CF_3O$,
  $CHF_2O$,
  $CF_3CH_2O$,
  $SR^{10}$,
  $SOR^{10}$, SO$_2$R$^{10}$,
OR$^{11}$,
SR$^{11}$,
NHR$^{11}$
  wherein
    R$^{10}$ is C$_{1-4}$ alkyl unsubstituted or substituted with C(CH$_3$)$_2$NH$_2$, C(CH$_3$)$_2$OH, C(CH$_3$)$_2$NHCOCF$_3$, or CF$_3$, and
    R$^{11}$ is phenyl unsubstituted or substituted with one or more of C$_{1-4}$ alkyl, C$_{1-4}$ alkoxy, halogen, hydroxy, COOH, CONH$_2$, CH$_2$OH, or CO$_2$R$^{12}$, wherein R$^{12}$ is C$_{1-4}$ alkyl.

Note that methyl substituents are conventionally indicated as bonds attached to an atom, Me, or CH$_3$.

In a class of compounds, A is

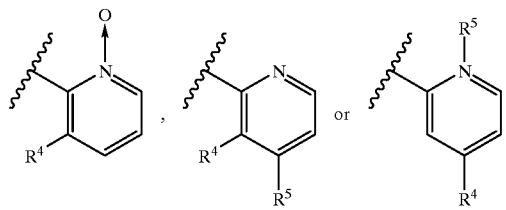

In a subclass of the class of compounds, R$^2$ is Cl, CH$_3$ or CN; R$^4$ and R$^5$ are independently selected from the group consisting of hydrogen, C$_{1-4}$ alkyl, SMe, SOMe, SO$_2$Me, CN, OCH$_2$CF$_3$, OCH$_3$ SCH$_2$C(CH$_3$)$_2$NH$_2$, OCF$_3$, SCH$_2$CH$_3$, SOCH$_2$CH$_3$, SO$_2$CH$_2$CH$_3$, SCH$_2$CF$_3$, SOCH$_2$CF$_3$, SO$_2$CH$_2$CF$_3$, and halogen R$^7$ is hydrogen or fluoro; and R$^{13}$ is hydrogen or fluoro.

In a family of the subclass of compounds, R$^4$ and R$^5$ are independently selected from the group consisting of hydrogen, CH$_3$, Cl, F, SMe, SOMe, SO$_2$Me, CN, OCH$_2$CF$_3$, OCH$_3$, SCH$_2$C(CH$_3$)$_2$NH$_2$, OCF$_3$, SCH$_2$CH$_3$, SOCH$_2$CH$_3$SCH$_2$CF$_3$, SOCH$_2$CF$_3$, and SO$_2$CH$_2$CF$_3$.

In a first subfamily of the family, A is selected from the group consisting of

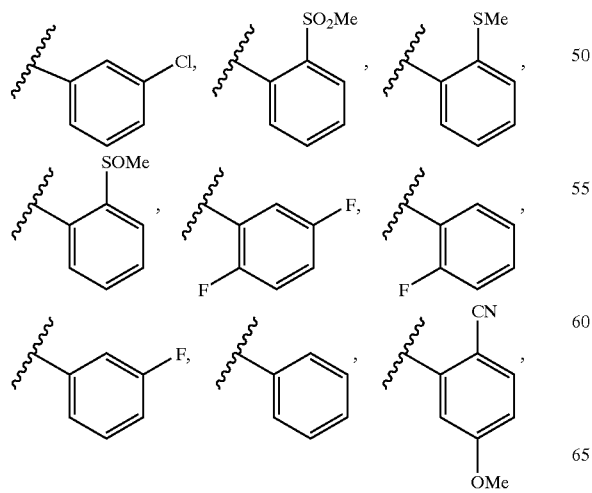

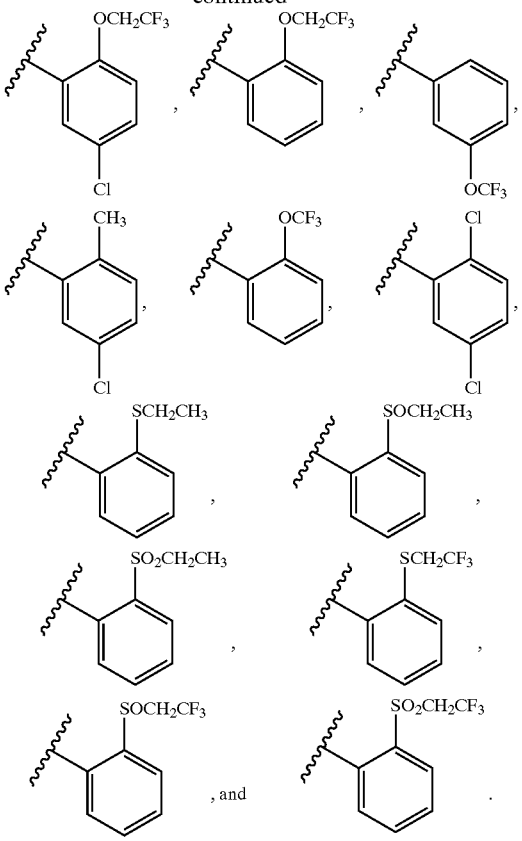

In a second subfamily of the family, A is selected from the group consisting of

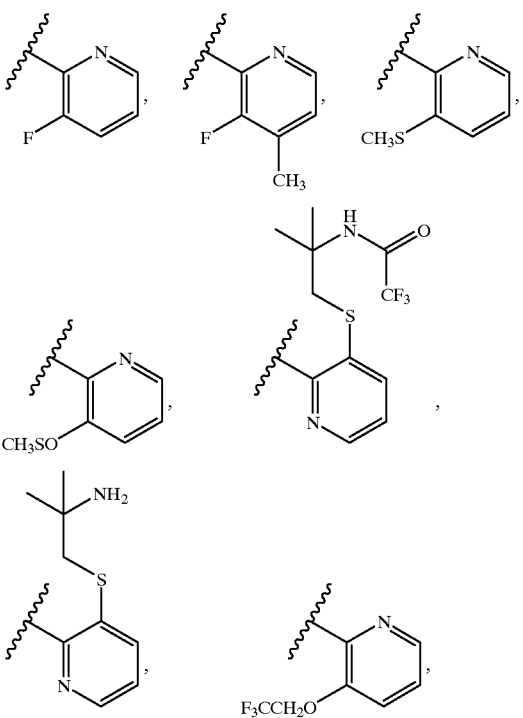

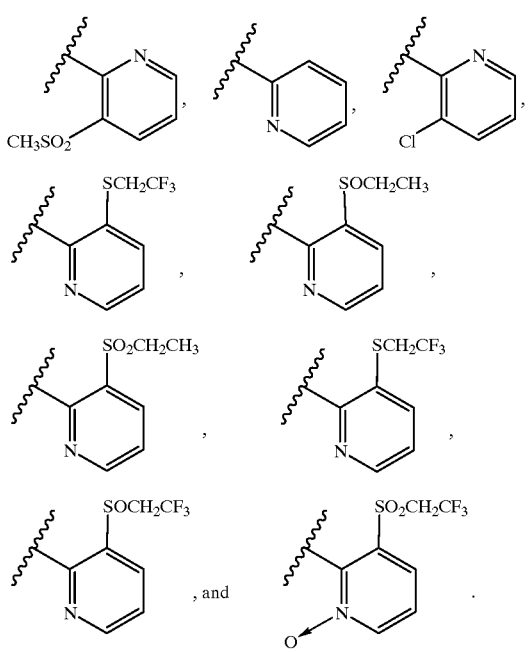
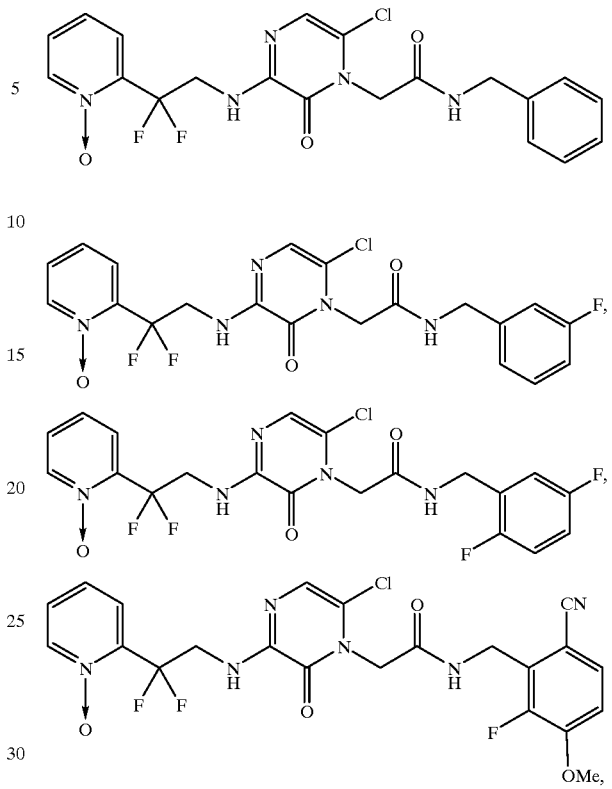
In a collection of the first subfamily, the compound is selected from the group consisting of
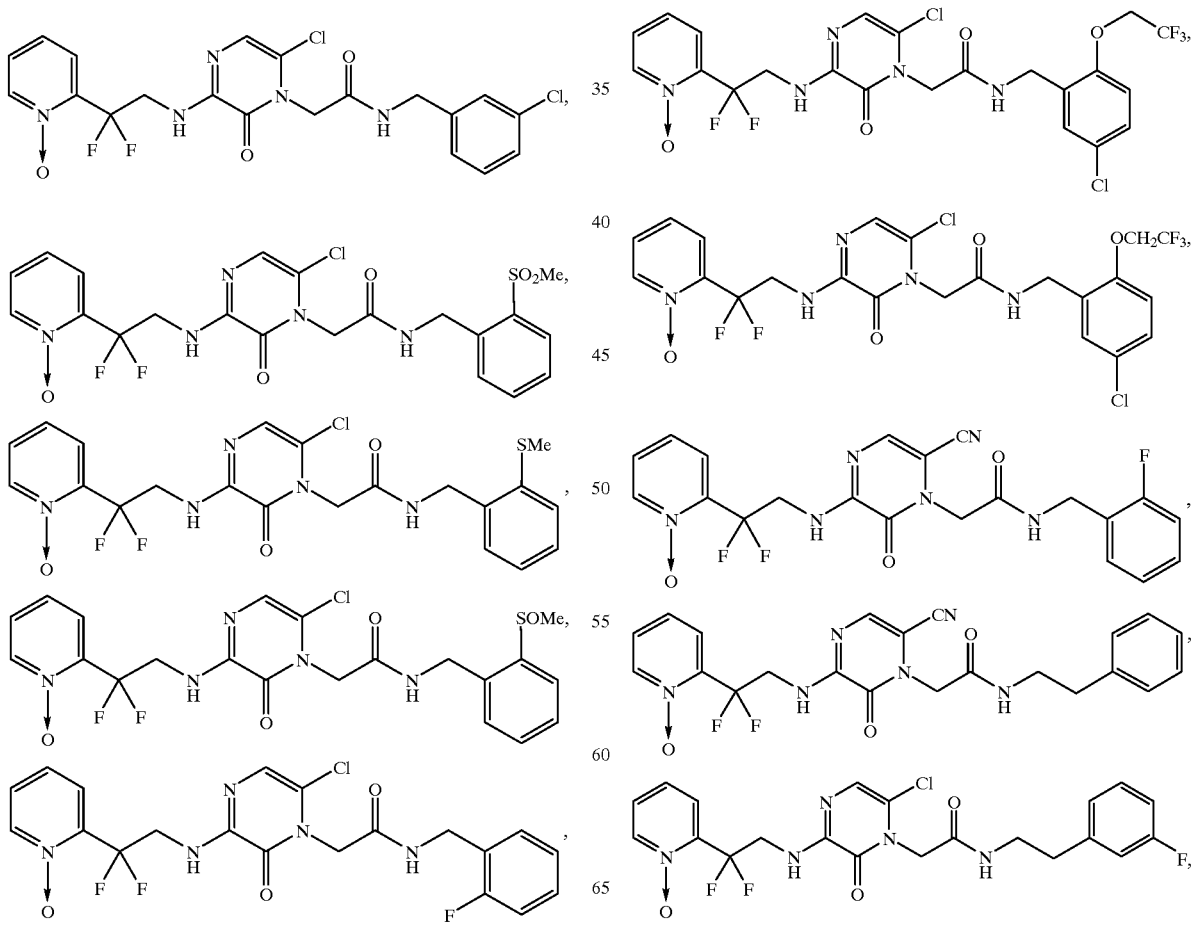

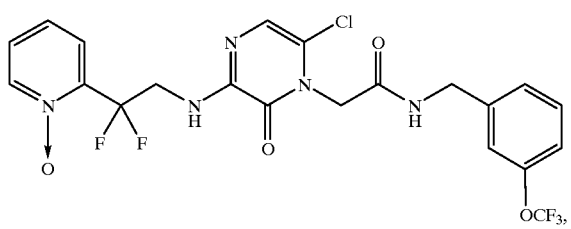
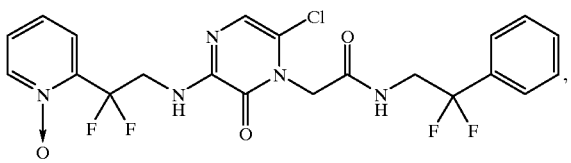
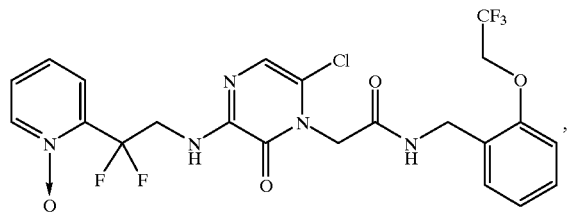
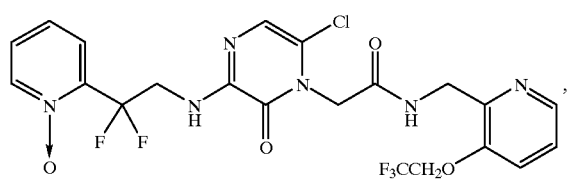
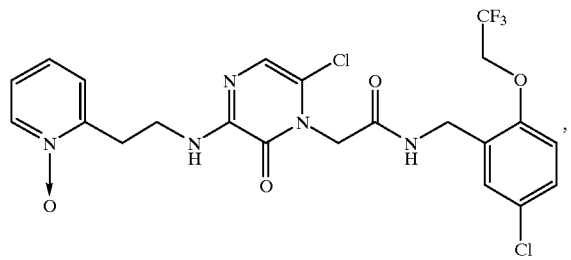
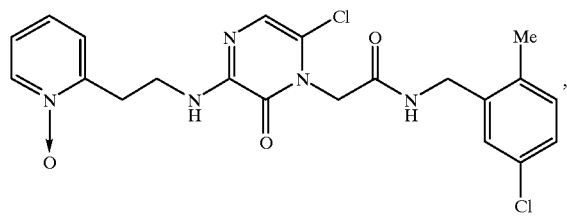
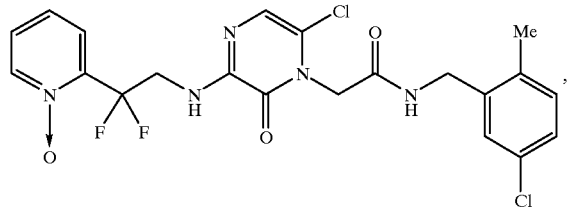
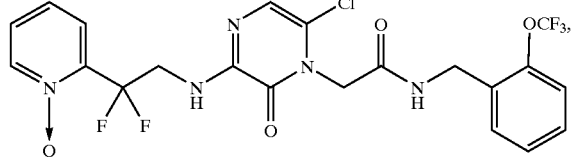
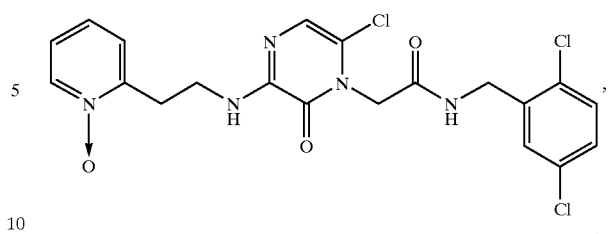
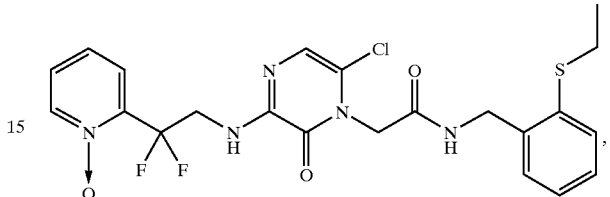
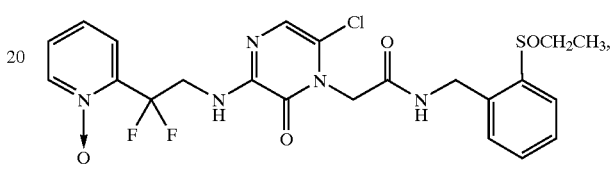
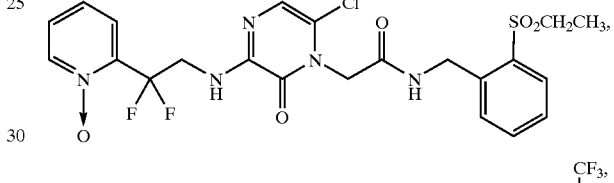
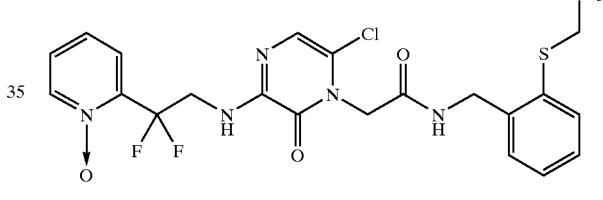
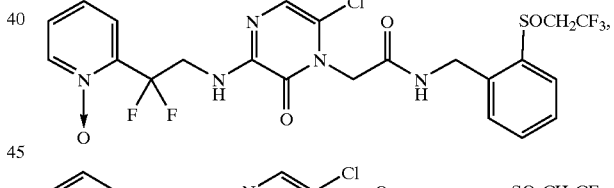
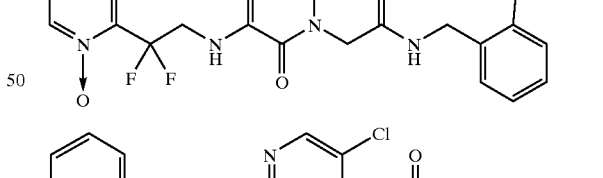
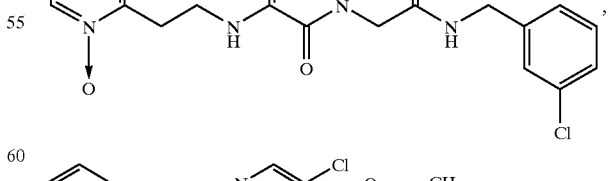
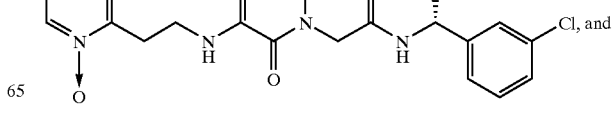

-continued
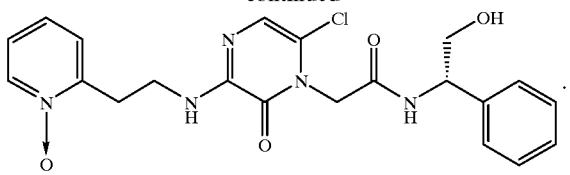
Examples of this collection include
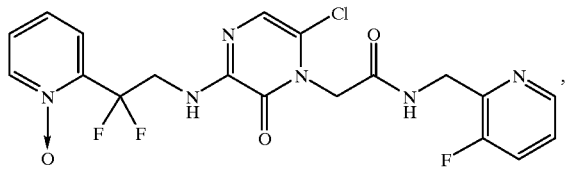
and
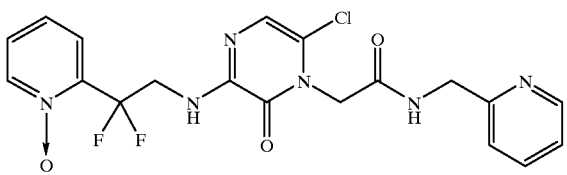
and pharmaceutically acceptable salts thereof.
In a collection of the second subfamily, the compound is selected from the group consisting of
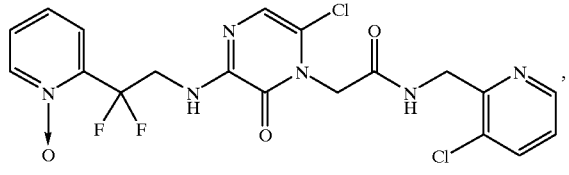
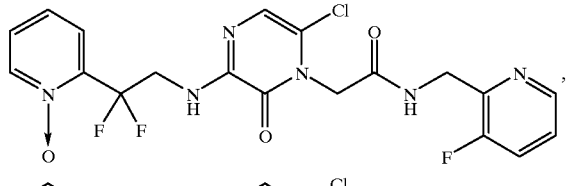
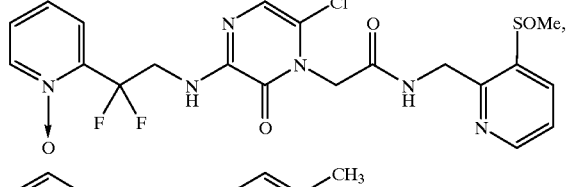
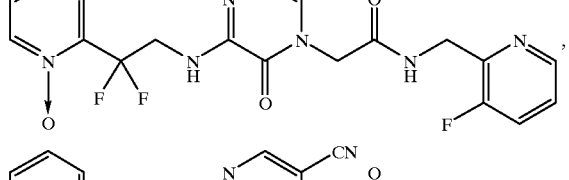
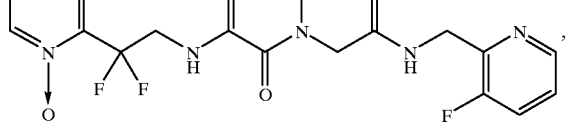
-continued
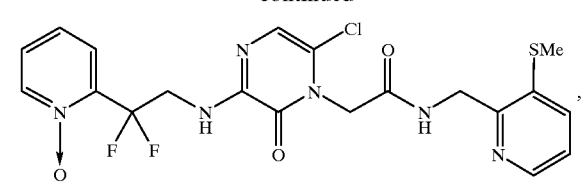
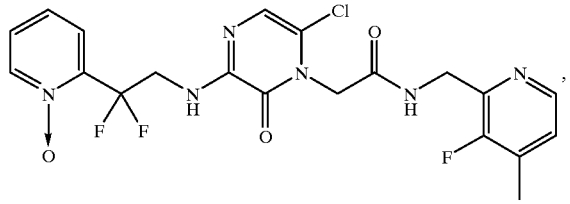
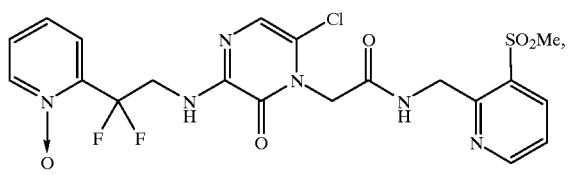
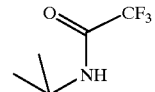
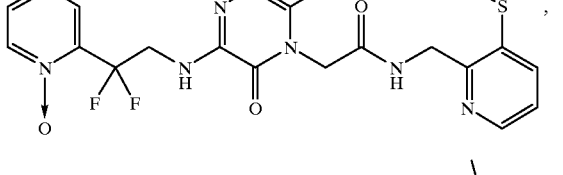
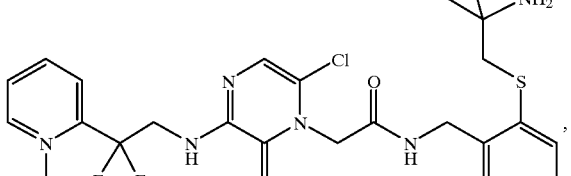
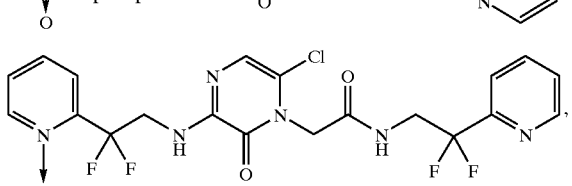
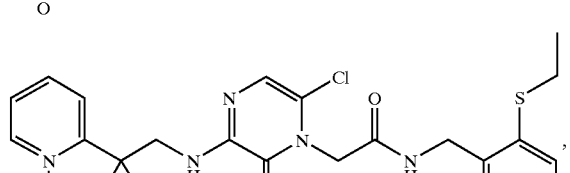
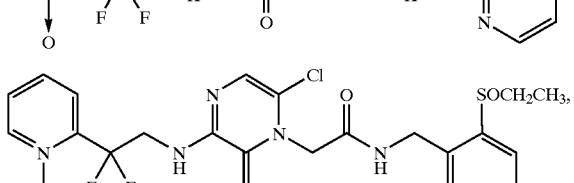

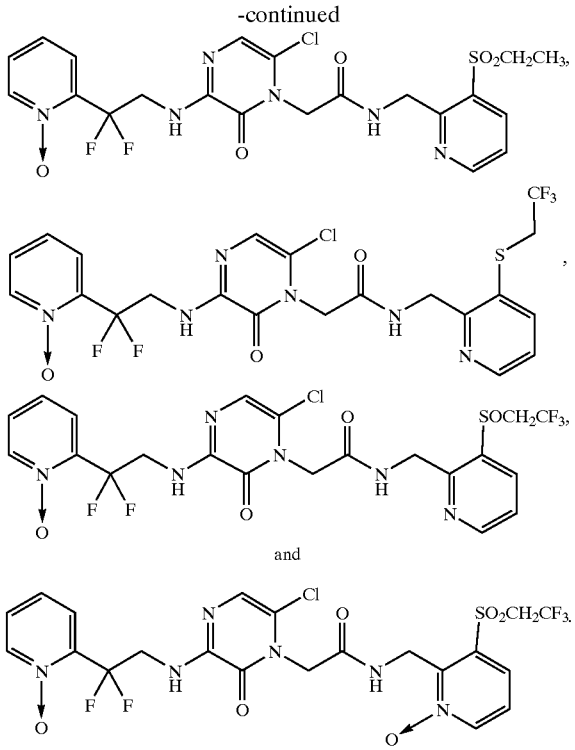

Examples of this collection include

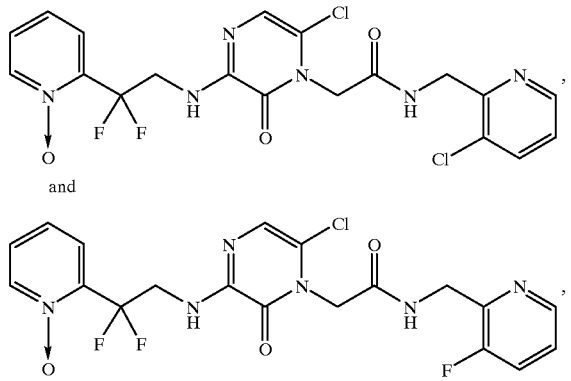

and pharmaceutically acceptable salts thereof.

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of Substituents and/or variables are permissible only if such combinations result in stable compounds.

Some abbreviations that may appear in this application are as follows:

ABBREVIATIONS

| Designation | |
|---|---|
| $BH_3$ | borane |
| $CH_3CH_2OTf$ | ethyl triflate |
| $Cs_2CO_3$ | cesium carbonate |
| DAST | diethylaminosulfurtrifluoride |
| DBU | 1,8-diazabicyclo[5.4.0]undec-7-ene |
| DCE | 1,2-dichloroethane |
| DMAP | dimethylaminopyridine |
| DMF | dimethylformamide |
| DPPA | diphenylphosphoryl azide |
| EDC | 1-ethyl-3-(3 dimethylaminopropyl)carbodiimide hydrochloride |
| EtOH | ethanol |
| $Et_3N$ (TEA) | triethylamine |
| HCl | hydrochloric acid |
| HOAc | acetic acid |
| HOAT | 1-hydroxy-7-azabenzotriazole |
| iPrOH | isopropyl alcohol |
| KOH | potassium hydroxide |
| $K_2CO_3$ | potassium carbonate |
| LAH | lithium aluminum hydride |
| LDA | lithium diisopropylamide |
| $LiAlH_4$ | lithium aluminum hydride |
| MCPBA | meta-chloroperbenzoic acid |
| MeI | iodomethane |
| MeOH | methanol |
| $NaBH_4$ | sodium borohydride |
| $NaN_3$ | sodium azide |
| nBuLi | n-butyllithium |
| $NH_4OH$ | ammonium hydroxide |
| NCS | N-chlorosuccinimide |
| Pd-C | palladium on activated carbon catalyst |
| Pd(O) | palladium oxide |
| $PhB(OH)_2$ | phenylboronic acid |
| $POBr_3$ | phosphorous oxybromide |
| $PPh_3$ | triphenylphosphine |
| TBAF | tetrabutylammonium fluoride |
| TBSCl | tert-butyldimethylsilyl chloride |
| TFA | trifluoroacetic acid |
| $Tf_2O$ | trifluoromethanesulfonic anhydride |
| THF | tetrahydrofuran |
| TMSCN | trimethylsilyl cyanide |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "halogen", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "cyclo$C_{3-7}$alkyl" is intended to include cyclopropyl, cyclobutyl, cyclopentyl, cyclohexyl and cycloheptyl, and the like.

The term "aryl" as used herein except where noted, represents a stable 6- to 10-membered mono- or bicyclic ring system such as phenyl, or naphthyl. The aryl ring can be unsubstituted or substituted with one or more of $C_{1-4}$ lower alkyl; hydroxy; alkoxy; halogen; amino.

The pyridyl N-oxide portion of the compounds of the invention are structurally depicted using conventional representations

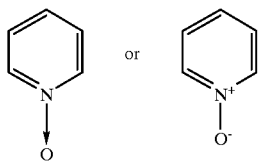

which have equivalent meanings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Coming Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Compounds having the general structure

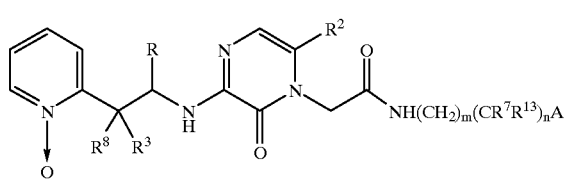

wherein, R, $R^2$, $R^3$ $R^7$, $R^8$, $R^{13}$, m and n have the above-described meanings and A is fluoropyridyl, can be prepared by reacting an acid such as

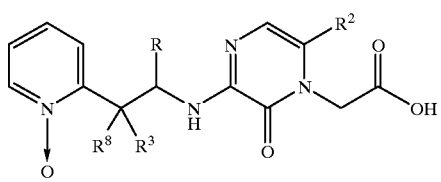

with an amine such as

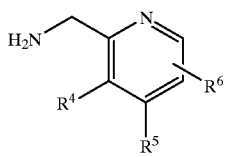

under conditions suitable for forming amide bond between the acid and the amine wherein $R^4$, $R^5$ and $R^6$ have the above described meanings. The title compounds may be prepared according to the following procedures described in Example I and illustrated in the scheme below. Bromopyridine (1) is reacted with n-BuLi to afford an anion intermediate which is reacted with diethyl oxalate (2) to afford ketoester (3). Ester 3 is reacted with diethylaminosulfurtrifluoride (DAST) to afford difluoride 4 and the ester is reduced with sodium borohydride in ethanol to give alcohol 5. The alcohol is converted to a triflate leaving group which is reacted with sodium azide to afford the azide 6. The pyridine is oxidized, and then the azide is reduced to give amine 7. The pyrazinone 14 is prepared by reacting ethylchlorooxalate 8 with ethyl glycinate 9 to afford 10 which is reacted with amine 11 to give compound 12. Compound 12 is cyclized with acid and reacted with phosphorous oxybromide to afford 14. Amine 7 is then reacted with pyrazinone 14 as shown to give the ester 15. The ring of 15 is chlorinated with n-chlorosuccinimide, and the ester group is hydrolyzed to afford acid 16 which is coupled to 3-fluoro-2-aminomethyl-pyridine to afford the final product 17.

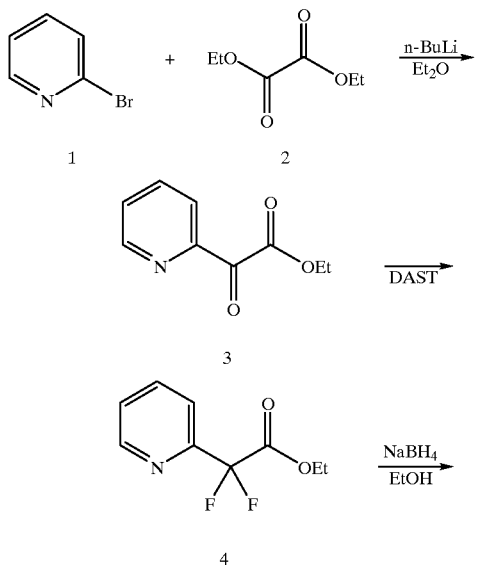

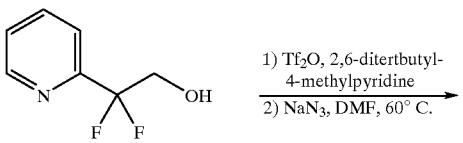

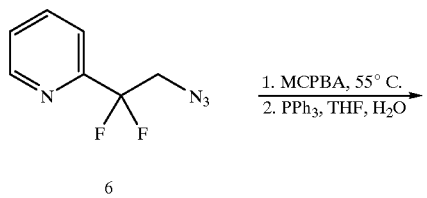

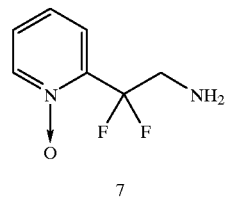

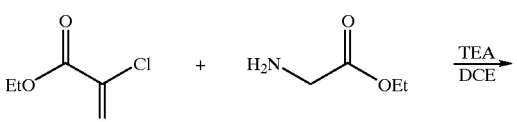

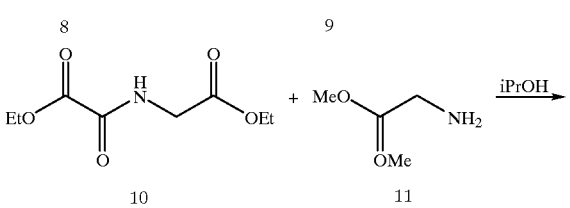

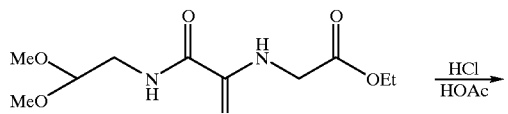

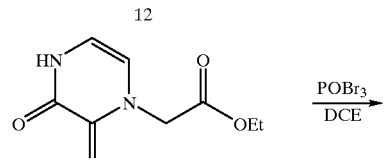

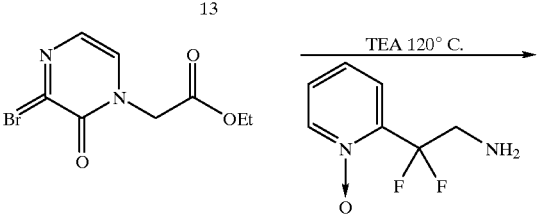

-continued

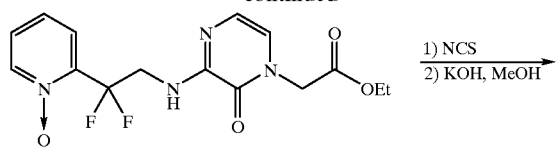 1) NCS
2) KOH, MeOH

15

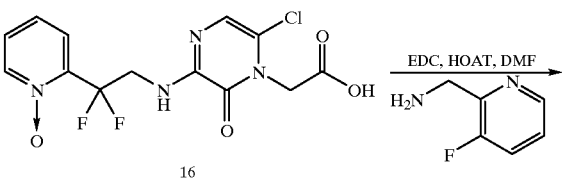 EDC, HOAT, DMF

16

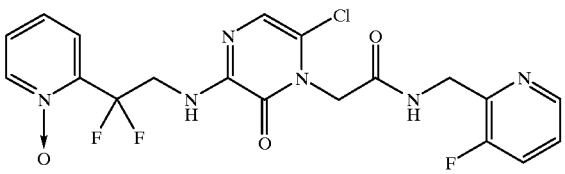

17

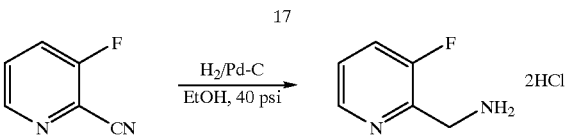 H₂/Pd-C
EtOH, 40 psi

Synthesis of 2-aminomethyl-3-fluoropyridine begins with catalytic reduction of 2-cyano-3-fluoropyridine (Sakamoto et al., Chem. Pharm. Bull. 33(2) 565–571 (1985)) using palladium on carbon which provides 2-aminomethyl-3-fluoropyridine B as the dihydrochloride salt.

Typically, solution phase amide couplings may be used to form the final product, but solid-phase synthesis by classical Merrifield techniques may be employed instead. The addition and removal of one or more protecting groups is also typical practice.

Compounds having different groups at variable A can be prepared by coupling alternative commercially available amino derivatives

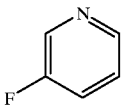

where $Y^1$ and $Y^2$ are defined above, using the coupling procedure described for coupling

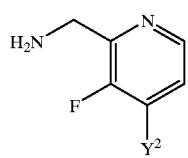

to the carboxylic acid. Alternative amino derivatives and methods for preparing amino derivatives are known to those skilled in the art and described below.

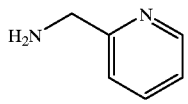

is commercially available.

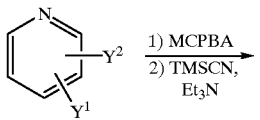 1) MCPBA
2) TMSCN, Et₃N 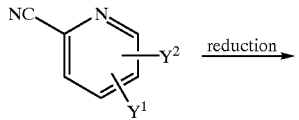 reduction

2)

for example

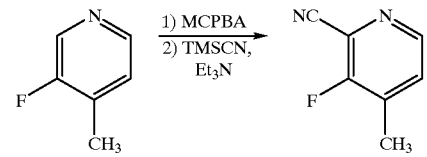 1) LDA, -78° C.
2) MeI, -78° C.

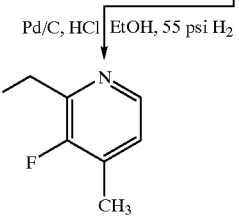 1) MCPBA
2) TMSCN, Et₃N

Pd/C, HCl | EtOH, 55 psi H₂ and also for example

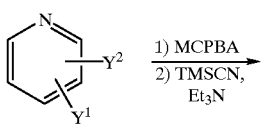 1) MCPBA
2) TMSCN, Et₃N 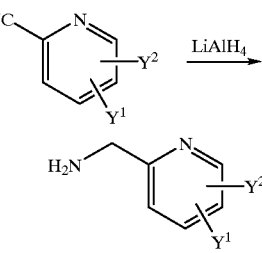 LiAlH₄

Unless otherwise stated, all NMR determinations were made using 400 MHz field strength.

EXAMPLE 1

Preparation of 3-Fluoro-2-pyridylmethyl 3-(2,2-difluoro-2-(2-pyridyl-N-oxide)ethylamino)-6-chloropyrazin-2-one-1-acetamide (17)

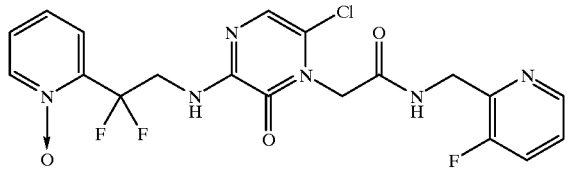

Step A
2-Aminomethyl-3-fluoropyridine (B) as a dihydrochloride salt

A stirred solution of 6.11 g (50.1 mmol) of 2-cyano-3-fluoropyridine in 250 mL of ethanol and 12.5 mL (150 mmol) of conc. HCl was hydrogenated over 1.90 g of 10% palladium on carbon at 40 psi for 16 h. The catalyst was removed by filtration and the solvents removed at reduced pressure. The resulting solid was diluted with acetonitrile and filtered to give the title compound as an off-white solid: $^1$H NMR (CD$_3$OD) δ8.48 (d, 1H, 4.8 Hz), 7.69 (td,1H, 9.2, 1.1 Hz), 7.68 (ddd, 1H, 8.8, 4.4, 4.4 Hz), 4.34 (s, 2H).

Step B
Ethyl 2-pyridinoylformate (3)

To a stirred solution of 20 mL (210 mmol) of 2-bromopyridine in 500 mL of dry ether at −78° C. under Ar was added 85 mL of a 2.5 M solution of n-butyllithium in hexane in a slow stream. After stirring in the cold for 30 min, the solution was transferred over a 5 min period via two cannula into a 0° C. stirred solution of 100 mL (736 mmol) of diethyl oxalate in 1.0 L of dry ether under Ar. After stirring for 2h in the cold, the reaction mixture was washed with 600 mL of sat. NaHCO$_3$, water, and brine. The solution was dried over MgSO$_4$ and the solvents concentrated at reduced pressure to give a red oil that was purified by SiO$_2$ chromatography (10×15 cm) using 1:4 to 35:65 EtOAc-hexanes. The product-containing fractions were concentrated at reduced pressure to afford 3 as a reddish oil: $^1$H NMR (CDCl$_3$) δ1.42 (t, 3H), 4.45–4.55 (m, 2H), 7.55–7.6 (m, 1H), 7.9–7.95 (m, 1H), 8.11 (d, 1H), 8.78 (d, 1H).

Step C
Ethyl difluoro-2-pyridylacetate (4)

A stirred solution of 22 g (123 mmol) of ethyl 2-pyridinoylformate 3 and 75 g (465 mmol) of diethylaminosulfurtrifluoride (DAST) were heated to 55° C. under Ar overnight. Because the reaction was not complete, 5 g additional DAST was added, and the reaction heated for an additional 24 h. The reaction mixture was cooled to rt, and poured very slowly into a stirred mixture of 1 kg of ice, 400 mL of ethyl acetate and 500 mL of sat. NaHCO$_3$. After the addition, the mixture was basified by the addition of solid NaHCO$_3$. The aqueous layer was extracted with EtOAc, and the combined organic layers washed with sat. NaHCO$_3$, brine, dried over Na$_2$SO$_4$ and the solvents concentrated at reduced pressure to give 4 as a brown oil: $^1$H NMR (CDCl$_3$) δ1.35 (t, 3H), 4.35–4.4 (m, 2H), 7.4–7.45 (m, 1H), 7.75 (d, 1H), 7.95 (d, 1H), 8.45 (d, 1H).

Step D
2,2-Difluoro-2-(2-pyridyl)ethanol (5)

To a stirred solution of 19.5 g (97 mmol) of ethyl difluoro-2-pyridylacetate 4 in 200 mL of absolute ethanol at 0° C. was added 4.42 g (1 16 mmol) of sodium borohydride in small portions. After 30 min, the reaction was quenched by the addition of 50 mL of sat. NH$_4$Cl. The reaction mixture was concentrated at reduced pressure and the residue partitioned between 500 mL of ethyl acetate and sat. NaHCO$_3$. The organic layer was washed with water, brine, and dried over Na$_2$SO$_4$ and concentrated at reduced pressure to give a brown oil that was purified on SiO, (10×17 cm) using 1:1 EtOAc-hexane. After re-chromatographing the mixed fractions, all clean fractions were combined and concentrated at reduced pressure, giving 5 as a beige crystalline solid: $^1$H NMR (CDCl$_3$) δ3.6 (t, 1H), 4.17–4.3 (m, 2H), 7.4–7.45 (m, 1H), 7.73 (d, 1H), 7.84–7.91 (m, 1H), 8.61 (d, 1H).

Step E
2,2-Difluoro-2-(2-pyridyl)ethyl trifluoromethanesulfonate (5a)

To a stirred solution of 5 g (31.4 mmol) of 2,2-difluoro-2-(2-pyridyl)ethanol 5 and 9.69 g (47.2 mmol) of 2,6-di-t-butyl-4-methylpyridine in 110 mL of methylene chloride at −78° C. under Ar was added 7.93 mL (47.2 mmol) of triflic anhydride dropwise. After 1 h, the reaction was diluted with 100 mL of pentane and filtered. The filtrate was concentrated and treated again with pentane and filtered. Concentration of the filtrate gave 5a as a brown oil, contaminated with 2,6-di-t-butyl-4-methylpyridine: $^1$H NMR (CDCl$_3$) δ5.12 (t, 2H), 7.45–7.5 (m, 1H), 7.75 (d, 1H), 7.86–7.94 (m, 1H), 8.65 (d, 1H).

Step F
2,2-Difluoro-2-(2-pyridyl)ethylazide (6)

To a stirred solution of 5.5 g of 2,2-difluoro-2-(2-pyridyl)ethyl trifluoromethanesulfonate 5a in 70 mL of DMF was added 6.74 g (104 mmol) of sodium azide under Ar. The mixture was heated to 60° C. overnight. A second batch was run in the same manner, and after cooling to rt, both reactions were poured into 600 mL of water, and extracted with 3×500 mL of ether. The combined extracts were washed with brine, dried over Na$_2$SO$_4$ and concentrated at reduced pressure to give an oil that was purified by SiO$_2$ (10×6 cm) using hexane 1:3 EtOAc-hexane and 1:1 EtOAc-hexane. The product-containing fractions were concentrated at reduced pressure to give 6 as a yellow oil: $^1$H NMR (CDCl$_3$) δ4.05 (t, 2H), 7.4–7.45 (m, 1H), 7.73 (d, 1H), 7.83–7.89 (m, 1H), 8.67 (d, 1H).

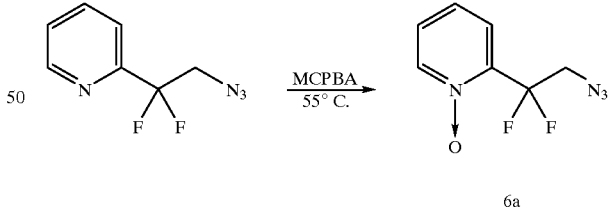

6a

Step G
2,2-Difluoro-2-(2-pyridyl-N-oxide)ethylazide (6a).

To a stirred solution of 2,2-difluoro-2-(2-pyridyl-N-oxide)ethylazide (5.75 g, 31.3 mmol ) in 1,2-dichloroethane (100 mL) was added 3-chloroperoxybenzoic acid (10.26 g, 41.6 mmol) and 3-tert-butyl-4-hydroxy-5-methylphenyl sulfide (1.12 g, 3.13 mmol) under Ar. The mixture was heated at 55° C. overnight. In the morning, the solution was poured into a sat. aq. NaHCO$_3$/Na$_2$S$_2$O$_3$ solution (200 mL). The layers were separated and the aqueous phase was back-washed with dichloromethane (3×150 mL). The combined organic layers were dried over MgSO$_4$, concentrated and chromatographed on a short SiO2 column using 100% EtOAc to give the title compound as a white solid: $^1$H NMR (CDCl$_3$) δ4.38 (t, 2H, 13.5 Hz), 7.36–7.44 (m, 2H), 7.72 (dd, 1H, 2.3 Hz, 7.6 Hz), 8.26 (d, 1H, 6.1 Hz).

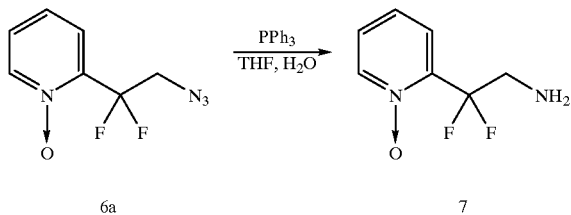

6a 7

Step H
2,2-Difluoro-2-(2-pyridyl-N-oxide)ethylamine (7)

Triphenylphosphine (7.72 g, 29.5 mmol) was added to a water bath cooled solution of 2,2-difluoro-2-(2-pyridyl-N-oxide)ethylazide (5.61 g, 28.1 mmol) in THF (90 mL). After 1 h water (10 mL) was added and the mixture was heated to 55° C. Two hours after the addition of water, the heating bath was removed and the solution was allowed to stir overnight. The reaction was subsequently concentrated, diluted with EtOAc (250 mL), and HCl (25 mL, 2.6M in EtOAc) was added dropwise. Stirring was continued for 20 min, after which time the mixture was filtered and rinsed with EtOAc (150 mL). To a stirred suspension of this solid in dichloromethane (300 mL) was added NaOH (3.33 g in 15 mL H$_2$O) dropwise. After 15 min the mixture was poured into a separatory funnel and the organic phase was separated. The aqueous phase was saturated with solid NaCl and extracted with CH$_2$Cl$_2$ (3×100 mL). The combined organic extracts were dried over Na$_2$SO$_4$ and concentrated to an oil which solidified upon storage in the freezer (white solid): $^1$H NMR (CDCl$_3$) δ8.25 (br d, 1H, 6.2 Hz), 7.69 (dd, 1H, 2.8, 7.3 Hz), 7.32–7.39 (m, 2H), 3.76 (t, 2H, 15.2 Hz), 1.29 (br s, 2H).

Step I
Ethyl N-(ethyl carboxymethyl)oxamate (10)

To a suspension of ethyl glycine.HCl (38.4 g, 275 mmol) in 1,2-dichloroethane (360 mL) was added triethylamine (77.0 mL, 550 mmol) at room temperature. After stirring for 30 minutes the heterogenous mixture was cooled to 0° C. and ethyl oxalyl chloride (30.3 mL, 275 mol) was added dropwise over the course of 1 h. Upon completion of the addition, the cooling bath was removed and the reaction was stirred at room temperature overnight. The reaction was diluted with water (250 mL) and the layers separated. The aqueous layer was backwashed with 2 portions of dichloromethane (250 mL). The combined organic layers were washed with water (250 mL), followed by brine (250 mL), dried over MgSO$_4$ and concentrated to give an oil 10 that was taken directly onto the next step.

Step J
N-(Ethyl carboxymethyl)-N'-(2,2-dimethoxyethyl)oxamide (12)

To a solution of the oxamate (84.0 g, 414 mmol) 10 in 2-propanol (500 mL) was added aminoacetaldehyde dimethyl acetal (45.7 g, 435 mmol) in one portion. After stirring overnight at room temperature, the reaction mixture was concentrated to a thick orange oil. This thick slurry was diluted with 2-propanol (300 mL) and the solid was broken up with a spatula. Filtration afforded a solid which was further rinsed with an additional portion of 2-propanol. Removal of residual 2-propanol was accomplished via high vacuum to afford a light orange solid 12: $^1$H NMR (CDCl$_3$) δ7.82 (br s, 1H), 7.50 (br s, 1H), 4.41 (t, 1H, 5.3 Hz), 4.24 (q, 2H, 7.1 Hz), 4.09 (d, 2H, 5.9 Hz), 3.47 (dd, 2H, 5.3, 6.2 Hz), 3.40 (s, 6H), 1.30 (t, 3H, 7.1 Hz).

Step K
Ethyl 3-hydroxypyrazin(1H)-2-one-1-acetate (13)

A solution of the oxamide (89.8 g, 343 mmol) 12, acetic acid (400 mL), and conc. HCl (2 mL) was heated to reflux. After 1 h the black reaction was concentrated to a thick oil (high vacuum employed to ensure complete removal of AcOH) which was diluted with EtOH (150 mL) and MeOH (150 mL). Scraping the thick black oil with a spatula induced precipitation of the product. The MeOH was removed via rotary evaporation and the remaining slurry was filtered and rinsed with EtOH (200 mL) to deliver a tan solid. Recrystallization from refluxing EtOH (300 mL) afforded an off-white powder 13: $^1$H NMR (CD$_3$OD) δ6.50 (d, 1H, 5.9 Hz), 6.36 (d, 1H, 5.9 Hz), 4.58 (s, 2H), 4.23 (q, 2H, 7.1 Hz), 1.28 (t, 3H, 7.1 Hz). Further crude dione could be obtained upon concentration of the mother liquor.

Step L
Ethyl 3-bromopyrazin(1H)-2-one-1-acetate (14)

A solution of the hydroxypyrazinone (25.0 g, 126 mmol) 2–3 and phosphorous oxybromide (37.9 132 mmol) in 1,2-dichloroethane (250 mL) was heated to reflux. After 8 h the reaction mixture was treated with sat. aq. Na$_2$CO$_3$ (250 ml) and stirred for 1 h. The mixture was diluted with water. (100 mL) and dichloromethane (100 mL), the layers were separated and the aqueous layer was backwashed with EtOAc (3×200 mL). The combined organics were dried (MgSO$_4$), and concentrated to give an oil which was stored on a high vacuum line overnite to afford brown solid 2–4: $^1$H NMR (CDCl$_3$) δ7.17 (d, 1H, 4.2 Hz), 7.07 (d, 1H, 4.2 Hz), 4.65 (s, 2H), 4.27 (q, 2H, 7.2 Hz), 1.31 (t, 3H, 7.2 Hz).

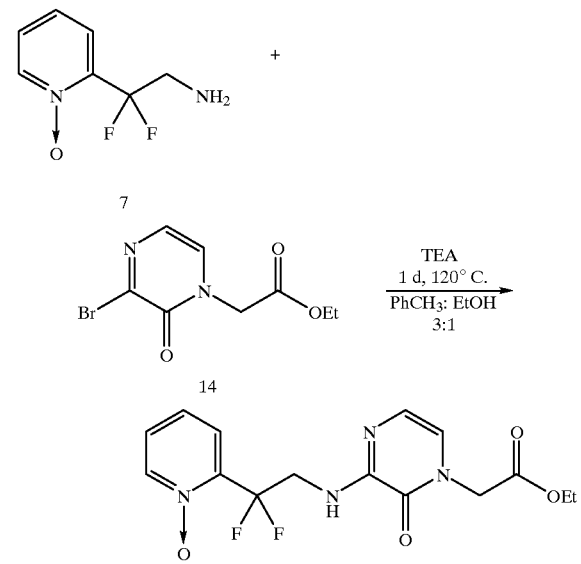

Step M
Ethyl 3-(2,2-difluoro-2-(2-pyridyl-N-oxide-ethylamino) pyrazin(1H)-2-one-1-acetate (15)

A mixture of 3.0 g (17.2 mmol) of 2,2-difluoro-2-(2-pyridyl-N-oxide)ethylamine, 2.72 mL (19.5 mmol) of triethylamine and 4.5 g(17.2 mmol) of ethyl 3-bromopyrazin (1H)-2-one-1-acetate in 9 mL of toluene and 3 mL of ethanol was heated to 120° C. in a sealed tube for 24 h. The reaction was concentrated and the residue was partitioned between EtOAc (200 mL) and sat. aq. NaHCO$_3$ (200 mL). The aqueous layer was backwashed with EtOAc (5×150 mL). The combined organic layers were dried over MgSO₄ and the solvents removed at reduced pressure to give a brown solid. This crude material was diluted with EtOAc (50 mL), filtered, and rinsed with EtOAc (2×50 mL) to afford the title compound as a tan powder: ¹H NMR (CDCl₃) δ8.26 (d, 1H, 6.4 Hz), 7.61 (br d, 1H, 7.9 Hz), 7.34 (dd, 1H, 6.6, 6.6 Hz), 7.26 (dd, 1H), 6.78 (d, 1H, 4.6 Hz), 6.39 (br t, 1H, 6.6 Hz), 6.37 (d, 1H, 4.6 Hz), 4.66 (td, 2H, 13.8, 7.0 Hz), 4.52 (s, 2H), 4.23 (q, 2H, 7.1 Hz), 1.28 (t, 3H, 7.1 Hz).

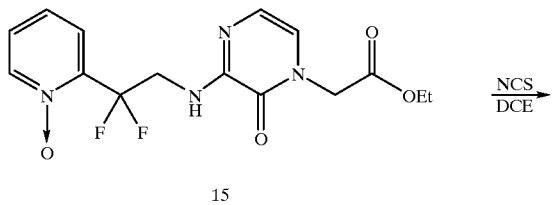

15

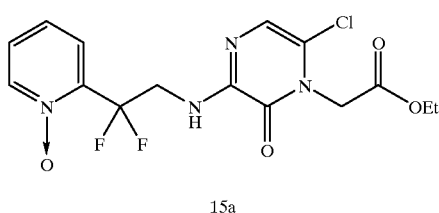

15a

Step N

Ethyl 3-(2,2-difluoro-2-(2-pyridyl-N-oxide-ethylamino)-6-chloropyrazin(1H)-2-one-1-acetate (15a)

A stirred solution of 4.96 g (14.0 mmol) of ethyl 3-(2,2-difluoro-2-(2-pyridyl-N-oxide-ethylamino)pyrazin(1H)-2-one-1-acetate and 1.86 g (14.0 mmol) of N-chlorosuccinimide in 200 mL of 1,2-dichloroethane was heated to 70° C. After 3 h the solution was cooled to room temperature and partitioned between dichloromethane (150 mL) and sat. aq. NaHCO₃ (200 mL). The layers were separated and the aqueous phase was backwashed with dichloromethane (4×200 mL) and EtOAc (2×200 mL). The combined organic layers were dried over NaSO₄ and the solution concentrated. This crude solid was purified on a SiO₂ column with 100% EtOAc to 10:90 MeOH:EtOAc to give the title compound as a white solid: ¹H NMR (CDCl₃) δ8.26 (d, 1H, 6.4 Hz), 7.62 (dd, 1H, 2.2, 7.9 Hz), 7.35 (ddd, 1H, 2.1, 7.7, 7.7 Hz), 7.2 (dd, 1H, 7.7 Hz), 6.86 (s, 1H), 6.35 (br t, 1H, 6.7 Hz), 4.85 (s, 2H), 4.64 (td, 2H, 13.8,6.9 H7), 4.24 (q, 2H, 7.1 Hz), 1.29 (t, 3H, 7.1 Hz).

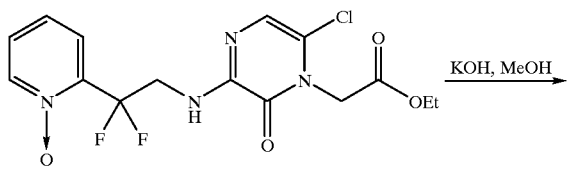

15a

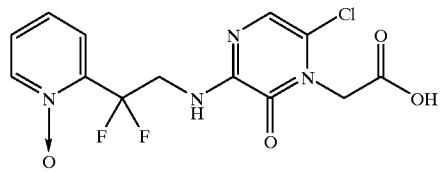

16

Step O
3-(2,2-Difluoro-2-(2-pyridyl-N-oxide-ethylamino)-6-chloropyrazin(1H)-2-one-1-acetic acid (16)

To a stirred solution of 4.88 g (12.6 mmol) of ethyl 3-(2,2-difluoro-2-(2-pyridyl-N-oxide-ethylamino)-6-chloropyrazin(1H)-2-one-1-acetate in methanol (100 mL) was added 5.0 g potassium hydroxide (89.1 mmol dissolved in 20 mL water). After 1 h the solution was concentrated, diluted with 50 mL of water and acidified to pH=7 using conc. HCl. Concentration at reduced pressure (azeotrope with PhCH₃) afforded an off-white solid containing potassium chloride and the title compound: ¹H NMR (CD₃OD) δ8.36 (d, 1H, 6.2 Hz), 7.69 (dd, 1H, 7.7, 2.2 Hz), 7.51–7.59 (m, 2H), 6.67 (s, 1H), 4.62 (s, 2H), 4.55 (t, 2H, 13.1 Hz).

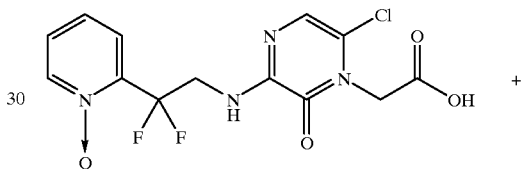

16

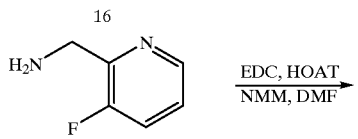

B

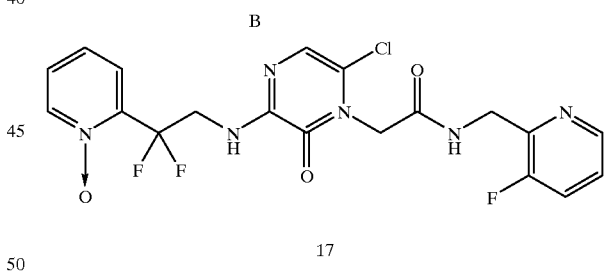

17

Step R
3-Fluoro-2-pyridylmethyl 3-(2,2-difluoro-2-(2-pyridyl-N-oxide)ethylamino)-6-chloropyrazin-2-one-1-acetamide (17)

A stirred solution of 522 mg (1.45 mmol) of 3-(2,2-difluoro-2-(2-pyridyl-N-oxide)ethylamino)-6-chloropyrazin(1H)-2-one-1-acetic acid and 430 mg (2.18 mmol) 2-aminomethyl-3-fluoropyridine dihydrochloride in 10 mL of DMF was added 415 mg (2.17 mmol) of EDC, 295 mg (2.17 mmol) of HOAT and 1.60 mL (14.5 mmol) N-methylmorpholine. After stirring overnight, the volatiles were removed en vacuo. The residue was diluted with water, filtered, and rinsed with water to afford a solid. This material was suspended in MeOH and treated with conc. HCl until the solution became homogeneous. Concentration afforded a gummy solid, which was diluted with EtOH and filtered to give 500 mg of the product as a white solid: ¹H NMR (CD₃OD) δ8.63 (d, 1H, 5.5 Hz), 8.50 (br d, 1H), 8.33 (dd, 1H, 8.8, 8.8 Hz), 7.96–7.93 (m, 1H), 7.84 (m, 1H), 7.71 (m, 2H), 6.90 (s, 1H), 4.93 (s, 2H), 4.75 (s, 2H), 4.61 (t, 2H, 13.8 Hz).

EXAMPLE 2

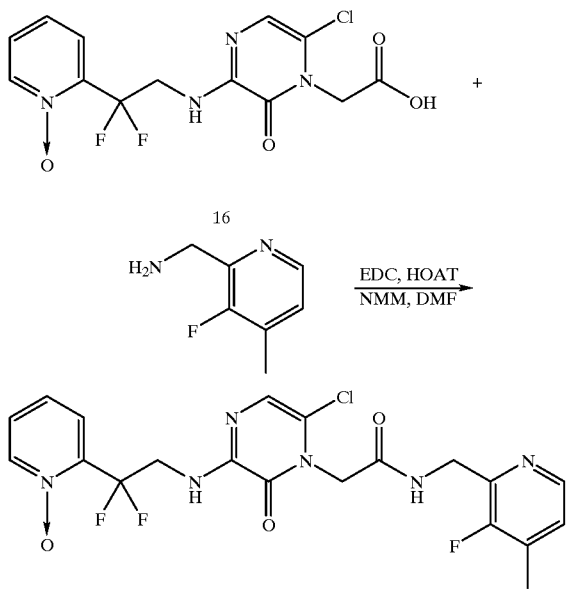

Preparation of 3-Fluoro-4-methyl-2-pyridylmethyl 3-(2,2-difluoro-2-(2-pyridyl-N-oxide)ethylamino)-6-chloropyrazin-2-one-1-acetamide A stirred solution of 90 mg (0.125 mmol) of 3-(2,2-difluoro-2-(2-pyridyl-N-oxide)ethylamino)-6-chloropyrazin(1H)-2-one-1-acetic acid and 40 mg (0.188 mmol) 2-aminomethyl-3-fluoro-4-methylpyridine dihydrochloride in 2 mL of DMF was added 36 mg (0.19 mmol) of EDC, 25 mg (0.19 mmol) of HOAT and 0.20 mL (1.25 mmol) N-methylmorpholine. After stirring overnight, the volatiles were removed en vacuo. The residue was diluted with water, filtered, and rinsed with water to afford a solid. This material was suspended in MeOH and treated with conc. HCl until the solution became homogeneous. Concentration afforded the title compound as a solid: ¹H NMR (CD₃OD) δ8.53 (m, 2H), 7.96 (dd, 1H, 6.2, 6.2 Hz), 7.86 (m, 1H), 7.73 (m, 2H), 6.93 (s, 1H), 4.94 (s, 2H), 4.76 (br s, 2H), 4.62 (t, 2H, 13.8 Hz), 2.61 (d, 3H, 1.7 Hz)

EXAMPLE 3

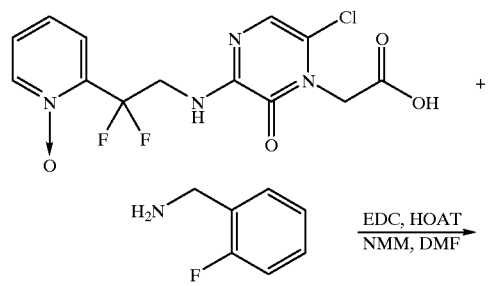

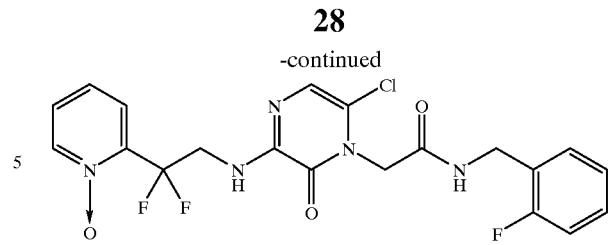

Preparation of 2-Fluorobenzyl 3-(2,2-difluoro-2-(2-pyridyl-N-oxide)ethylamino)-6-chloropyrazin-2-one-1-acetamide A stirred solution of 1.23 g (2.28 mmol, 67% by weight) of 3-(2,2-difluoro-2-(2-pyridyl-N-oxide)ethylamino)-6-chloropyrazin(1H)-2-one-1-acetic acid and 0.391 mL (3.42 mmol) 2-fluorobenzylamine in 7 mL of DMF was added 657 mg (3.42 mmol) of EDC, 313 mg (2.30 mmol) of HOAT and 1.25 mL (11.4 mmol) N-methylmorpholine. After stirring overnight, the volatiles were removed en vacuo. The residue was diluted with 25 mL sat. aq. NaHCO₃, filtered and rinsed with 25 mL water. This solid was further rinsed with dichloromethane (2×15 mL) to afford the title compound as a white powder (0.98 g): ¹H NMR (CDCl₃) □8.24 (d, 1H, 6.3 Hz), 7.62 (dd, 1H, 2.1, 7.8 Hz), 7.52–7.26 (m, 4H), 7.11 (dd, 1H, 7.5, 7.5), 7.03 (m, 1H), 6.88 (s, 1H), 6.43 (br t, 1H, 6.4 Hz), 6.22 (br t, 1H), 4.80 (s, 2H), 4.63 (td, 2H, 13.9, 6.9 Hz), 4.51 (d, 2H, 5.6 Hz). This material was suspended in 50 mL of MeOH and treated with 2.0 mL of 4.0M solution of HCl in dioxane. Concentration afforded the product as a white solid: ¹H NMR (CD₃OD) δ8.52 (dd, 1H, 2.7, 4.7), 7.88 (m, 1H), 7.76–7.70 (m, 2H), 7.36 (ddd, 1H, 1.5, 7.6, 7.6), 7.33–7.27 (m, 1H), 7.13 (ddd, 1H, 0.9, 7.6, 7.6), 7.08 (dd, 1H, 9.3, 9.3), 6.95 (s, 1H), 4.89 (s, 2H), 4.64 (t, 2H, 13.8 Hz 4.46 (s, 2H).

EXAMPLE 4

Preparation of 3-Fluoro-2-pyridylmethyl 3-(2,2-difluoro-2-(2-pyridyl-N -oxide)ethylamino)-6-cyanopyrazin-2-one-1-acetamide hydrochloride

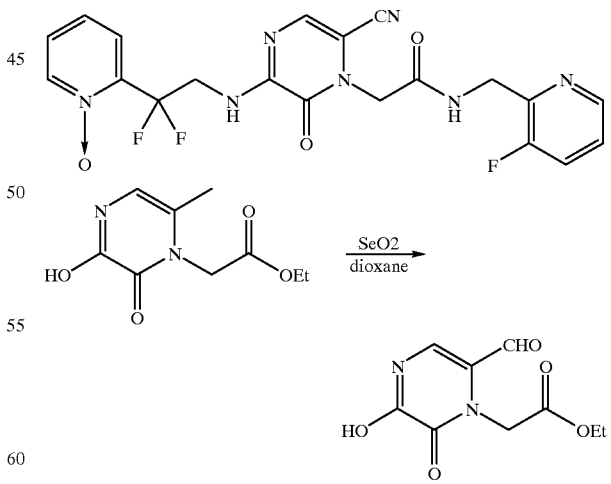

Step A
Ethyl 6-formyl-3-hydroxypyrazin(1H)-2-one-1-acetate
A suspension of the hydroxypyrazinone (5.0 g, 23.6 mmol) and selenium(IV) oxide (2.62g, 23.6 mmol), in 1,4-dioxane (100 mL) was heated to reflux for 24 h. The dark reaction mixture was cooled and filtered through a pad of Celite with MeOH. Concentration and purification of the residue on a SiO₂ column with 3:97 to 10:90 MeOH:CH₂Cl₂ afforded the title compound as an orange solid: ¹H NMR (CD₃OD) δ9.11 (s, 1H), 7.39 (s, 1H), 5.12 (s, 2H), 4.22 (q, 2H, 7.1 Hz), 1.29 (t, 3H, 7.1 Hz).

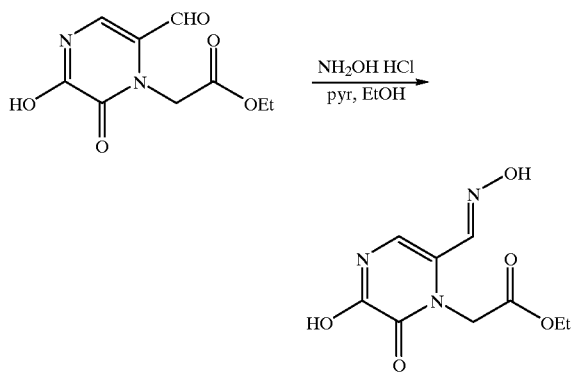

Step B
Ethyl 6-formoximyl-3-hydroxypyrazin(1H)-2-one-1-acetate

To a suspension of the formylpyrazinone (5.43 g, 24.0 mmol) and hydroxylamine hydrochloride (1.67 g, 24.0 mmol) in ethanol (100 mL) was added pyridine (1.90 mL, 24.0 mmol). After 2 h at reflux, the reaction mixture was cooled and concentrated. This crude solid was recrystallized from ethanol (100 mL) to deliver 2.80 g of the title compound as a solid. An additional 1.90 g batch of product was obtained by concentration of the filtrate and trituration with water (50 mL): ¹H NMR (DMSO) δ11.85 (d, 1H), 11.19 (s, 1H), 7.82 (s, 1H), 6.79 (d, 1H, 5.9 Hz), 5.05 (s, 2H), 4.12 (q, 2H, 7.1 Hz), 1.20 (t, 3H, 7.1 Hz).

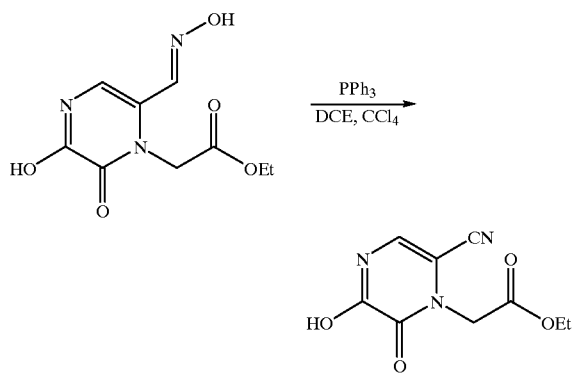

Step C
Ethyl 6-cyano-3-hydroxypyrazin(1H)-2-one-1-acetate

A slurry of the hydroxypyrazinone (2.70 g, 11.2 mmol) and polymer-bound triphenylphosphine (1.55 mmol/g resin: 15.1 g, 23.5 mmol) in 1,2-dichloroethane (90 mL) and carbon tetrachloride (9 mL) was heated to reflux for 1.5 h. The reaction mixture was cooled, filtered, and the resin rinsed with of 1:1 MeOH:CH₂Cl₂ (200 mL). Concentration of the filtrate yielded the product as a tan solid: ¹H NMR (CDCl₃) δ7.06 (s, 1H), 4.73 (s, 2H), 4.29 (q, 2H, 7.1 Hz), 1.33 (t, 3H, 7.1 Hz).

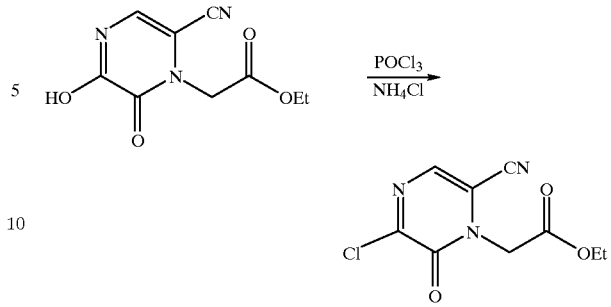

Step D
Ethyl 3-chloro-6-cyanopyrazin(1H)-2-one-1-acetate

A suspension of the hydroxypyrazinone (450 mg, 2.02 mmol) and ammonium chloride (237 mg, 4.44 mmol) in phosphorous oxychloride (2 mL) was heated at reflux for 1.5 h. The reaction mixture was cooled, and the volatiles were removed via rotary evaporation. The residue was quenched with water and solid Na₂CO₃ was added until the mixture was basic. This aqueous mixture was extracted with dichloromethane (3×), and the combined organics were dried (Na₂SO₄), and concentrated to give the product as an amber oil: ¹H NMR (CDCl₃) δ7.60 (s, 1H), 4.87 (s, 2H), 4.32 (q, 2H, 7.1 Hz), 1.31 (t, 3H, 7.1 Hz).

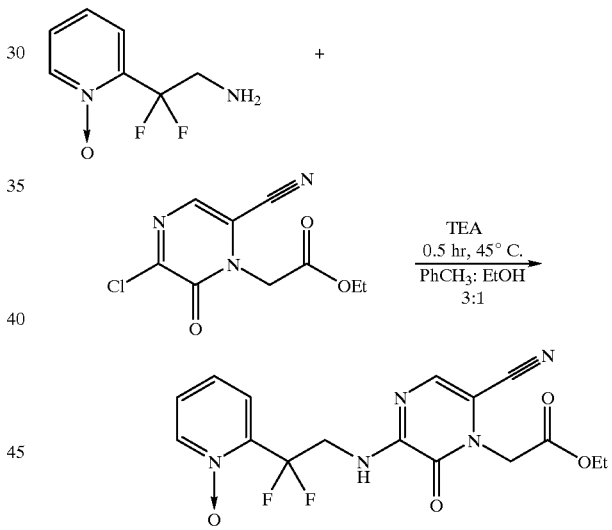

Step E
Ethyl 3-(2,2-difluoro-2-(2-pyridyl-N-oxide-ethylamino)-6-cyanopyrazin(1H)-2-one-1-acetate A mixture of 0.415 g (1.72 mmol) of 2,2-difluoro-2-(2-pyridyl-N-oxide)ethylamine, 0.24 mL (1.72 mmol) of triethylamine and 0.33 g (1.89 mmol) of ethyl 3-chloro-6-cyanopyrazin(1H)-2-one-1-acetate in 6 mL of toluene and 2 mL of ethanol was heated to 45° C. in a sealed tube for 0.5 h. The reaction was concentrated and chromatographed on silica gel, using 3–5% methanol/chloroform saturated with ammonia to afford the title compound as a tan powder: ¹H NMR (CD₃OD) δ8.48 (d, 1H, 7 Hz), 7.91 (s, 1H), 7.76–7.65 (m, 1H), 7.65–7.52 (m, 2H), 4.78 (s, 2H), 4.62 (t, 2H, 16 Hz), 4.23 (q, 2H, 7.1 Hz), 1.28 (t, 3H, 7.1 Hz).

Step F
3-(2,2-Difluoro-2-(2-pyridyl-N-oxide-ethylamino)-6-cyanopyrazin(1H)-2-one-1-acetic acid To a stirred solution of 0.36 g (0.95 mmol) of ethyl 3-(2,2-difluoro-2-(2-pyridyl-N-oxide-ethylamino)-6- cyanopyrazin(1H)-2-one-1-acetate in dimethoxyethane (5 mL) at 0° C. was added 0.95 mL lithium hydroxide solution (2.0M in water). After 0.5 h, warm to room temperature and stir 20 min. Add 0.95 mL water and stir for 15 min. The solution was neutralized using 1.9 mL 1M HCl. Concentration at reduced pressure (azeotrope with PhCH$_3$) afforded an off-white solid containing lithium chloride and the title compound: $^1$H NMR (CD$_3$OD) δ8.36 (d, 1H, 6.2 Hz), 7.69 (dd, 1H, 7.7, 2.2 Hz), 7.51–7.62 (m, 2H), 7.22 (s, 1H), 4.74 (s, 2H), 4.62 (t, 2H, 16 Hz).

Step G
3-Fluoro-2-pyridylmethyl 3-(2,2-difluoro-2-(2-pyridyl-N-oxide)ethylamino)-6-cyanopyrazin-2-one-1-acetamide hydrochloride Prepared in the same manner as above for 3-Fluoro-2-pyridylmethyl 3-(2,2-difluoro-2-(2-pyridyl-N-oxide)ethylamino)-6-chloropyrazin-2-one-1-acetamide. $^1$H NMR (CD$_3$OD) δ8.67 (d, 1H, 5.6 Hz), 8.50–8.42 (m, 2H), 8.07–8.01 (m, 1H), 7.79–7.76 (m, 1H), 7.70–7.64 (m, 2H), 7.23 (s, 1H), 4.79 (s, 2H), 4.58 (s, 2H), 4.62 (t, 2H, 13.1 Hz).

EXAMPLE 5

Preparation of 2-Fluorobenzyl 3-(2,2-difluoro-2-(2-pyridyl-N-oxide)ethylamino)-6-methylpyrazin-2-one-1-acetamide

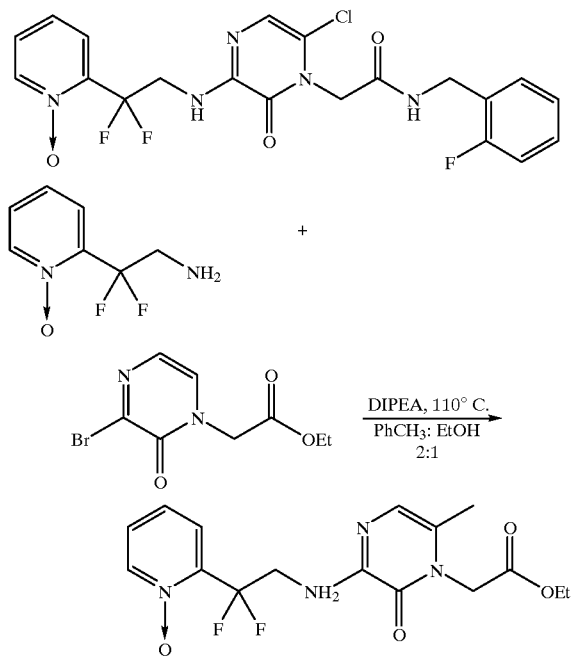

Step A
Ethyl 3-(2,2-difluoro-2-(2-pyridyl-N-oxide-ethylamino)-6-methylpyrazin(1H)-2-one-1-acetate A mixture of 500 mg (2.87 mmol) of 2,2-difluoro-2-(2-pyridyl-N -oxide)ethylamine, 0.52 mL (3.00 mmol) of N,N-diisopropylethylamine and 608 mg (2.39 mmol) of ethyl 3-bromo-6-methylpyrazin(1H)-2-one-1-acetate in 10 mL of toluene and 5 mL of ethanol was heated at 110° C. for 3 d. The reaction was cooled, concentrated and the crude residue was chromatographed on SiO$_2$ using 5:95 MeOH—CH$_2$Cl$_2$ to give the title compound as an orange oil: $^1$H NMR (CDCl$_3$) δ8.25 (d, 1H, 6.4 Hz), 7.61 (dd, 1H, 2.0, 7.9 Hz), 7.33 (ddd, 1H, 2.2, 7.0, 7.0 Hz), 7.28–7.24 (m, 1H), 6.63 (d, 1H, 1.1 Hz), 6.15 (br t, 1H, 6.6 Hz), 4.67 (s, 2H), 4.63 (td, 2H, 13.8, 6.9 Hz), 4.23 (q, 2H, 7.1 Hz), 2.08 (d, 3H, 1.1 Hz), 1.28 (t, 3H, 7.1 Hz).

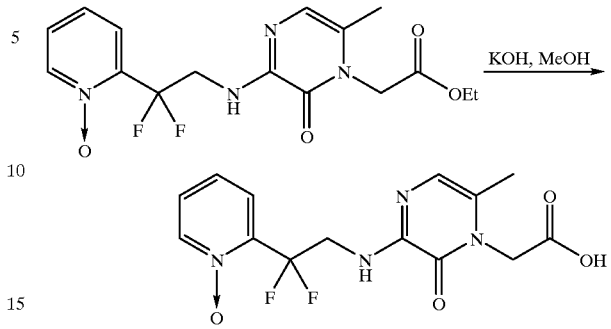

Step B
3-(2,2-Difluoro-2-(2-pyridyl-N-oxide-ethylamino)-6-methylpyrazin(1H)-2-one-1-acetic acid To a stirred solution of 137 mg (0.372 mmol) of ethyl 3-(2,2-difluoro-2-(2-pyridyl-N-oxide-ethylamino)-6-methylpyrazin(1H)-2-one-1-acetate in methanol (20 mL) was added 167 mg potassium hydroxide (3.0 mmol dissolved in 5 mL water). After 2 h the solution was concentrated, diluted with 5 mL of water and acidified to pH=6 using 1.5M HCl. Concentration at reduced pressure (azeotrope with PhCH$_3$) afforded a yellow solid containing potassium chloride and the title compound. This mixture was used directly the amide coupling reactions.

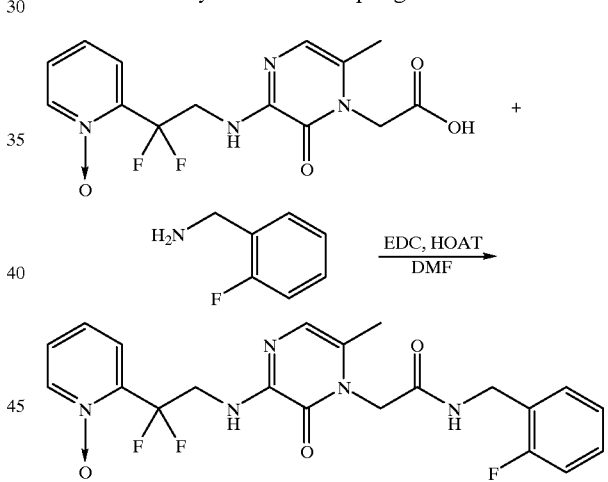

Step C
2-Fluorobenzyl 3-(2,2-difluoro-2-(2-pyridyl-N-oxide)ethylamino)-6-methylpyrazin-2-one-1-acetamide To a stirred solution of 60 mg (0.18 mmol, remainder KCl) of 3-(2,2-difluoro-2-(2-pyridyl-N-oxide)ethylamino)-6-methylpyrazin(1H)-2-one-1-acetic acid and 66 mg (0.53 mmol) 2-fluorobenzylamine in 1.5 mL of DMF was added 48 mg (0.25 mmol) of EDC, and 35 mg (0.25 mmol) of HOAT. After stirring for 3d, the volatiles were removed en vacuo. The residue was partitioned between EtOAc and sat. aq. K$_2$CO$_3$, the layers were separated and the aqueous phase extracted with EtOAc (2×). The organics were combined, concentrated and chromatographed on SiO$_2$ using 5:95 to 10:90 MeOH—CH$_2$Cl$_2$ to give the free base as a white solid This material was suspended in 5 mL of MeOH and treated with 2.0 mL of 4.0M solution of HCl in dioxane. Concentration afforded the product as a white solid: $^1$H NMR (CD$_3$OD) δ8.52 (br d, 1H, 3.5), 7.93 (ddd, 1H, 3.3, 3.3, 6.5), 7.74 (m, 2H), 7.38 (br t, 1H, 7.2), 7.31 (m, 1H), 7.16–7.06 (m, 2H), 6.72 (d, 1H, 2.2 Hz), 4.81 (d, 2H, 3.1 Hz), 4.67 (td, 2H, 2.9, 14.4 Hz), 4.48 (d, 2H, 2.2 Hz), 2.22 (d, 3H, 2.4 Hz).

EXAMPLE 6

3-(2,2-difluoro-2-(2-pyridyl-N-oxide)ethylamino)-6-chloropyrazin-2-one-1-acetamide

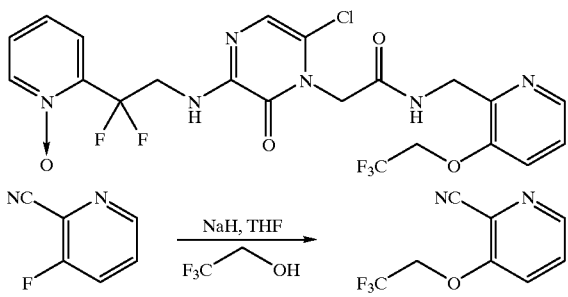

Step A

2-Cyano-3-(2,2,2-trifluoroethoxy)pyridine

A stirred solution of 680 mg (6.80 mmol) of 2,2,2-trifluoroethanol in 25 mL of THF was added 273 mg (6.83 mmol) of sodium hydride (60% dispersion). After 30 min at room temperature, 822 mg (6.73 mmol) of 2-cyano-3-fluoropyridine in 5 mL THF was added via syringe. The reaction was quenched after 1 h, by the addition of 15% $K_2CO_3$ aqueous solution. Concentration gave an oil that was partitioned between water and EtOAc. The layers were separated, the aqueous phase was backwashed with EtOAc (2x), and the combined organic layers were dried ($MgSO_4$) and concentrated to an orange oil. The resultant crude residue was chromatographed on $SiO_2$ using 25:75 EtOAc-hexanes to afford the title compound as a yellow oil: $^1$H NMR (CDCl$_3$) δ8.43 (d,1H, 4.6 Hz), 7.55 (dd, 1H, 4.6, 8.7 Hz), 7.42 (d, 1H, 8.7 Hz), 4.55 (q, 2H, 7.8 Hz).

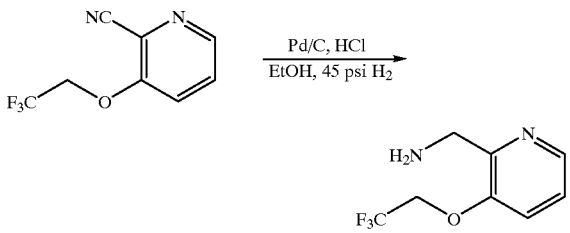

Step B

2-Aminomethyl-3-(2,2,2-trifluoroethoxy)pyridine dihydrochloride

A solution of 0.53 g (2.62 mmol) of 2-cyano-3-(2,2,2-trifluoroethoxy)pyridine and 0.66 mL (7.87 mmol) of conc. HCl in 50 mL of ethanol was hydrogenated over 0.27 g of 10% palladium on carbon at 45 psi for 1.5 h. The catalyst was removed by filtration through a pad of Celite with EtOH. The solvents were removed at reduced pressure to give the title compound: $^1$H NMR (CD$_3$OD) δ8.36 (d, 1H, 5.0 Hz), 7.73 (d,1H, 8.6 Hz), 7.54 (dd, 1H, 8.4, 5.0 Hz), 4.80 (q, 2H, 8.3 Hz), 4.33 (s, 2H).

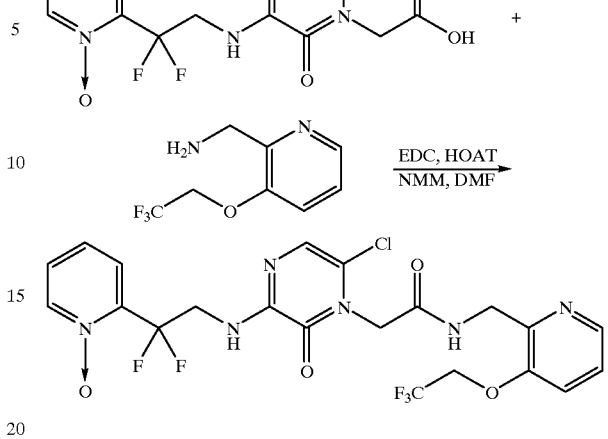

Step C 3-(2,2,2-Trifluoroethoxy)-2-pyridylmethyl 3-(2,2-difluoro-2-(2-pyridyl-N-oxide)ethylamino)-6-chloropyrazin-2-one-1-acetamide To a stirred solution of 83 mg (0.23 mmol) of 3-(2,2-difluoro-2-(2-pyridyl-N-oxide)ethylamino)-6-chloropyrazin (1H)-2-one-1-acetic acid and 77 mg (0.28 mmol) 2-aminomethyl-3-(2,2,2-trifluoroethoxy)pyridine dihydrochloride in 1.5 mL of DMF was added 35 mg (0.25 mmol) of EDC, 50 mg (0.253 mmol) of HOAT and 0.50 mL N-methylmorpholine. After stirring overnight, the volatiles were removed en vacuo. The residue was diluted with water, filtered, and rinsed with water to afford a solid. This crude material was filtered through a short plug of SiO$_2$ with 100% EtOAc to 10:90 MeOH:EtOAc to give a white solid. This material was suspended in MeOH and treated with conc. HCl until the solution became homogeneous. Concentration afforded the title compound as a white solid: $^1$H NMR (CD$_3$OD) δ8.46 (m , 2H), 8.36 (d, 1H, 8.8 Hz), 8.01 (dd, 1H, 6.0, 8.5 Hz), 7.79 (m, 1H), 7.66 (m, 2), 6.85 (s, 1H), 4.97 (q, 2H, 8.2 Hz), 4.94 (s, 2H), 4.73 (s, 2H), 4.59 (t, 2H, 13.5 Hz).

EXAMPLE 7

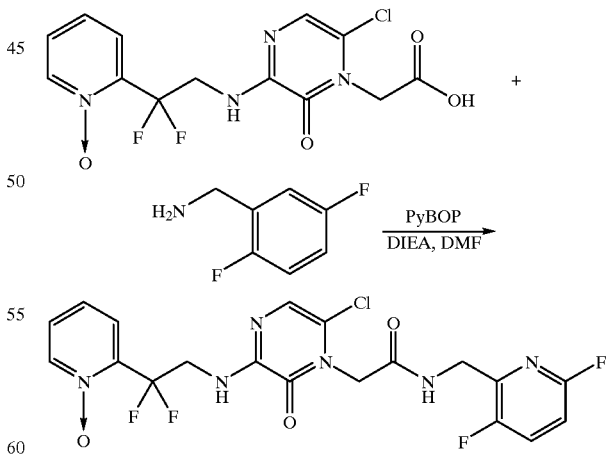

Preparation of 2,5-Difluoro-l1-phenylmethyl 3-(2,2-difluoro-2-(2-pyridyl-N-oxide)ethylamino)- 6-chloropyrazin-2-one-1-acetamide hydrochloride A stirred solution of 200 mg, (0.556 mmol) of 3-(2,2-difluoro-2-(2-pyridyl-N-oxide)ethylamino)-6-chloropyrazin (1H)-2-one-1-acetic acid and 66.2 uL (0.566 mmol) 2,5-diflurobenzylamine in 2 mL of DMF was added 321 mg (0.617 mmol) of benzotriazol-1-yloxytriprrolidinophosphonium hexafluorophosphate (PyBOP) and 0.267 mL (1.67 mmol) N,N-diisopropylethylamine. After stirring, for 2 h, add 10 mL water and stir for 10 min. Filter off white solid and dry under vacuum at 40° C. for 1 h. This material was suspended in EtOAc and treated with 1 mL HCl/EtOAc (0.1576 s/mL). The solvent was removed in vacuo to give the product as a white solid: $^1$H NMR (DMSO) δ8.82 (t, 1H, 5.7 Hz), 8.35 (d, 1H, 6.6 Hz), 7.62–7.54 (m, 2H), 7.39 (t, 1H, 7.8), 7.27–7.22 (m, 1H), 7.18–7.09 (m, 2H), 6.80 (s, 1H), 4.75 (s, 2H), 4.46 (dt, 2H, 6.6, 13.3 Hz,), 4.31 (d, 2H, 5.6 Hz).

EXAMPLE 8

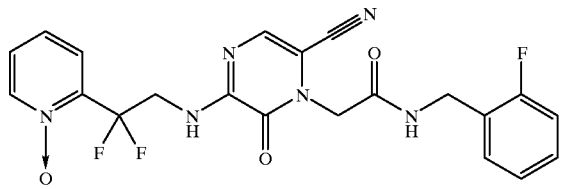

Preparation of 2-Fluorobenzyl 3-(2,2-difluoro-2-(2-pyridyl-N-oxide)ethylamino)-6-cyanopyrazin-2-one-1-acetamide hydrochloride Prepared in the same manner as above by coupling 3-(2,2-difluoro-2-(2-pyridyl-N-oxide)ethylamino)-6-cyanopyrazin(1H)-2-one-1-acetic acid with 2-fluorobenzylamine. $^1$H NMR (CD$_3$OD) δ8.54 (t, 1H, 3.7 Hz), 7.83–7.79 (m, 1H), 7.74–7.70 (m, 2H), 7.40–7.25 (m, 2H), 7.26 (s, 1H), 7.15–7.04 (m, 2H), 4.74 (s, 2H), 4.64 (t, 2H, 12.9 Hz), 4.47 (s, 2H).

EXAMPLE 9

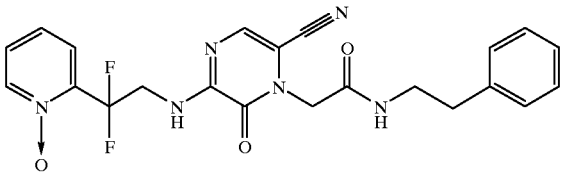

Phenethyl 3(2,2-difluoro-2-(2-pyridyl-N-oxide)ethylamino)-6-cyanopyrazin-2-one-1-acetamide trifluoroacetate Prepared in the same manner as above by coupling 3-(2,2-difluoro-2-(2-pyridyl-N-oxide)ethylamino)-6-cyanopyrazin(1H)-2-one-1-acetic acid with pheethyl amine. Further purification by preparative HPLC afforded the product. $^1$H NMR (DMSO) δ8.57 (t, 1H, 6.6 Hz), 8.41 (t, 2H, 5.5 Hz), 8.36 (d, 1H, 6.4 Hz), 7.63–7.55 (m, 2H), 7.45 (s, 1H), 7.40 (t, 1H, 7.8 Hz), 7.31–7.27 (m, 2H), 7.22–7.17 (m, 3H), 4.60–4.51 (m, 4H), 3.33–3.28 (m, 2H), 2.72 (t, 2H, 7.5 Hz).

EXAMPLE 10

Preparation of 3-(Methylthio)-2-pyridylmethyl-3-(2,2-difluoro-2-(2-pyridyl-N-oxide)ethylamino)-6-chloropyrazin-2-one-1-acetamide

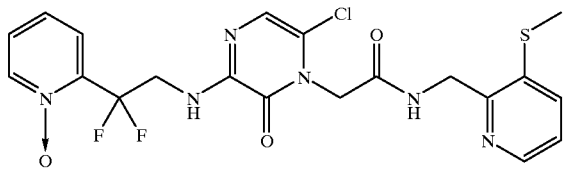

Step A
2-Cyano-3-methylthiopyridine

A stirred solution of 1.00 g (8.19 mmol) of 2-cyano-3-fluoropyridine and 0.631 g (9.01 mmol) of sodium thiomethoxide in 8 mL of DMF was stirred at room temperature for 1 h. The reaction mixture was diluted with water (80 mL) and stirred for 5 min. The resulting solid was filtered and dried on a high vacuum line to give the product as an off-white solid: $^1$H NMR (CDCl$_3$) δ8.46 (d,1H, 4.6 Hz), 7.66 (d, 1H, 8.3 Hz), 7.44 (dd, 1H, 4.6, 8.3 Hz), 2.58 (s, 3H).

Step B
2-Aminomethyl-3-methylthiopyridine dihydrochloride

A stirred solution of 659 mg (4.39 mmol) of 2-cyano-3-methylthiopyridine in 25 mL of methanol and 5 mL of 6M aq. HCl was hydrogenated over 659 mg of 10% palladium on carbon at 55 psi for 5 h. The catalyst was removed by filtration and the solvents concentrated at reduced pressure. The resulting material was diluted with methanol and concentrated (2x) to give 3-2 as an off-white solid: 1H NMR (CD$_3$OD): δ2.58 (s, 3H), 4.28 (s, 2H), 7.43 (m, 1H), 7.86 (dd, J=1.3 and 8.1 Hz, 1H), 8.43 (dd, J=1.3 and 4.8 Hz, 1H).

Step C
3-(Methylthio)-2-pyridylmethyl-3-(2,2-difluoro-2-(2-pyridyl-N-oxide)ethylamino)-6-chloropyrazin-2-one-1-acetamide The title compound was prepared according to the general pyBOP coupling procedure and was isolated as a colorless solid: $^1$H NMR (d$_6$-DMSO, 400 MHz): δ8.69 (m, 1H), 8.36–8.32 (br m, 2H), 7.71 (d, J=8 Hz, 1H), 7.60 (d, J=6 Hz, 1H), 7.55–7.51 (br m, 2H), 7.41–7.32 (br m, 2H), 6.78 (s, 1H), 4.79 (s, 2H), 4.47–4.41 (br m, 4H), 2.50 (s, 3H). HRMS (FAB) M+H: 497.0960.

EXAMPLE 11

Preparation of 3-(Methylsulfoxy)-2-pyridylmethyl 3-(2,2-difluoro-2-(2-pyridyl-N-oxide)ethylamino)-6-chloropyrazin-2-one-1-acetamide To a mixture of 3-(methylthio)-2-pyridylmethyl-3-(2,2-difluoro-2-(2-pyridyl-N-oxide)ethylamino)-6-chloropyrazin-2-one-1-acetamide (120 mg, 0.241 mmol) in carbon tetrachloride (14 mL) at room temperature was added (−)-[(8,8-dichlorocamphoryl)-sulfonyl]oxaziridine (75.4 mg, 0.253 mmol). The mixture was degassed and purged with argon six times at 25° C. and was then placed in a pre-heated 40° C. oil bath. After 10 min., the mixture was heated to 80° C. under argon and stirred for 24 h. The reaction mixture was allowed to cool to room temperature and was filtered. The solid residue was washed with diethyl ether and dried in vacuo. Separation of unreacted sulfide and the two enantiomers was performed on a Chiralcel OD column by isocratic elution with 7:3 ethanol:hexanes/0.1% trifluoroacetic acid to collect as colorless solids unreacted sulfide, followed by the faster moving enantiomer and finally the slower moving enantiomer 446:

Faster moving enantiomer: $^1$H NMR (CD$_3$OD, 400 MHz): δ8.71 (m, 1H), 8.43–8.37 (br m 2H), 7.71–7.64 (m, 2H), 7.60–7.55 (m, 2H), 6.72 (m, 1H), 4.87 (s, 2H), 4.69–4.52 (4H), 2.87 (s, 3H). HRMS (FAB) M+H: 513.0902.

Slower moving enantiomer: $^1$H NMR (CD$_3$OD, 400 MHz): δ8.71 (m, 1H), 8.42–8.38 (br m, 2H), 7.71–7.66 (m, 2H), 7.59–7.54 (m, 2H), 6.71 (m, 1H), 4.87 (s, 2H), 4.65–4.53 (br m, 4H), 2.86 (s, 3H). HRMS (FAB) M+H: 513.0929.

EXAMPLE 12

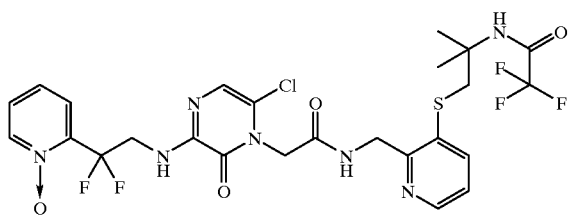

Preparation of 3-(2-methyl-2-trifluoroacetamidopropanethio)-2-pyridylmethyl 3-(2,2-difluoro-2-(2-pyridyl-N-oxide)ethylamino)-6-chloropyrazin-2-one-1-acetamide Step A
2-Amino-2-methylpropanethiol Hydrochloride A mixture of 2,4,4-trimethyl-2-oxazoline (12.76 mL, 100 mmol) and phosphorus pentasulfide (26.67 g, 60 mmol) in toluene (100 mL) was stirred at reflux for 16 h. The mixture was cooled, 20% aqueous sodium hydroxide (72 mL) was added and the mixture stirred until the remaining solids were in suspension. This mixture was filtered through a glass frit and the organic component of the filtrate was washed with water (2×) and dried (Na$_2$SO$_4$). The resulting solution was extracted with 2.5M HCl (50 mL) and the red aqueous solution was heated to reflux. After 64 h the resulting lime green solution was cooled and evaporated in vacuo, azeotroping with isopropanol. The residue was recrystallized from isopropanol and collected by filtration, washing with cold isopropanol and ether to give the title compound as a colorless crystalline solid: 1H NMR (d$_6$ DMSO) δ1.27 (s, 6H), 2.73 (s, 2H).

Step B
2-Methyl-2-trifluroacetamidopropanethiol

Trifluoroacetic anhydride (0.50 mL, 3.53 mmol) was added dropwise to a stirred mixture of 2-amino-2-methylpropanethiol hydrochloride (500 mg, 3.53 mmol) and triethylamine (0.98 mL, 7.06 mmol) in methylene chloride (25 mL) at 0° C. and the resulting mixture was warmed to room temperature. After 16 h the reaction was washed with 10% sodium hydrogen carbonate solution and brine, dried (Na$_2$SO$_4$) and evaporated in vacuo to give the title compound as a colorless oil: 1H NMR (CDCl$_3$) δ1.45 (s, 6H), 2.92 (d, J=9.2 Hz, 2H), 6.23 (br s, 1H).

Step C
2-Cyano-3-(2-methyl-2-trifluoroacetamidopropanethio)-pyridine

A solution of 2-cyano-3-fluoropyridine (0.20 g, 1.64 mmol), 2-methyl-2-trifluroacetamidopropanethiol (330 mg, 1.64 mmol) and sodium hydrogen carbonate (0.138 g, 1.64 mmol) in methanol (16 mL) was stirred at room temperature for 64 h. The reaction mixture was evaporated in vacuo and the residue was partitioned between ethyl acetate and brine, dried (Na$_2$SO$_4$) and evaporated in vacuo. The residue was purified by column chromatography on silica (eluting with chloroform) to give the title compound: $^1$H NMR (CDCl$_3$) δ$^1$H NMR (CDCl$_3$) δ1.55 (s, 6H), 3.56 (s, 2H), 6.17 (br s, 1H), 7.44 (dd, 4.6, 8.2 Hz, 1H), 7.88 (dd, J=1.5 and 8.2 Hz, 1H), 8.46 (dd, J=1.5 and 4.6 Hz, 1H).

Step D
2-Aminomethyl-3-(2-methyl-2-trifluoroacetamidopropanethio)-pyridine

A mixture of 2-cyano-3-(2-methyl-2-trifluoroacetamidopropanethio) -pyridine (86 mg, 0.28 mmol) and 10% palladium on carbon (150 mg) in methanol (10 mL) and 6M aq. HCl (2 mL) was shaken in a Parr apparatus under hydrogen (60 psi) for 3 h. More catalyst (50 mg) was added and after a further 16 h, the catalyst was removed by filtration and the solvents concentrated in vacuo. The residue was purified by column chromatography on silica (eluting with 95:5 ammonia saturated chloroform/methanol) to give the title compound: 1H NMR (CDCl$_3$): δ1.49 (s, 6H), 1.83 (br s, 2H), 3.36 (s, 2H), 4.14 (s, 2H), 6.17 (br s, 1H), 7.14 (dd, 4.6, 7.8 Hz, 1H), 7.25 (br s, 1H), 7.71 (dd, J=1.5 and 7.8 Hz, 1H), 8.40 (dd, J=1.5 and 4.6 Hz, 1H).

Step D
3-(2-methyl-2-trifluoroacetamidopropanethio)-2- pyridylmethyl 3-(2,2-difluoro-2-(2-pyridyl-N-oxide)ethylamino)-6-chloropyrazin-2-one-1-acetamide The title compound was prepared according to the general pyBOP coupling procedure and was isolated as a colorless solid: $^1$H NMR (CD$_3$OD, 300 MHz): δ8.36 (m, 2H), 7.91–7.88 (m, 1H), 7.69 (m, 1H), 7.56–7.54 (m, 2H), 7.30–7.27 (m, 1H), 6.70 (s, 1H), 4.91 (s, 2H), 4.67 (s, 2H), 4.56 (t, J=12 Hz, 2H), 3.31 (s, 2H), 1.46 (s, 6H). HRMS (FAB) M+H: 650.1374.

EXAMPLE 13

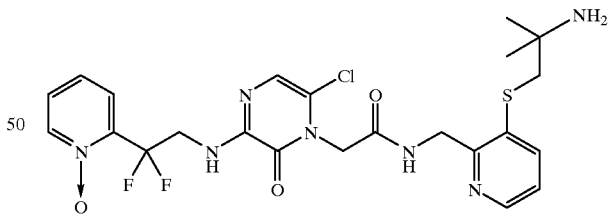

3-(2-methyl-2-aminopropanethio)-2-pyridylmethyl 3-(2,2-difluoro-2-(2-pyridyl-N-oxide)ethylamino)-6-chloropyrazin-2-one-1-acetamide To a solution of 3-(2-methyl-2-trifluoroacetamidopropanethio)-2-pyridylmethyl 3-(2,2-difluoro-2-(2-pyridyl-N-oxide)ethylamino)-6-chloropyrazin-2-one-1-acetamide (22 mg, 0.034 mmol) in methanol (1.2 mL) and water (1 mL) at room temperature was added potassium carbonate (14.1 mg, 0.102 mmol). The mixture was heated to 60° C. for 3 h. Potassium carbonate (14.1 mg, 0.102 mmol) was again added, and the reaction was stirred for 3 h. A third portion of potassium carbonate (14.1 mg, 0.102 mmol) was added, and the reaction was stirred for 5 h. The methanol was removed in vacuo, and the remaining aqueous solution was extracted into chloroform several times. The organic layer was dried over sodium sulfate and concentrated in vacuo to afford the title compound as the free base. $^1$H NMR (CD$_3$OD, 400 MHz): δ8.70–8.65 (m, 2H), 8.45 (m, 1H), 7.96–7.93 (m, 1H), 7.78–7.76 (m, 1H), 7.65–7.62 (m, 2H), 6.82 (s, 1H), 4.98 (s, 2H), 4.84 (s, 2H), 4.59 (t, J=16 Hz, 2H), 3.57 (s, 2H), 1.49 (s, 6H). LCMS (ES) M+H: 554.1.

EXAMPLE 14

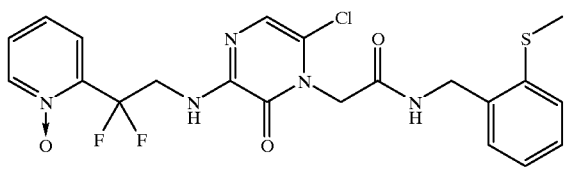

2-(Methylthio)benzyl 3-(2,2-difluoro-2-(2-pyridyl-N-oxide)ethylamino)-6-chloropyrazin-2-one-1-acetamide The title compound was prepared according to the general pyBOP coupling procedure and was isolated as a colorless solid: $^1$H NMR (CD$_3$OD, 300 MHz): δ8.37 (m, 1H), 7.71–7.69 (m, 1H), 7.56–7.54 (br m, 2H), 7.30–7.28 (br m, 3H), 7.15 (m, 1H), 6.70 (s, 1H), 4.86 (s, 2H), 4.57 (t, J=15 Hz, 2H), 4.46 (s, 2H), 2.48 (s, 3H). HRMS (FAB) M+H: 496.1034.

EXAMPLE 15

Preparation of 2-(Methylsulfonyl)benzyl 3-(2,2-difluoro-2-(2-pyridyl-N-oxide)ethylamino)- 6-chloropyrazin-2-one-1-acetamide

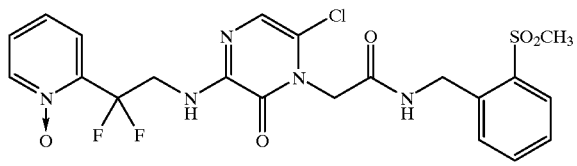

Step A
N-Boc-2-(methylsulfonyl)-benzylamine

To a solution of 2-(methylthio)-benzyl amine (160 mg, 1.04 mmol) in dichloromethane (3 mL) was added di-tert-butyl dicarbonate (273 mg, 1.25 mmol) and the reaction mixture was stirred at room 25° C. for 2 h. Concentration in vacuo provided crude N-Boc-2-(methylthio)-benzylamine which was used as is in the next step.

To a stirred solution of N-Boc-2-(methylthio)-benzylamine (1.04 mmol) in dichloromethane (5 mL) was added m-chloroperoxybenzoic acid (540 mg, 1.56 mmol) by portions. After 2 h, the reaction mixture was diluted with diclhloromethane (5 mL) and m-chloroperoxybenzoic acid (290 mg) was added and the reaction mixture stirred for 18 h. The reaction mixture was diluted with methanol (2 mL), m-chloroperoxybenzoic acid (180 mg) was added and the reaction mixture stirred for 18 h. The reaction mixture was concentrated in vacuo, diluted with diethyl ether, washed with saturated aqueous sodium bicarbonate several times and brine, dried over sodium sulfate, concentrated in vacuo, and the crude product was purified by flash chromatography (silica gel, hexane to 50% ethyl acetate in hexane) to provide the title compound: $^1$H NMR (CDCl$_3$, 400 MHz): δ8.00 (d, 1H); 7.70–7.60 (m, 2H); 7.48 (t, 1H); 5.48 (b s, 1H); 4.62 (d, 2H); 3.15 (s, 3H); 1.42 (s, 9H). MS (ES) M+Na: 308.1.

Step B
2-(Methylsulfonyl)-benzylamine hydrochloride

Through a solution of N-Boc-2-(methylsulfonyl)-benzylamine (225 mg) in dichloromethane (20 ml) was bubbled HCl (g) for 10 min. The flask is sealed and stirred for 18 hrs. Argon was bubbled through the reaction mixture which was then concentrated in vacuo to provide the title compound as a white solid. $^1$H NMR (CD$_3$OD, 300 MHz): δ8.25 (dd, 1H); 8.90–8.65 (m, 3H); 4.50 (s, 2H); 3.25 (s, 3H).

Step C
2-(Methylsulfonyl)benzyl 3-(2,2-difluoro-2-(2-pyridyl-N-oxide)ethylamino)-6-chloropyrazin-2-one-1-acetamide The title compound was prepared according to the general pyBOP coupling procedure and was isolated as a colorless solid: $^1$H NMR (d$_6$-DMSO, 400 MHz): δ8.93 (m, 1H), 8.36–8.34 (m, 1H), 7.92 (m, 1H), 7.71 (m, 1H), 7.61–7.54 (br m, 3H), 7.40–7.37 (m, 1H), 6.80 (s, 1H), 4.79 (s, 2H), 4.72 (s, 2H), 4.47 (br m, 2H), 3.28 (s, 3H). HRMS (FAB) M+H: 528.0912.

EXAMPLE 16

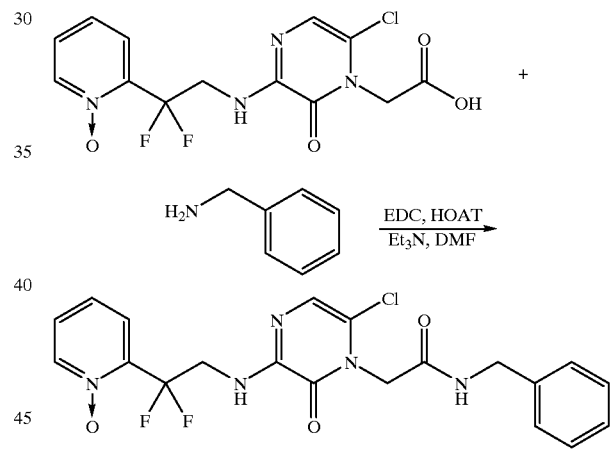

Benzyl-3-(2,2-difluoro-2-(2-pyridyl-N-oxide) ethylamino)-6-chloropyrazin-2-one-1-acetamide White solid: TLC: Silica G$_f$ (160/10/1 of CH$_2$Cl$_2$/MeOH/ Conc. NH$_4$OH) R$_f$=0.22 single, clean spot. HPLC: 100% at 215 nm and 254 nm.; MS: M+H=449.9 (ES);

$^1$H NMR (d$_6$-DMSO) δ8.79 (br t, 1H), 8.36 (d, 1H, 6.4 Hz), 7.62–7.54 (m, 3H), 7.42–7.24 (m, 6H), 6.80 (s, 1H), 4.74 (s, 2H), 4.44 (td, 2H, 13.2, 6.4 Hz), 4.30 (d, 2H, 5.5 Hz).

EXAMPLE 17

Step A
2-Cyano-3-(2-hydroxy-2-methylpropanethio)pyridine

A stirred solution of 2.44 g (20.0 mmol) of 2-cyano-3-fluoropyridine, 2.34 g (22.0 mmol) of 2-hydroxy-2-methylpropanethiol, and 1.68 g (20.0 mmol) of sodium hydrogencarbonate in 50 ml of methanol was heated to reflux for 3 hours. The reaction was cooled to room temperature and partitioned between water (200 mL) and methylene chloride (3×150 mL). The organic extracts were dried over sodium sulfate, filtered and concentrated under reduced pressure. This residue was chromatographed on SiO$_2$ using 3:97 methanol-chloroform, yielding a white solid: $^1$H NMR (CDCl$_3$): δ1.39 (s, 6H), 3.18 (s, 2H), 7.42 (dd, 1H), 7.94 (dd, 1H), 8.49 (dd, 1H).

Step B
2-Aminomethyl-3-(2-hydroxy-2-methylpropanethio)pyridine

A stirred solution of 1.9 g (9.1 mmol) of 2-cyano-3-(2-hydroxy-2-methylpropanethio)pyridine in 50 mL of methanol and 10 mL of aqueous 6M HCl was hydrogenated over 3.8 g of 10% palladium on carbon at 55 psi for 72 hours. The catalyst was removed by filtration and the solvents concentrated at reduced pressure. The residue was chromatographed on SiO$_2$ using 5:95 methanol-chloroform saturated with ammonia yielding a yellow oil: $^1$H NMR (CDCl$_3$): δ1.32 (s, 6H), 3.07 (s, 2H), 4.18 (s, 2H), 7.17 (dd, 1H), 7.78 (dd, 1H), 8.39 (dd, 1H).

2-tert-butoxycarbonylaminomethyl-3-(2-hydroxy-2-methylpropanethio)pyridine

A stirred solution of 1.51 g (5.3 mmol) 2-Aminomethyl-3-(2-hydroxy-2-methylpropanethio)pyridine dihydrochoride, 1.3 g (6.0 mmol), di-tert-butyl-dicarbonate, and 1.5 g (18.0 mmol) sodium hydrogencarbonate in 150 mL of tetrahydrofuran and 50 mL water was heated to 50° C. for 2 hours. The reaction was partitioned between water and methylene chloride. The organic extracts were dried over sodium sulfate, filtered and concentrated under reduced pressure. This residue was chromatographed on SiO$_2$ using 70:30 ethyl acetate-hexanes, yielding a clear oil: $^1$H NMR (CDCl$_3$): δ1.33 (s, 6H), 1.48 (s, 9H), 3.08 (s, 2H), 4.58 (d, 2H), 6.05 (bs, 1H), 7.16 (dd, 1H), 7.75 (dd, 1H), 8.37 (dd, 1H).

Step D
2-tert-butoxycarbonylaminomethyl-3-(2-hydroxy-2-methylpropanesulfonyl)pyridine To a stirred solution of 224 mg (0.7 mmol) 2-tert-butoxycarbonylaminomethyl-3-(2-hydroxy-2-methylpropanethio)pyridine and 10 mg sodium tungstate dihydrate in 1 mL water and 1 mL 1,2 dichloroethane at 60° C. was added 0.17 mL (1.5 mmol) 30% H$_2$O$_2$. After 1 hour an additional 0.17 mL 30% H$_2$O$_2$ was added and the reaction stirred vigorously at 75° C. overnight. The reaction was quenched with excess sodium sulfite solution and partitioned between water and methylene chloride. The organic extracts were dried over sodium sulfate, filtered, and concentrated under reduced pressure. The residue was purified by chromatography on SiO$_2$ using 0:100 to 5:95 methanol-chloroform yielding a clear oil: $^1$H NMR (CDCl$_3$): δ1.41 (s, 9H), 1.44 (s, 6H), 3.73 (s, 2H), 4.74 (d, 2H), 5.83 (bt, 1H), 7.42 (dd, 1H), 8.31 (dd, 1H), 8.78 (dd, 1H).

Step E
2-Aminomethyl-3-(2-hydroxy-2-methylpropanesulfonyl)pyridine

A solution of 121 mg (0.35 mmol) 2-tert-butoxycarbonylaminomethyl-3-(2-hydroxy-2-methylpropanesulfonyl)pyridine, 10 mL 4M HCl/dioxane and 5 mL methanol was stirred at room temperature for 2 hours. The reaction was evaporated to dryness. The residue was treated with triethylamine and purified by chromatography on SiO$_2$ using 0:100 to 5:95 methanol-chloroform yielding a yellow oil: $^1$H NMR (CDCl$_3$): δ1.44 (s, 6H), 3.56 (s, 2H), 4.41 (s, 2H), 7.43 (dd, 1H), 8.32 (dd, 1H), 8.79 (dd, 1H).

Step F
3-(2-hydroxy-2-methylpropanesulfonyl)-2-pyridylmethyl 3-(2,2-difluoro-2-(2-pyridyl-N-oxide)ethylamino)-6-chloropyrazin-2-one-1-acetamide A solution of 54 mg (0.10 mmol) 3-(2,2-difluoro-2-(2-pyridyl-N-oxide)ethylamino)- 6-chloropyrazin(1H)-2-one-1-acetic acid, 24 mg (0.10 mmol) 2-aminomethyl-3-(2-hydroxy-2-methylpropanesulfonyl)pyridine, 29 mg (0.15 mmol) EDC, 20 mg (0.15 mmol) HOBT, and 101 mg (1.0 mmol) NMM in 2 mL DMF was stirred overnight at room temperature. This solution was partitioned between water and methylene chloride. The organic extracts were dried over sodium sulfate, filtered and concentrated under reduced pressure. This residue was purified by chromatography on SiO$_2$ using 10:90 methanol-chloroform. The free-base was taken up in methanol and treated with excess 1M HCl in ether to generate the bis-HCl salt. This was precipitated from solution with ether, filtered and dried yielding a white solid: $^1$H NMR (CD$_3$OD): δ1.41 (s, 6H), 3.64 (s, 2H), 4.60 (t, J=13.4 Hz, 2H), 4.97 (s, 4H), 6.86 (s, 1H), 7.67 (m, 3H), 7.81 (m, 1H), 8.47 (m, 2H), 8.83 (dd, J=5 Hz, 1.7 Hz, 1H); HRMS (FAB) calcd C$_{23}$H$_{25}$N$_6$O$_6$SClF$_2$ (M+1) 587.1286, found 587.1272.

EXAMPLE 18

Preparation of 2-Cyano-5-methoxybenzyl 3-[2,2-difluoro-2-(2-pyridyl-N-oxide)ethylamino)- 6-chloropyrazin-2-one-1-acetamide

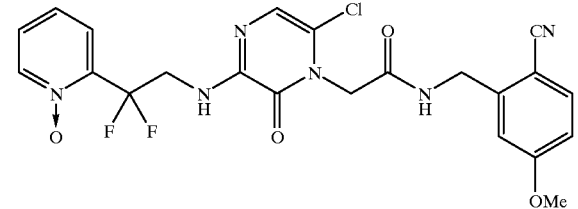

Step A
2-Cyano-5-methoxybenzyl alcohol

To a solution of ethyl 2-cyano-5-methoxybenzoate (5 g, 24 mmol) in THF (100 mL) at room temperature was added a solution of LiBH$_4$ in THF (2M, 12 mL, 24 mmol). After 19 h, there was about 60% conversion of starting material. An additional quantity of LiBH$_4$ in THF (2M, 12 mL, 24 mmol) was added and stirring continued for an additional 15 h. The solvent was removed under reduced pressure then water was carefully added to the residue. Excess hydride was destroyed by careful proportionwise addition of a saturated aqueous solution of NH$_4$Cl. Once complete, the resulting mixture was extracted with ether and then with ethyl acetate. The combined extracts were dried over Na$_2$SO$_4$ and the solvents then removed in vacuo. The residue was purified by column chromatography eluting with 2:1:2 hexane/chloroform/ethyl acetate. The title compound was isolated as a white solid: $^1$H NMR (CDCl$_3$) δ7.58 (d, J=8.5 Hz, 1H), 7.15 (d, J=2.7 Hz, 1H), 6.86 (dd, J=2.7, 8.5 Hz, 1H), 4.89 (d, J=6.0 Hz, 2H), 3.88 (s, 1H), 2.01 (t, J=6.0 Hz, 1H).

Step B
2-Cyano-5-methoxybenzyl azide

A solution of 2-cyano-5-methoxybenzyl alcohol (1.8 g, 11 mmol) in THF (50 mL) was cooled to 0° C. and then treated sequentially with diphenylphosphoryl azide (2.8 mL, 13 mmol) and DBU 1.9 mL, 13 mmol), the former added in one portion and the latter dropwise. The reaction mixture was allowed to warm gradually to room temperature and to then stir there overnight. The solvent was removed and the residue partitioned between ethyl acetate and water. The organic phase was washed with dilute citric acid, then brine and dried (Na$_2$SO$_4$). The solvent was removed in vacuo and the residue purified by column chromatography eluting with 4:1:1 hexane/chloroform/ethyl acetate to give the product as a yellow oil: $^1$H NMR (CDCl$_3$) δ7.62 (d, J=8.6 Hz, 1H), 7.02 (d, J=2.6 Hz, 1H), 6.92 (dd, J=2.6, 8.6 Hz, 1H), 4.59 (s, 2H), 3.89 (s, 3H).

Step C
2-Cyano-5-methoxybenzylamine

A mixture of 2-cyano-5-methoxybenzyl azide (1 g, 5.3 mmol) and 10% palladium on carbon (500 mg) in ethyl acetate (30 ml) was stirred at room temperature under an atmosphere of hydrogen for 1 h. The catalyst was removed by filtration through a bed of Celite and the filtrate concentrated to yield the product as an orange oil: $^1$H NMR (CDCl$_3$) δ7.56 (d, J=8.5 Hz, 1H), 7.07 (d, J=2.5 Hz, 1H), 6.82 (dd, J=2.5, 8.5 Hz, 1H), 4.05 (br s, 2H), 3.87 (s, 3H).

Step D
2-Cyano-5-methoxybenzyl 3-[2,2-difluoro-2-(2-pyridyl-N-oxide)ethylamino]-6-chloropyrazin-2-one-1-acetamide The title compound was prepared from 2-cyano-5-methoxy-benzylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was further purified by preparative HPLC and characterized as the trifluoroacetate salt: $^1$H NMR (CD$_3$OD) δ8.86 (m, 1H), 8.37 (d, J=6.2 Hz, 1H), 7.68 (m, 1H), 7.63 (d, J=8.6 Hz, 1H), 7.50–7.60 (m, 2H), 7.03 (d, J=2.6 Hz, 1H), 6.95 (dd, J=2.6, 8.6 Hz, 1H), 6.71 (s, 1H), 4.87 (s, 2H), 4.56 (m, 4H), 3.86 (s, 3H).

EXAMPLE 19

Preparation of 2,2-Difluoro-2-(2-pyridyl)ethyl 3-[2,2-difluoro-2-(2-pyridyl-N-oxide)ethylamino]- 6-chloropyrazin-2-one-1-acetamide

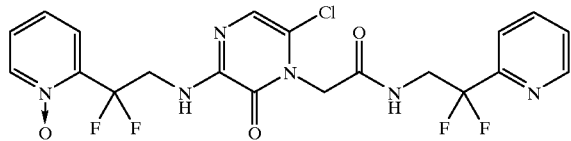

The title compound was prepared from 2,2-difluoro-2-(2-pyridyl)ethylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was further purified by preparative HPLC and characterized as the trifluoroacetate salt: $^1$H NMR (CD$_3$OD) δ8.64 (d, J=4.8 Hz, 1H), 8.38 (d, J=5.5 Hz, 1H), 7.98 (m, 1H), 7.70–7.74 (m, 2H), 7.51–7.60 (m, 3H), 6.69 (s, 1H), 4.78 (s, 2H), 4.56 (t, J=13.2 Hz, 2H), 4.09 (t, J=14.1 Hz, 2H).

EXAMPLE 20

Preparation of 3-Fluorophenethyl 3-[2,2-difluoro-2-(2-pyridyl-N-oxide)ethylamino]-6-chloropyrazin-2-one-1-acetamide

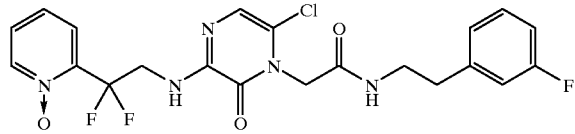

The title compound was prepared from 3-fluorophenethyl-amine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration, repeated washing with water and subsequent drying.: $^1$H NMR (CDCl$_3$) δ8.26 (d, J=6.6 Hz, 1H), 7.63 (m, 1H), 7.20–7.40 (m, 4H), 6.85–6.93 (m, 2H), 6.89 (s, 1H), 6.39 (br t, 1H), 5.80 (br t, 1H), 4.72 (s, 2H), 4.64 (td, J=7.1, 14.1 Hz, 2H), 3.52 (dd, J=6.4, 11.8 Hz, 2H), 2.82 (t, J=6.8 Hz, 2H).

EXAMPLE 21

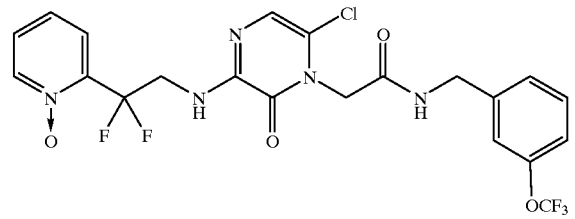

Preparation of 3-Trifluoromethoxybenzyl 3-[2,2-difluoro-2-(2-pyridyl-N-oxide)ethylamino]- 6-chloropyrazin-2-one-1-acetamide The title compound was prepared from 3-trifluoromethoxy-benzylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration, repeated washing with water and subsequent drying.: $^1$H NMR (CDCl$_3$) δ8.22 (d, J=6.6 Hz, 1H), 7.62 (dd, J=2.1, 7.8 Hz, 1H), 7.00–7.38 (m, 6H), 6.90 (s, 1H), 6.47 (br t, 1H), 6.27 (br t, 1H), 4.84 (s, 2H), 4.63 (td, J=6.8, 14.1 Hz, 2H), 4.49 (m, 2H).

EXAMPLE 22

Preparation of 2,2-Difluorophenethyl 3-[2,2-difluoro-2-(2-pyridyl-N-oxide)ethylamino]- 6-chloropyrazin-2-one-1-acetamide

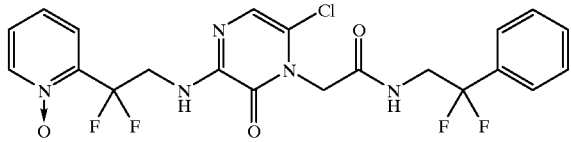

The title compound was prepared from 2,2-difluorophenethyl-amine and 3-[2,2-difluoro-2-(2-pyridyl-N-oxide)ethylamino]-6-chloropyrazin-2-one-2-acetic acid according to the modified general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: $^1$H NMR (CDCl$_3$) δ8.27 (d, J=6.2 Hz, 1H), 7.64 (dd, J=2.2, 7.9 Hz, 1H), 7.27–7.45 (m, 7H), 6.88 (s, 1H),), 6.55 (br t, 1H), 6.45 (br t, 1H), 4.79 (s, 2H), 4.64 (td, J=7.0, 14.1 Hz, 2H), 3.92 (td, J=6.2, 14.3 Hz, 2H).

EXAMPLE 23

Preparation of 2-(2,2,2-Trifluoroethoxy)-5-chlorobenzyl 3-[2,2-difluoro-2-(2-pyridyl -N-oxide) ethylamino]-6-chloropyrazin-2-one-1-acetamide

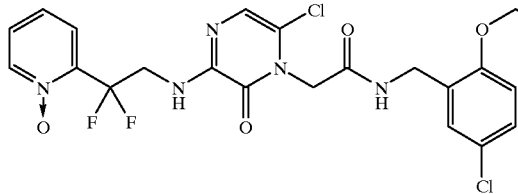

Step A
2-(2,2,2-Trifluoroethoxy)-5-chlorobenzaldehyde

To a solution of trifluoromethanesulfonyl chloride (25 g, 148 mmol) in methylene chloride (200 mL) at −78° C. was added sequentially and in a dropwise manner, trifluoroethanol (10 mL, 137 mmol) and triethylamine (21 mL, 151 mmol). The reaction mixture was left to stir for 1.5 hr following which it was allowed to warm to 0° C. and stirred there for 1 hr. The reaction mixture was diluted with ether and stirred for an additional 0.5 hr following which the triethylamine hydrochloride thus precipitated was filtered off. The filtrate was concentrated though not to dryness (product volatility) and diluted once more with ether. Following filtration to remove any precipitated solids, the filtrate was concentrated almost to dryness and the resulting material used directly.

Using a small volume of DMF, the trifluorethoxy triflate thus prepared was added to a mixture of 5-chlorosalicylaldehyde (5 g, 32 mmol) and cesium carbonate (21 g, 64 mmol) in DMF (50 mL) at room temperature. After stirring at room temperature overnight the solids were filtered off and the filtrate concentrated under reduced pressure. The residue was diluted with ether and washed well with water. Drying (Na$_2$SO$_4$) and concentration yielded the title compound as an oil: $^1$H NMR (CDCl$_3$) δ10.42 (s, 1H), 7.84 (dd, J=2.6 Hz, 1H), 7.54 (m, 1H), 6.93 (d, J=8.8 Hz, 1H), 4.48 (qd, J=1.5, 7.8 Hz, 2H).

Step B
2-(2,2,2-Trifluoroethoxy)-5-chlorobenzyl alcohol

Sodium borohydride (200 mg, 5.3 mmol) was added to a solution of 2-(2,2,2-trifluoroethoxy)-5-chlorobenzaldehyde (2 g, 8.4 mmol) in ethanol at room temperature. After stirring for 1 hr, the solvent was removed under reduced pressure. Aqueous ammonium chloride was added to the residue to destroy excess hydride following which the mixture was extracted with ethyl acetate. The organic extracts were washed with brine and then dried over sodium sulfate. Concentration yielded the title compound as an oil: $^1$H NMR (CDCl$_3$) δ7.41 (d, J=2.4 Hz, 1H), 7.25 (m, 1H), 6.77 (d, J=8.8 Hz, 1H), 4.73 (d, J=4.6 Hz, 2H), 4.40 (m, 2H).

Step C
2-(2,2,2-Trifluoroethoxy)-5-chlorobenzyl azide

To a solution of 2-(2,2,2-trifluoroethoxy)-5-chlorobenzyl alcohol (1.9 g, 7.9 mmol) in THF (20 mL) at 0° C. was added diphenyl phosphoryl azide (2.2 mL, 10.2 mmol) followed by DBU (1.5 mL, 10.0 mmol). The reaction mixture was allowed to warm to room temperature overnight following which the solvent was removed under reduced pressure. The residue was partitioned between ether and water and the organic layer dried over sodium sulfate. Filtration, concentration and purification by flash chromatography (19:1 hexane/ether) gave the azide as a white solid: $^1$H NMR (CDCl$_3$) δ7.31 (m, 2H), 6.82 (d, J=8.8 Hz, 1H), 4.40 (m, 4H).

Step D
2-(2,2,2-Trifluoroethoxy)-5-chlorobenzylamine

To a solution of 2-(2,2,2-trifluoroethoxy)-5-chlorobenzyl azide (1.76 g, 6.63 mmol) in THF (20 mL) was added triphenylphosphine (2 g, 7.63 mmol). After stirring at room temperature for 2 h, water (0.5 mL) was added and the reaction mixture then heated at 65° C. for 2 h. After cooling back to room temperature the solvents were removed under reduced pressure. Following azeotroping with benzene, the residue was dissolved in ether and treated with an excess of cold 1M HCl in ether. The hydrochloride salt of the title compound was filtered off and washed well with ether and dichloromethane. Drying gave a white powder: $^1$H NMR (CD$_3$OD) δ7.46 (m, 2H), 7.18 (d, J=8.4 Hz, 1H), 4.70 (q, J=8.4 Hz, 2H), 4.14 (s, 2H).

Step E
2-(2,2,2-Trifluoroethoxy)-5-chlorobenzyl 3-[2,2-difluoro-2-(2-pyridyl-N-oxide)ethylamino]- 6-chloropyrazin-2-one-1-acetamide The title compound was prepared from 2-(2,2,2-trifluoroethoxy)-5-chlorobenzylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: ¹H NMR (CD₃OD) δ8.60 (br t, 1H), 8.36 (d, J=5.9 Hz, 1H), 7.68 (m, 1H), 7.52–7.58 (m, 2H), 7.24–7.29 (m, 2H), 7.02 (d, J=8.4 Hz, 1H), 6.71 (s, 1H), 4.86 (s, 2H), 4.56 (m, 4H), 4.39 (m, 2H).

EXAMPLE 24

Preparation of 2-(2,2,2-Trifluoroethoxy)benzyl 3-[2, 2-difluoro-2-(2-pyridyl-N-oxide)ethylamino]-6-chloropyrazin-2-one-1-acetamide

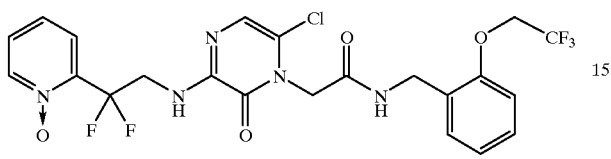

Step A 2-(2,2,2-Trifluoroethoxy)benzylamine

A solution of 2-(2,2,2-trifluoroethoxy)-5-chlorobenzylamine hydrochloride (650 mg) in ethanol (200 mL) containing 20% Pd(OH)₂/C (1 g) was hydrogenated at 50 psi for 4 h. The catalyst was removed via filtration through Celite and the filtrate then evaporated to dryness to give the title compound as a white powder: ¹H NMR (CD₃OD) δ7.47 (m, 2H), 7.19 (m, 2H), 4.69 (q, J=8.4 Hz, 2H), 4.16 (s, 2H).

Step B 2-(2,2,2-Trifluoroethoxy)benzyl 3-[2,2-difluoro-2-(2-pyridyl-N -oxide)ethylamino]-6-chloropyrazin-2-one-1-acetamide The title compound was prepared from 2-(2,2,2-trifluoroethoxy)-5-chlorobenzylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: ¹H NMR (CDCl₃) δ8.25 (d, J=6.4 Hz, 1H), 7.61 (dd, J=1.8, 7.9 Hz, 1H), 7.27–7.36 (m, 4H), 7.03 (t, J=7.5 Hz, 1H), 6.87 (s, 1H), 6.83 (d, J=8.2 Hz, 1H), 6.38 (br t, 1H), 6.25 (br t, 1H), 4.77 (s, 2H), 4.63 (qd, J=7.0, 13.9 Hz, 2H), 4.49 (d, J=6.0 Hz, 2H), 4.40 (q, J=8.1 Hz, 2H).

General Scheme

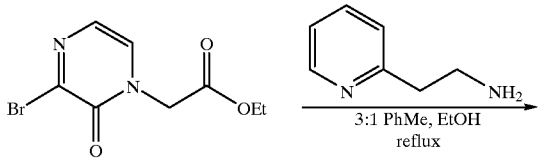

-continued

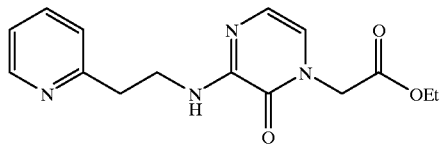

i) NCS, DCE, reflux
ii) MCPBA, Na₂CO₃
iii) KOH

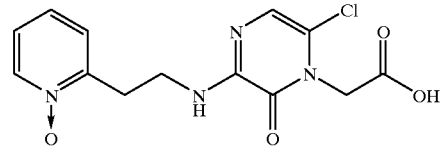

EDC, HOAt
ArCH₂NH₂

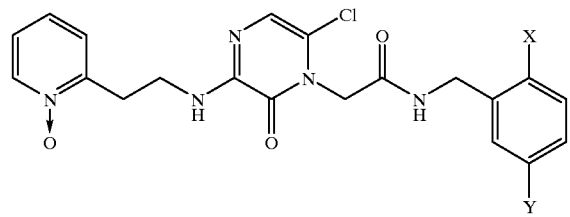

EXAMPLE 25

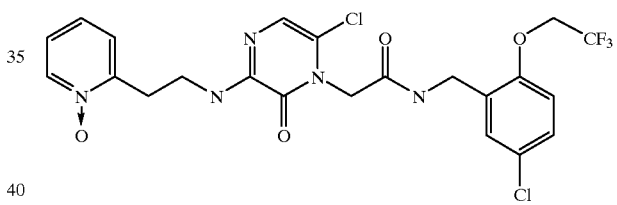

Preparation of 2-(2,2,2-Trifluoroethoxy)-5-chlorobenzyl 3-[2-(2-pyridyl-N-oxide)ethylamino]-6-chloropyrazin-2-one-1-acetamide Step A Ethyl 3-[2-(2-pyridyl)ethylamino]pyrazin2-one-1-acetate A solution of 2-aminoethylpyridine (3.14 mL, 28.5 mmol), ethyl 3-bromo-2-pyrazinone-1-acetate (4.96 g, 19.0 mmol) and triethylamine (2.65 mL, 19.0 mmol) in 3:1 toluene/ethanol was heated in a sealed tube at 120° C. overnight. The reaction mixture was cooled to room temperature and the solids filtered off. The filtrate was concentrated to dryness, combined with the solids and the mixture partitioned between 1:1 ethyl acetate/ether and saturated sodium bicarbonate. The aqueous phase was extracted with dichloromethane. The combined organic extracts were dried over sodium sulfate and concentrated to give a yellow brown solid. Purification by flash chromatography (19:1 to 9:1 chloroform/methanol) gave the title compound as a cream colored powder: ¹H NMR (CDCl₃) δ8.56 (d, J=4.6 Hz, 1H), 7.60 (td, J=1.5, 7.7 Hz, 1H), 7.18 (d, J=7.7 Hz, 1H), 7.14 (m, 1H), 6.88 (d, J=4.8 Hz, 1H), 6.61 (br t, 1H), 6.36 (d, J=4.6 Hz, 1H), 4.54 (s, 2H), 4.25 (q, J=7.2 Hz, 2H), 3.84 (q, J=6.6 Hz, 2H), 3.12 (t, J=6.6 Hz, 2H), 1.29 (t, J=7.2 Hz, 3H).

Step B
Ethyl 3-[2-(2-pyridyl)ethylamino]-6-chloropyrazin-2-one-1-acetate

A solution of ethyl 3-[2-(2-pyridyl)ethylamino]pyrazin-2-one-1-acetate (1.4 g, 4.63 mmol) and N-chlorosuccinimide (0.6 g, 4.49 mmol) in dichloroethane was heated at 70° C. overnight. The reaction mixture was cooled to room temperature and concentrated. The residue was purified by chromatography (1:4 hexane/EtOAc then EtOAc then 98:2 $CH_2Cl_2$/MeOH). The product was found to be contaminated by succinimide. This was removed by dissolving the product in ethyl acetate and washing with water and aqueous sodium bicarbonate. Drying (sodium sulfate) and concentration of the organic phase gave the product as a white solid: $^1$H NMR ($CDCl_3$) δ8.56 (d, J=4.9 Hz, 1H), 7.61 (t, J=7.8 Hz, 1H), 7.17 (d, J=7.8 Hz, 1H), 7.15 (m, 1H), 6.96 (s, 1H), 6.60 (br t, 1H), 4.88 (s, 2H), 4.25 (q, J=7.2 Hz, 2H), 3.83 (q, J=6.3 Hz, 2H), 3.12 (t, J=6.6 Hz, 2H), 1.30 (t, J=7.2 Hz, 3H).

Step C
Ethyl 3-[2-(2-pyridyl-N-oxide)ethylamino]-6-chloropyrazin-2-one-1-acetate m-Chloroperbenzoic acid (70–75%, 1.2 g, ~4.85 mmol) was added to a mixture of ethyl 3-[2-(2-pyridyl)ethylamino]-6-chloropyrazin-2-one-1-acetate (1.4 g, 4.2 mmol) in dichloroethane (30 mL) and 10% sodium carbonate (8 mL) at room temperature. After stirring for 24 h, the reaction mixture was diluted with EtOAc and washed with cold 10% sodium carbonate and then saturated sodium bicarbonate. Drying (sodium sulfate) and concentration gave the N-oxide as a powder. $^1$H NMR ($CDCl_3$) δ8.29 (d, J=5.3 Hz, 1H), 7.18–7.26 (m, 3H), 6.93 (s, 1H), 6.83 (br t, 1H), 4.88 (s, 2H), 4.25 (q, J=7.2 Hz, 2H), 3.84 (q, J=6.3 Hz, 2H), 3.12 (t, J=6.6 Hz, 2H), 1.30 (t, J=7.2 Hz, 3H).

Step D
3-[2-(2-Pyridyl-N-oxide)ethylamino]-6-chloropyrazin-2-one-1-acetic acid

A suspension of ethyl 3-[2-(2-pyridyl-N-oxide)ethylamino]-6-chloropyrazin-2-one-1-acetate (608 mg, 1.8 mmol) in 1:1 THF/methanol was treated with 1 M KOH (3 mL) whereupon a homogenous solution was obtained. The reaction mixture was stirred overnight then the methanol and THF was rotavaped off. 1 M HCl (3 mL) was added and the mixture evaporated to dryness and the resulting solid used directly: $^1$H NMR ($CD_3OD$) δ8.39 (d, J=6.4 Hz, 1H), 7.98 (m, 1H), 7.44–7.60 (m, 3H), 6.90 (s, 1H), 4.90 (s, 2H), 3.83 (t, J=6.4 Hz, 2H), 3.32 (t, J=6.4 Hz, 2H?, obscured by solvent peak).

Step E
2-(2,2,2-Trifluoroethoxy)-5-chlorobenzyl 3-[2-(2-pyridyl-N-oxide)ethylamino]-6-chloropyrazin-2-one-1-acetamide The title compound was prepared from 2-(2,2,2-trifluoroethoxy)-5-chlorobenzylamine and 3-[2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: $^1$H NMR ($CD_3OD$) δ8.59 (d, J=6.4 Hz, 1H), 7.63–7.85 (m, 3H), 7.27–7.30 (m, 2H), 7.05 (d, J=8.6 Hz, 1H), 7.03 (s, 1H), 4.97 (s, 2H), 4.61 (q, J=8.4 Hz, 2H), 4.44 (s, 2H), 3.88 (t, J=6.8 Hz, 2H), 3.42 (t, J=6.8 Hz, 2H).

EXAMPLE 26

Preparation of 2-Methyl-5-chlorobenzyl 3-[2-(2-pyridyl-N-oxide)ethylamino]-6-chloropyrazin-2-one-1-acetamide

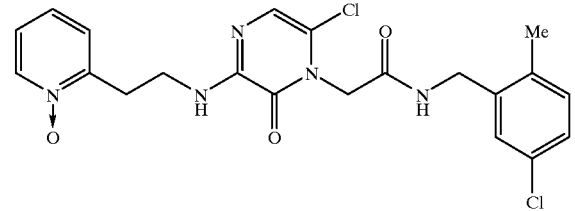

Step A

2-Methyl-5-chlorobenzylamine

A solution of 2-methyl-5-chlorobenzonitrile (2 g, 13.2 mmol), in THF (30 mL) was cooled to −15° C. and treated with 1 M lithium aluminum hydride in THF (13.4 mL). The reaction mixture was allowed to warm gradually to 0° C. over 2 h and was then stirred at room temperature for 1.5 h. It was then cooled to 0° C. and quenched sequentially with EtOAc (1 mL), water (0,5 mL), 15% NaOH (0.5 mL), and water (1.5 mL). After stirring for 1 h, the solids were removed via filtration. The filtrate was concentrated and the resulting residue purified by flash chromatography (98:2 methylene chloride/methanol) to give the product as an oil: $^1$H NMR ($CDCl_3$) δ7.33 (d, J=2.0 Hz, 1H), 7.08 (m, 2H),, 3.83 (s, 2H),, 2.28 (s, 3H), 1.42 (br s, 2H).

Step B

2-Methyl-5-chlorobenzyl 3-[2-(2-pyridyl-N-oxide)ethylamino-6-chloropyrazin-2-one-1-acetamide The title compound was prepared from 2-methyl-5-chlorobenzylamine and 3-[2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.:

$^1$H NMR ($CD_3OD$) δ8.60 (d, J=6.4 Hz, 1H), 7.65–7.88 (m, 3H), 7.27 (s, 1H), 7.17 (s, 2H), 7.04 (s, 1H), 4.95 (s, 2H), 4.41 (s, 2H), 3.88 (t, J=6.8 Hz, 2H), 3.43 (t, J=6.8 Hz, 2H), 2.31 (s, 3H).

EXAMPLE 27

Preparation of 2-Methyl-5-chlorobenzyl 3-[2,2-difluoro-2-(2-pyridyl-N-oxide)ethylamino]- 6-chloropyrazin-2-one-1-acetamide

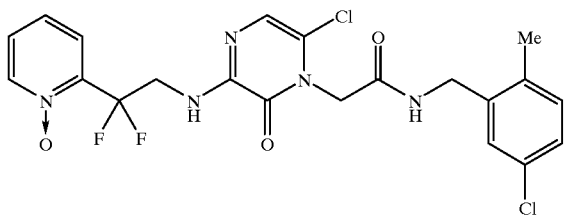

The title compound was prepared from 2-methyl-5-chloro-benzylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration, repeated washing with water and subsequent drying.: $^1$H NMR (CDCl$_3$) δ8.22 (d, J=6.6 Hz, 1H), 7.62 (d, J=7.8 Hz, 1H), 7.11–7.37 (m, 5H), 6.91 (s, 1H), 6.47 (br t, 1H), 6.09 (br t, 1H), 4.84 (s, 2H), 4.62 (td, J=6.8, 14.1 Hz, 2H), 4.44 (d, J=4.8 Hz, 2H), 2.26 (s, 3H).

EXAMPLE 28

Preparation of 2-Trifluoromethoxybenzyl 3-[2,2-difluoro-2-(2-pyridyl-N-oxide)ethylamino]-6-chloropyrazin-2-one-1-acetamide

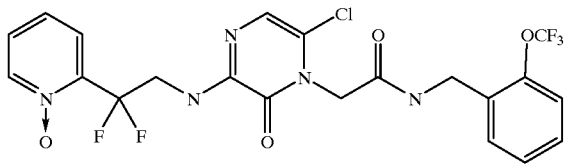

The title compound was prepared from 2-trifluoromethoxybenzylamine and 3-[2,2-difluoro-2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: $^1$H NMR (CD$_3$OD) δ8.56 (d, J=5.4 Hz, 1H), 7.75–7.95 (m, 3H), 7.29–7.47 (m, 4H), 7.03 (s, 1H), 4.94 (s, 2H), 4.67 (t, J=13.9 Hz, 2H), 4.50 (s, 2H).

EXAMPLE 29

Preparation of 2,5-Dichlorobenzyl 3-[2-(2-pyridyl-N-oxide)ethylamino]-6-chloropyrazin-2-one-1-acetamide

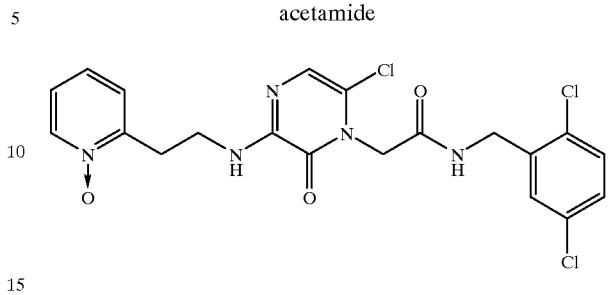

The title compound was prepared from 2,5-dichlorobenzyl-amine and 3-[2-(2-pyridyl-N-oxide)ethylamino]-6-chloropyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: $^1$H NMR (CD$_3$OD) δ8.63 (d, J=6.6 Hz, 1H), 7.80–7.93 (m, 2H), 7.69 (m, 1H), 7.41 (m, 2H), 7.32 (m, 1H), 7.04 (s, 1H), 4.98 (s, 2H), 4.49 (s, 2H), 3.89 (t, J=6.8 Hz, 2H), 3.44 (t, J=6.8 Hz, 2H).

EXAMPLE 30

Preparation of 2-(2,2,2-Trifluoroethoxy)-5-chlorobenzyl 3-[2,2-difluoro-2-(2-pyridyl-N-oxide) ethylamino]pyrazin- 2-one-1-acetamide

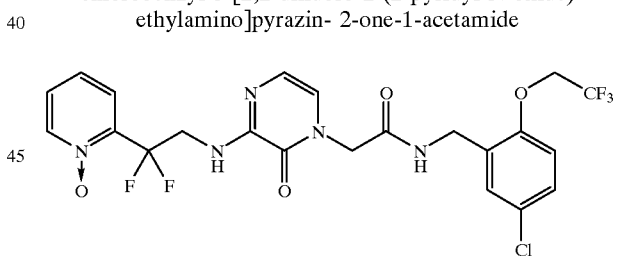

Step A
3-[2,2-Difluoro-2-(2-pyridyl-N-oxide)ethylamino]pyrazin-2-one-1-acetic acid A suspension of ethyl 3-[2,2-Difluoro-2-(2-pyridyl-N-oxide)ethylamino]pyrazin-2-one-1-acetate (85 mg, 0.24 mmol) in 1:1 THF/methanol (4 mL) was treated with 1 M KOH (0.3 mL) whereupon a homogenous solution was obtained. The reaction mixture was stirred overnight then the methanol and THF was rotavaped off. 1 M HCl (0.3 mL) was added and the mixture evaporated to dryness and the resulting solid used directly.
Step B
2-(2,2,2-Trifluoroethoxy)-5-chlorobenzyl 3-[2,2-difluoro-2-(2-pyridyl-N -oxide)ethylamino]pyrazin-2-one-1-acetamide The title compound wag prepared from 2-(2,2,2-trifluoroethoxy)-5-chlorobenzylamine and 3-[2,2-difluoro-2-(2-pyridyl-N-oxide)ethylamino]pyrazin-2-one-1-acetic acid according to the general EDC mediated coupling procedure. When conversion of the starting materials was complete, the DMF was removed under reduced pressure. The resulting residue was then stirred while water (which had been rendered mildly basic by the addition of 10% by volume of saturated sodium bicarbonate) was added. Stirring was continued until the product solidified whereupon it was collected via filtration and repeated washing with water. The product was allowed to dry and then it was added to a 1:1 mixture of EtOAc and MeCN. Addition of a 1 M solution of HCl in ether gave the hydrochloride which was then collected via filtration.: $^1$H NMR (CD$_3$OD) δ8.52 (m, 1H), 7.92 (m, 1H), 7.74 (m, 2H), 7.31 (m, 2H), 7.07 (d, J=5.7 Hz, 1H), 7.03 (d, J=8.8 Hz, 1H), 6.83 (d, J=5.7 Hz, 1H), 4.72 (s, 2H), 4.60 (q, J=8.4 Hz, 2H), 4.43 (s, 2H).

EXAMPLE 31

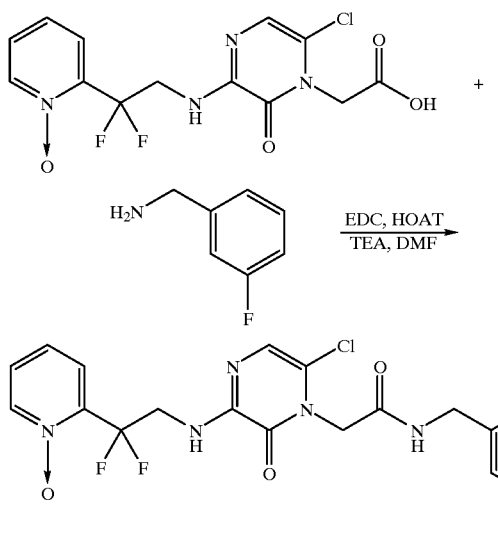

3-Fluorobenzyl 3-(2,2-difluoro-2-(2-pyridyl-N-oxide) ethylamino)-6-chloropyrazin-2-one-1-acetamide To a stirred solution of 90 mg (0.125 mmol, 50% by weight) of 3-(2,2-difluoro-2-(2-pyridyl-N-oxide) ethylamino)-6-chloropyrazin(1H)-2-one-1-acetic acid and 22 μL (0. 19 mmol) 3-fluorobenzylamine in 1 mL of DMF was added 36 mg (0. 19 mmol) of EDC, 20 mg (0. 15 mmol) of HOAT and 0.52 mL (0.375 mmol) triethylamine. After stirring for 3d, the volatiles were removed en vacuo. The residue was diluted with sat. aq. NaHCO$_3$, filtered, and rinsed with water to afford a gummy solid. This material was triturated with CH$_2$Cl$_2$ (2 mL) to give a white solid, which was suspended in MeOH and treated with ~1 mL of 2.6M HCl in EtOAc. Concentration afforded the title compound as a solid: $^1$H NMR (CD$_3$OD) δ8.60 (d, 1H, 5.4 Hz), 7.98 (d, 1H, 6.6 Hz), 7.82 (m, 2H), 7.35 (ddd, 1H, 7.2 Hz), 7.14 (d, 1H, 7.6 Hz), 7.07 (s, 1H), 7.05 (m, 1H), 7.00 (ddd, 1H, 2.2, 8.5, 8.5 Hz), 4.96 (s, 2H), 4.71 (t, 2H, 13.9 Hz). 4.45 (s, 2H).

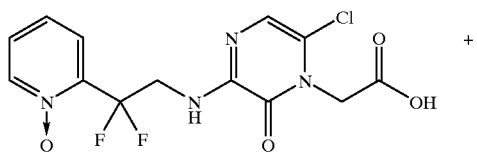

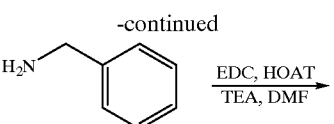

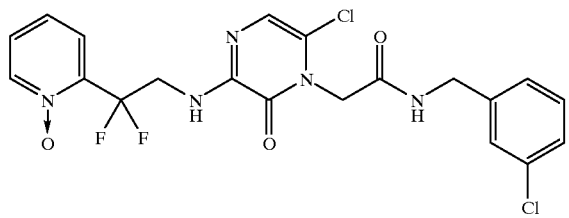

3-Chlorobenzyl 3-(2,2-difluoro-2-(2-pyridyl-N-oxide) ethylamino)-6-chloropyrazin-2-one-1-acetamide To a stirred solution of 90 mg (0.125 mmol, 50% by weight) of 3-(2,2-difluoro-2-(2-pyridyl-N-oxide) ethylamino)-6-chloropyrazin(1H)-2-one-1-acetic acid and 23 μL (0.19 mmol) 3-chlorobenzylamine in 1 mL of DMF was added 36 mg (0.19 mmol) of EDC, 20 mg (0.15 mmol) of HOAT and 0.52 mL (0.375 mmol) triethylamine. After stirring for 3d, the volatiles were removed en vacuo. The residue was diluted with sat. aq. NaHCO$_3$, filtered, and rinsed with water to afford a gummy solid. This material was triturated with CH$_2$Cl$_2$ (2 mL) to give a white solid, which was suspended in MeOH and treated with ~1 mL of 2.6M HCl in EtOAc. Concentration afforded the title compound as a solid: $^1$H NMR (CD$_3$OD) δ8.61 (d, 1H, 5.9 Hz), 7.97 (dd, 1H, 1.6, 7.6 Hz), 7.86–7.79 (m, 2H), 7.34–7.24 (m, 4H), 7.07 (s, 1H), 4.96 (s, 2H), 4.71 (t, 2H, 14.0 Hz). 4.43 (s, 2H).

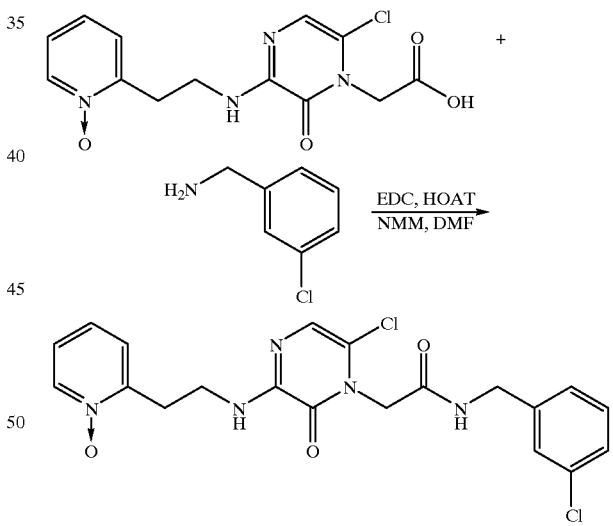

3-Chlorobenzyl 3-(2-(2-pyridyl-N-oxide)ethylamino)-6-chloropyrazin-2-one-1-acetamide To a stirred solution of 60 mg (0.133 mmol, 72% by weight) of 3-(2-(2-pyridyl-N-oxide)ethylamino)-6-chloropyrazin(1H)-2-one-1-acetic acid and 25 μL (0.20 mmol) 3-chlorobenzylamine in 1 mL of DMF was added 38 mg (0.20 mmol) of EDC, 20 mg (0.15 mmol) of HOAT and 0.60 mL (0.532 mmol) N-methylmorpholine. After stirring for 1d, the volatiles were removed en vacuo. The residue was diluted with sat. aq. NaHCO$_3$, filtered, and rinsed with water to afford a solid. This material was purified by flash chromatography with 2–10% MeOH:CH$_2$Cl$_2$ (with 0.5%

NH$_4$OH) to give a solid, which was suspended in MeOH and treated with ~1 mL of 2.6M HCl in EtOAc. Concentration afforded the title compound as a white solid: $^1$H NMR (CD$_3$OD) δ8.59 (d, 1H, 6.5 Hz), 7.85–7.76 (m, 2H), 7.66 (ddd, 1H, 1.8, 7.0, 7.0 Hz), 7.35–7.25 (m, 4H), 7.05 (s, 1H), 4.97 (s, 2H), 4.44 (s, 2H), 3.89 (t, 2H, 6.8 Hz). 3.43 (t, 2H, 6.8 Hz).

EXAMPLE 32

Preparation of 3-Chloro-2-pyridylmethyl 3-(2,2-difluoro-2-(2-pyridyl-N-oxide)ethylamino)-6-chloropyrazin-2-one-1-acetamide

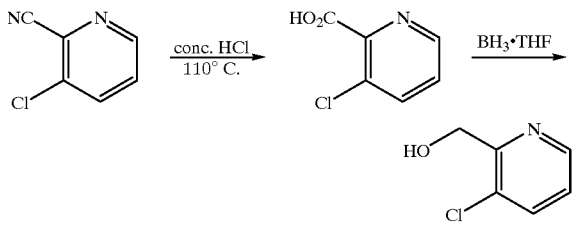

3-Chloro-2-(hydroxymethyl)pyridine

A stirred solution of 3.31 g (24.0 mmol) of 3-chloro-2-cyanopyridine (Sakamoto et al., Chem. Pharm. Bull. 33(2) 565–571 (1985)) and 50 mL of conc. HCl were heated at 110° C. for 24 h. Concentration and trituration with acetonitrile afforded the carboxylic acid as an off white solid. To a 0° C. suspension of 3.0 g (ca. 18.9 mmol) of this crude material in 100 mL of THF, was added 25 mL (25.0 mmol) of borane (1M in THF). After 2 d at room temperature, conc. HCl was carefully added until gas evolution subsided. After 20 min of additional stirring the reaction was concentrated, diluted with aq. NaOH and extracted with CH$_2$Cl$_2$ (4×). The combined organic extracts were dried were dried (MgSO$_4$) and concentrated to a yellow oil. The resultant crude residue was chromatographed on SiO$_2$ using 60:40 EtOAc-hexanes to afford the title compound: $^1$H NMR (CDCl$_3$) δ8.49 (d, 1H, 4.6 Hz), 7.69 (dd, 1H, 1.2, 8.0 Hz), 7.23 (dd, 1H, 4.8, 7.9 Hz), 4.80 (d, 2H, 4.6 Hz), 4.33 (t, 1H, 4.6 Hz).

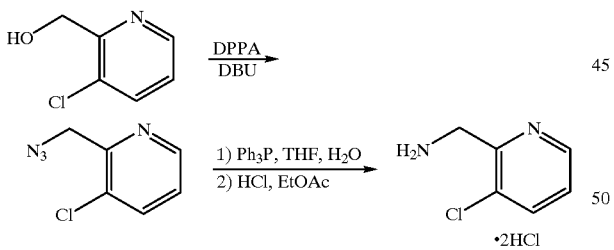

2-Aminomethyl-3-chloropyridine dihydrochloride

To a 0° C. solution of 738 mg (5.16 mmol) of 3-chloro-2-(hydroxymethyl)pyridine in 10 mL of toluene, was added 2.13 g (7.74 mmol) of diphenylphosphoryl azide followed by 1.18 g (7.74 mmol) of DBU. After stirring at room temperature overnight, the reaction was partitioned between EtOAc and sat. aq. NaHCO$_3$. The organic layer was separated and the aqueous phase was washed with EtOAc (3×). The combined organic extracts were dried (MgSO$_4$) and concentrated to a dark oil. This resultant crude residue was chromatographed on SiO$_2$ using 10:90 EtOAc-hexanes to afford the title compound contaminated with an aromatic impurity. Triphenylphosphine (1.63 g, 6.20 mmol) was added to a solution of the crude azide in THF:H$_2$O (10:0.5 mL). After stirring overnight, the reaction was concentrated. This residue was diluted with EtOAc, and HCl (2.6M in ]EtOAc) was added dropwise to precipitate out the amine hydrochloride. Stirring was continued for 20 min, after which time the mixture was filtered and rinsed with EtOAc to afford the title compound as a white solid: $^1$H NMR (CD$_3$OD) δ8.57 (d, 1H, 4.7 Hz), 7.94 (d, 1H, 8.1 Hz), 7.44 (dd, 1H, 4.7, 8.0 Hz), 4.40 (s, 2 Hz).

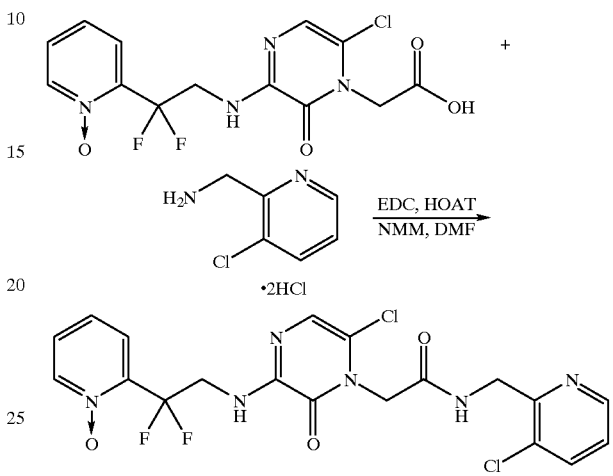

3-Chloro-2-pyridylmethyl 3-(2,2-difluoro-2-(2-pyridyl-N-oxide)ethylamino)-6-chloropyrazin-2-one-1-acetamide A stirred solution of 459 mg (1.28 mmol) of 3-(2,2-difluoro-2-(2-pyridyl-N-oxide)ethylamino)-6-chloropyrazin (1H)-2-one-1-acetic acid and 409 mg (1.91 mmol) 2-aminomethyl-3-chloropyridine dihydrochloride in 10 mL of DMF was added 364 mg (1.9 mmol) of EDC, 258 mg (1.9 mmol) of HOAT and 1.0 mL N-methylmorpholine. After stirring overnight, the volatiles were removed en vacuo. The residue was diluted with water, filtered, and rinsed with water to afford a solid. This material was suspended in MeOH and treated with conc. HCl until the solution became homogeneous. Concentration afforded the product as a white solid: $^1$H NMR (CD$_3$OD) δ8.77 (dd, 1H, 1.1, 5.1 Hz), 8.65 (dd, 1H, 1.1, 8.3 Hz), 8.56 (br d, 1H, 6.3 Hz), 7.98 (dd, 1H, 5.7, 8.3 Hz), 7.92 (dd, 1H, 2.2, 7.6 Hz), 7.82–7.75 (m, 2H), 6.99 (s, 1H), 4.99 (s, 2H), 4.81 (s, 2H), 4.65 (t, 2H, 13.9 Hz).

EXAMPLE 33

Preparation of 3-(Methylsulfonyl)-2-pyridylmethyl-3-(2,2-difluoro-2-(2-pyridyl-N-oxide)ethylamino)-6-chloropyrazin-2-one-1-acetamide trifluoroacetate

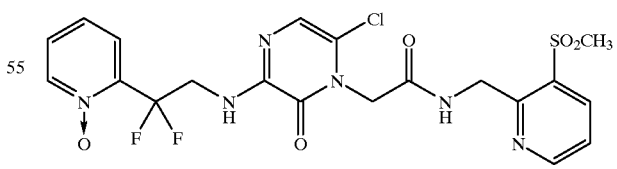

Step A
N-Phthalimido-3-(methylthio)pyridyl-2-methylamine

To a solution of 3-(methylthio)pyridyl-2-methylamine dihydrochloride (Example 10, Step B, 227 mg, 1.00 mmol) and sodium carbonate (318 mg, 3.00 mmol) in water (8.5 mL) was added N-carbethoxyphthalimide (241 mg, 1.10 mmol). The mixture was stirred at room temperature for 1 h and was then filtered. The solid residue was washed with water and dried on a high vacuum line to yield the title compound as a white solid:

$^1$H NMR (CDCl$_3$, 300 MHz): δ8.19 (dd, J=4.8, 1.4 Hz, 1H), 7.91–7.87 (m, 2H), 7.76–7.71 (m, 2H), 7.54 (dd, J=7.8, 1.4 Hz, 1H), 7.13 (dd, J=7.8, 4.8 Hz, 1H), 5.05 (s, 2H), 2.53 (s, 3H).

Step B
N-Phthalimido-3-(methylsulfoxy)pyridyl-2-methylamine

N-Phthalimido-3-(methylthio)pyridyl-2-methylamine was oxidized according to the procedure of Example 11. The crude product was purified by silica gel chromatography (gradient elution with 60% EtOAc-hexanes to 100% EtOAc to 5% MeOH—CHCl$_3$) to afford the title compound as a mixture of enantiomers which were inseparable by chiral HPLC:

$^1$H NMR (CDCl$_3$, 300 MHz): δ8.56 (dd, J=4.8, 1.5 Hz, 1H), 8.34 (dd, J=7.8, 1.5 Hz, 1H), 7.91–7.88 (m, 2H), 7.77–7.74 (m, 2H), 7.44 (dd, J=7.8, 4.7 Hz, 1H), 5.17 (d, J=15.9 Hz, 1H), 4.86 (d, J=15.9 Hz, 1H), 2.96 (s, 3H).

Step C
N-Phthalimido-3-(methylsulfonyl)pyridyl-2-methylamine

The title compound was prepared according to a procedure which was modified from that described in Giam, C. S.; Kikukawa, K.; Trujillo, D. A.; *Org. Prep. Proced. Int.* 1981, 13 (2), 137–140 as follows: A mixture of sodium tungstate dihydrate (14 mg, 0.042 mmol), water (4 mL), and acetic acid (1 drop) was heated to reflux for 10 min. After cooling to room temperature, 25 μL of the resulting solution was added to 3-(methylsulfoxy)-2-(phthalimidomethyl)pyridine (59 mg, 0.196 mmol) in 1,2-dichloroethane (250 μL). Hydrogen peroxide (50% in water, 12 μL, 0.398 mmol) was added to the mixture, which was then heated to reflux for 2.5 h. The DCE was removed in vacuo, and the resulting residue was taken up in water. Ammonium hydroxide and sodium bisulfite were added in minimal amounts to destroy residual hydrogen peroxide. The aqueous mixture was extracted with CHCl$_3$ (×3) and the organic layers were combined and dried over Na$_2$SO$_4$. The solvent was removed in vacuo to afford the title compound as a white, flaky solid:

$^1$H NMR (CDCl$_3$, 300 MHz): δ8.65 (dd, J=4.5, 1.5 Hz, 1H), 8.32 (dd, J=7.8, 1.5 Hz, 1H), 7.90 (dd, J=5.4, 3.0 Hz, 2H), 7.76 (dd, J=5.4, 3.0 Hz, 2H), 7.40 (dd, J=7.8, 4.8 Hz, 1H), 5.41 (s, 2H), 3.37 (s, 3H). MS (FAB) M+H; 317.2.

Step D
2-Aminomethyl-3-(methylsulfonyl)pyridine

To a mixture of N-phthalimido-3-(methylsulfonyl)pyridyl-2-methylamine (50 mg, 0.16 mmol) in ethanol (1 mL) at room temperature was added hydrazine hydrate (7.7 μL, 0.16 mmol). The mixture was heated to reflux for 1 h and the reaction was then quenched with 12 N hydrochloric acid (12 μL, 0.16 mmol). The ethanol was removed in vacuo, and the solid residue was taken up in 1 M hydrochloric acid and heated to 50° C. for 10 min. The mixture was cooled to room temperature and was filtered and washed with 1 M hydrochloric acid. The aqueous filtrate was then washed with two volumes of CH$_2$Cl$_2$ and concentrated in vacuo to half the volume. Triethylamine was added to pH 8, and the solution was concentrated in vacuo to dryness. The residue was purified by silica gel chromatography (isocratic elution with 8:1:1 ethyl acetate:ammonium hydroxide:methanol) to afford the title compound as a pink oil:

$^1$H NMR (CD$_3$OD, 300 MHz): δ8.84–8.23 (m, 1H), 8.37–8.35 (m, 1H), 7.58–7.55 (m, 1H), 4.32 (s, 2H), 3.25 (s, 3H), 4.87. MS (FAB) M+H: 187.0.

Step E
3-(Methylsulfonyl)-2-pyridylmethyl-3-(2,2-difluoro-2-(2-pyridyl-N-oxide)ethylamino)-6-chloropyrazin-2-one-1-acetamide trifluoroacetate To a mixture of 3-(2,2-difluoro-2-(2-pyridyl-N-oxide) ethylamino)-6-chloropyrazin-2-one-1-carboxylic acid (42.2 mg, 0.117 mmol), 2-(aminomethyl)-3-(methylsulfonyl) pyridine (21.7 mg, 0.117 mmol), and HOAT (8.1 mg, 0.059 mmol) in DMF (1 mL) was added EDC (33.7 mg, 0.176 mmol). The mixture was stirred at room temperature for 18 h. The crude reaction mixture was purified directly by reverse phase HPLC (gradient elution with 95:5 water/0.1% trifluoroacetic acid:acetonitrile/0.1% trifluoroacetic acid to 5:95 water/0.1% trifluoroacetic acid:acetonitrile/0.1% trifluoroacetic acid) to afford the title compound as a white powder:

$^1$H NMR (CD$_3$OD, 300 MHz): δ8.80 (dd, J=4.8, 1.5 Hz, 1H), 8.37–8.33 (br m, 2H), 7.68–7.67 (m, 1H), 7.58–7.53 (br m, 3H), 6.68 (s, 1H), 4.91 (s, 2H), 4.86 (s, 2H), 4.55 (t, J=13.1 Hz, 2H), 3.30 (s, 3H). HRMS (FAB) M+H: 529.0880.

EXAMPLE 34

Preparation of 2-(Ethylthio)benzyl-3-(2,2-difluoro-2-(2-pyridyl-N-oxide)ethylamino)-6-chloropyrazin-2-one-1-acetamide

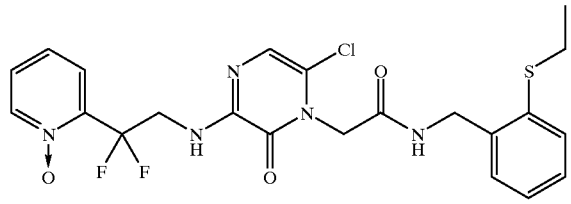

Step A
Methyl-2-(ethylthio)benzoate

The title compound was prepared according to the procedure described in Abe, H.; Fujii, H.; Masunari, C.; Itani, J.; Kashino, S. *Chem. Pharm. Bull.* 1997, 45 (5), 778–785 and was isolated as a solid:

$^1$H NMR (CDCl$_3$, 300 MHz): δ7.96 (d, J=7.8, 1.5 Hz, 1H), 7.47–7.41 (m, 1H), 7.33–7.30 (m, 1H), 7.18–7.12 (m, 1H), 3.92 (s, 3H), 2.96 (q, J=7.2 Hz, 2H), 1.39 (t, J=7.2 Hz, 3H).

Step B
2-(Ethylthio)benzyl alcohol

A solution of methyl-2-(ethylthio)benzoate (5.0 g, 25.5 mmol) in dry THF (67 mL) was added to a stirred solution of LAH (17.5 mL of a 1.0 M solution in THF) in an additional 50 mL dry THF at 0° C. under Ar. The reaction was allowed to warm to room temperature while stirring overnight. The resulting clear solution was diluted with EtOAc (140 mL). The mixture was poured into water (300 mL) and the resulting precipitate was filtered off. The filtrate was extracted with ether (3×200 mL) and the combined organic extracts were dried over MgSO$_4$, filtered, concentrated in vacuo and dried overnight on a high vacuum line to yield the title compound as a pale yellow oil:

$^1$H NMR (CDCl$_3$, 300 MHz): δ7.40–7.18 (br m, 4H), 4.78 (d, J=6.3 Hz, 2H), 2.96 (q, J=7.5 Hz, 2H), 2.22 (t, J=6.2 Hz, 1H), 1.34–1.29 (m, 3H). HRMS (ES) M+NH$_4$$^+$: 186.0942.

Step C
2-(Azidomethyl)-ethylthiobenzene

To a stirred solution of 2-(ethylthio)benzyl alcohol (3.98 g, 23.6 mmol) in THF (48 mL) at 0° C. under Ar was added DPPA (6.1 mL, 28.4 mmol) followed by DBU (4.0 mL, 26.0 mmol). The reaction was allowed to warm to room temperature and stirred for 2 days. The solution was concentrated to an oil, which was taken up in EtOAc, and washed successively with 10% aqueous citric acid, saturated aqueous NaHCO$_3$ solution and brine. The organic layer was dried over Na$_2$SO$_4$ and concentrated to an oil which was purified by silica gel chromatography (gradient elution with 100% hexanes to 5% EtOAc-hexanes). Concentration of the product fractions at reduced pressure afforded a pale yellow oil which was dried on a high vacuum line overnight to afford the title compound:

$^1$H NMR (CDCl$_3$, 300 MHz): δ7.42–7.19 (m, 4H), 4.52 (s, 2H), 2.95 (q, J=7.2 Hz, 2H), 1.32 (t, J=7.2 Hz, 3H). HRMS (ES) M+NH$_4^+$: 211.1006.

Step D 2-(Aminomethyl)-ethylthiobenzene hydrochloride

To a solution of 2-(azidomethyl)-ethylthiobenzene (3.57 g, 18.4 mmol) in THF (393 mL) was added triphenylphosphine (9.69 g, 36.9 mmol) and water (0.77 mL). The mixture was stirred overnight at room temperature. An additional 1.0 mL water was added and the mixture was heated to 60° C. After 4 h at 60° C., an additional 2.0 mL water was added and the mixture was heated to reflux overnight. The solution was concentrated to a pale yellow oil which was taken up in CH$_2$Cl$_2$. HCl gas was bubbled through the solution for approximately 10 min. The resulting precipitate was collected by filtration and dried on a high vacuum line to give the title compound as a white fluffy solid:

$^1$H NMR (CD$_3$OD): δ7.56–7.54 (m, 1H), 7.45–7.43 (m, 2H), 7.34–7.32 (m, 1H), 4.28 (m, 2H), 3.04–2.98 (m, 2H), 1.33–1.29 (m, 3H). MS (ES) M+H: 168.5

Step E 2-(Ethylthio)benzyl-3-(2,2-difluoro-2-(2-pyridyl-N-oxide)ethylamino)-6-chloropyrazin-2-one-1-acetamide The title compound was prepared according to the EDC coupling procedure which was described in Example 33, Step E (with one equivalent Et$_3$N added to the reaction mixture), and the free base was isolated as an off-white solid:

$^1$H NMR (CD$_3$OD): δ8.36 (d, J=6.4 Hz, 1H), 7.70–7.67 (m, 1H), 7.57–7.54 (m, 2H), 7.39 (d, J=7.6 Hz, 1H), 7.30 (d, J=7.6 Hz, 1H), 7.26–7.23 (m, 1H), 7.22–7.16 (m, 1H), 6.69 (s, 1H), 4.85 (m, 2H), 4.55 (t, J=13.2 Hz, 2H), 4.50 (s, 2H), 2.94 (q, J=7.2 Hz, 2H), 1.28 (t, J=7.2 Hz, 3H). HRMS (ES) M+H: 510.1159.

EXAMPLE 35

Preparation of (+)- and (−)-2-(Ethylsulfoxy)benzyl-3-(2,2-difluoro-2-(2-pyridyl-N-oxide)ethylamino)-6-chloropyrazin-2-one-1-acetamide trifluoroacetate

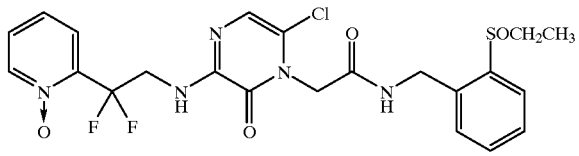

Step A 2-(Ethylthio)benzyltrifluoroacetamide

To a solution of 2-(aminomethyl)-ethylthiobenzene hydrochloride (500 mg, 2.46 mmol) and pyridine (0.50 mL, 6.15 mmol) in dry CH$_2$Cl$_2$ (21 mL) at 0° C. under Ar was added rapidly dropwise trifluoroacetic anhydride (0.45 mL, 3.2 mmol). The mixture was allowed to warm to room temperature while stirring overnight. The solution was diluted with CH$_2$Cl$_2$ (50 mL) and washed with 10% aqueous citric acid (100 mL). The aqueous layer was extracted with an additional 50 mL CH$_2$Cl$_2$. The combined organic extracts were washed with aqueous saturated NaHCO$_3$ (50 mL) and brine (50 mL). The organic layer was dried over MgSO$_4$ and concentrated at reduced pressure. Silica gel chromatography (isocratic elution with 20%/o EtOAc/hexanes) afforded the title compound as a white solid:

$^1$H NMR (CDCl$_3$, 300 MHz): δ7.40–7.18 (m, 4H), 6.85 (br s, 1H), 4.63 (d, J=6.0 Hz, 2H), 2.98 (q, J=7.2 Hz, 2H), 1.33 (t, J=7.2 Hz, 3H).

Step B (+)- and (−)-2-(Ethylsulfoxy)benzyltrifluoroacetamide

To a stirred solution of 2-(ethylthio)benzyltrifluoroacetamide (300 mg, 1.16 mmol) in CH$_2$Cl$_2$ (20 mL) at room temperature was added in portions MCPBA (75%, 280 mg, 1.22 mmol). The reaction was monitored by thin layer chromatography (70% EtOAc-hexanes eluent) and when complete was diluted to a volume of 50 mL with CH$_2$Cl$_2$ and was washed with aqueous saturated NaHCO$_3$ (2×30 mL). The aqueous washes were further extracted with CH$_2$Cl$_2$ (20 mL). The combined organic extracts were dried over MgSO$_4$ and concentrated at reduced pressure. Silica gel chromatography (70%EtOAc-hexanes) afforded a racemic mixture of the sulfoxide enantiomers as a colorless oil which was dried on a high vacuum line.

$^1$H NMR (CDCl): δ8.1 (br s, 1H), 7.57–7.44 (m, 4H), 4.76–4.66 (m, 2H), 3.02–2.88 (m, 2H), 1.28 (t, J=7.6 Hz, 3H). HRMS (ES) M+H: 280.0593.

The racemic 2-(ethylsulfoxy)benzyltrifluoroacetamide was resolved into pure enantiomers via chiral HPLC under the following conditions: Chiralpak AS column eluting with an 85:5:10 mixture of 0.2% diethylamine-hexane:isopropanol:methanol. The enantiomers were isolated as colorless oils and carried on directly to the deprotection step (this example, Step C).

Step C (+)- and (−)-2-(Ethylsulfoxy)benzylamine

A degassed mixture of the faster-moving enantiomer of 2-(ethylsulfoxy)benzyltrifluoroacetamide (110 mg, 0.395 mmol), potassium carbonate (164 mg, 1.19 mmol) and water (0.9 mL) in methanol (13.2 mL) was heated at 65° C. overnight. Silica gel was added to the crude mixture and the solvent was removed at reduced pressure. The residual powder was loaded onto a pre-packed silica gel column and the product was eluted with 9:0.9:0.1 CHCl$_3$—MeOH—NH$_4$OH. The product fractions were combined, concentrated at reduced pressure and dried on a high vacuum line to afford the title compound as a pale yellow oil:

$^1$H NMR (CDCl$_3$): δ7.96 (dd, J=7.2, 1.6 Hz, 1H), 7.52–7.40 (m, 3H), 4.03 (d, J=14.0 Hz, 1H), 3.90 (d, J=14.0 Hz, 1H), 3.11–3.02 (m, 1H), 2.89–2.80 (m, 1H), 1.30–1.26 (m, 3H). MS (ES) M+H: 184.4

The slower-moving enantiomer of 2-(ethylsulfoxy)benzyltrifluoroacetamide was deprotected in similar fashion to afford the title compound as a pale orange oil (sample contains significant amount of water by $^1$H NMR):

$^1$H NMR (CDCl$_3$): δ7.78–7.76 (m, 1H), 7.52–7.46 (m, 3H), 4.18–4.08 (m, 2H), 3.08–2.92 (m, 2H), 1.32–1.26 (m, 3H). MS (ES) M+H: 184.5

Step E (+)- and (−)-2-(Ethylsulfoxy)benzyl-3-(2,2-difluoro-2-(2-pyridyl-N-oxide)ethylamino)-6-chloropyrazin-2-one-1-acetamide trifluoroacetate The enantiomers of the title compound were prepared separately according to the general EDC coupling procedure described in Example 33, Step E and were isolated as yellow solids:

Enantiomer A (from the amine prepared from the faster-moving isomer of 2-(ethylsulfoxy)

benzyltrifluoroacetamide): $^1$H NMR (CDCl$_3$): δ8.36 8.31 (m, 1H), 7.72–7.70 (m, 1H), 7.67–7.64 (m, 1H), 7.52–7.36 (br m, 5H), 6.99–6.95 (m, 1 H), 6.85 (s, 1H), 6.44–6.34 (m, 1H), 4.84–4.78 (m, 2H), 4.74–4.54 (br m, 4H), 2.93 (apparent q, J=7.2 Hz, 2H), 1.25 (t, J=6.8 Hz, 3H). MS (ES) M+H: 526.6.

Enantiomer B (from the amine prepared from the slower-moving isomer of 2-(ethylsulfoxy)benzyltrifluoroacetamide): $^1$H NMR (CDCl$_3$): δ8.40–8.38 (m, 1H), 7.74–7.69 (m, 2H), 7.52–7.44 (br m, 5H), 7.05 (t, J=5.2 Hz, 1H), 6.84 (s, 1H), 6.49 (m, 1H), 4.87–4.75 (m, 2H), 4.68–4.53 (br m, 4H), 2.99–2.92 (m, 2H), 1.25 (t, J=7.6 Hz, 3H). HRMS (ES) M+H: 526.1095.

EXAMPLE 36

Preparation of 2-(Ethylsulfonyl)benzyl-3-(2,2-difluoro-2-(2-pyridyl-N-oxide)ethylamino)-6-chloropyrazin-2-one-1-acetamide trifluoroacetate

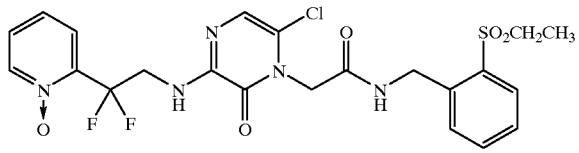

Step A
2-(Ethylsulfonyl)benzyltrifluoroacetamide

To a stirred solution of 2-(ethylthio)benzyltrifluoroacetamide (Example 35, Step A, 100 mg, 0.38 mmol) in CH$_2$Cl$_2$ (20 mL) was added in portions MCPBA (75%, 180 mg, 0.80 mmol). The mixture was stirred at room temperature for 1 h and was then diluted with CH$_2$Cl$_2$ and washed with saturated aqueous NaHCO$_3$ solution. The aqueous layer was further extracted with CH$_2$Cl$_2$ and the combined organic extracts were dried over MgSO$_4$ and concentrated in vacuo. The residue was purified by silica gel chromatography (isocratic elution with 35% EtOAc-hexanes) to afford the title compound as a colorless oil which was dried on a high vacuum line:

$^1$H NMR (CDCl): δ8.00 (d, J=7.6 Hz, 1H), 7.69–7.60 (m, 2H), 7.58–7.52 (m, 2 H), 4.76 (d, J=6.8 Hz, 2H), 3.19 (q, J=7.6 Hz, 2H), 1.34 (t, J=7.6 Hz). HRMS (ES) M+H: 296.0565.

Step B
2-(Ethylsulfonyl)benzylamine hydrochloride

To a stirred solution of 2-(ethylsulfonyl)benzyltrifluoroacetamide (88 mg, 0.30 mmol) in methanol (11 mL) and water (0.74 mL) was added potassium carbonate (124 mg, 0.90 mmol). The mixture was heated to 65° C. and stirred under Ar overnight. The mixture was then concentrated to a colorless oil which was taken up in EtOAc and washed with a small amount of brine. The aqueous layer was extracted twice with CHCl$_3$ and was then saturated with sodium chloride and further extracted with THF. The combined organic extracts were dried over MgSO$_4$ and concentrated at reduced pressure. The residue was treated with 2 equivalents of 1.0 M HCl in ether. The resulting precipitate was collected by filtration and was dried on a high vacuum line to give the title compound as an off-white solid:

$^1$H NMR (CD$_3$OD): δ8.09 (d, J=7.8 Hz, 1H), 7.84–7.70 (br m, 3H), 4.46 (s, 2H), 3.38–3.30 (m, 2H), 1.28 (t, J=7.2 Hz, 3H). HRMS (ES) M+H: 200.0746.

Step C
2-(Ethylsulfonyl)benzyl-3-(2,2-difluoro-2-(2-pyridyl-N-oxide)ethylamino)-6-chloropyrazin-2-one-1-acetamide trifluoroacetate The title compound was prepared according to the general EDC coupling procedure described in Example 33, Step E (with one equivalent Et$_3$N added to the reaction mixture) and was isolated as an off-white solid:

$^1$H NMR (CDCl$_3$): δ8.39 (t, J=4.0 Hz, 1H), 7.96 (d, J=8.4 Hz, 1H), 7.69–7.61 (m, 3H), 7.59–7.42 (m, 3H), 6.83 (t, J=6.4 Hz, 1H), 6.80 (s, 1H), 6.34 (m, 1H), 4.73 (s, 2H), 4.69 (d, J=6.4Hz, 2H), 4.62 (td, J=13.6,6.0 Hz, 2H), 3.18 (q, J=7.6 Hz, 2H), 1.31 (t, J=7.6 Hz, 3H). HRMS (ES) M+H: 542.1049

EXAMPLE 37

Preparation of 2-(2,2,2-Trifluoroethylthio)benzyl-3-(2,2-difluoro-2-(2-pyridyl-N-oxide)ethylamino)-6-chloropyrazin-2-one-1-acetamide trifluoroacetate

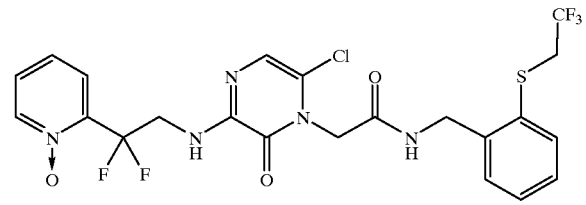

Step A
Methyl-2-(2,2,2-trifluoroethylthio)benzoate

Methylthiosalicylate (5.0 mL, 36 mmol) was added dropwise to a stirred suspension of NaH (60% oil dispersion, 1.43 g, 36 mmol) in dry DMF (30 ml,) at room temperature. The mixture was stirred in the dark under Ar for 30 min and was then cooled to 0° C. and treated with a solution of 1,1,1-trifluoro-2-iodoethane (3.0 mL, 30 mmol) in DMF (10 mL) via cannula. The reaction flask was covered with foil and was allowed to warm to room temperature while stirring overnight. Water was poured into the mixture which was then extracted with ether (3×150 mL). The combined ether extracts were washed with saturated aqueous Na$_2$CO$_3$ and brine, dried over MgSO$_4$ filtered and concentrated in vacuo. Silica gel chromatography (isocratic elution with 10% EtOAc-hexanes) afforded the title compound as a pale yellow oil:

$^1$H NMR (CDCl$_3$): δ7.94 (dd, J=6.4, 1.2 Hz, 1H), 7.51–7.45 (m, 2H), 7.31–7.27 (m, 1H), 3.94 (s, 3H), 3.58 (q, J=9.6 Hz, 2H).

Step B
2-(2,2,2-Trifluoroethylthio)benzyl alcohol

The title compound was prepared from methyl-2-(trifluoroethylthio)benzoate according to the procedure of Example 34, Step B and was isolated as a pale yellow oil:

$^1$H NMR (CDCl$_3$): δ7.56 (dd, J=6.0 Hz, 1.6 Hz, 1H), 7.46 (dd, J=5.6 Hz, 2.0 Hz, 1H), 7.37–7.29 (m, 2H), 4.87 (d, J=6.4 Hz, 2H), 3.49–3.42 (m, 2H), 2.02 (t, J=6.0 Hz, 1H).

Step C
2-Azidomethyl-(2,2,2-trifluoroethylthio)benzene

The title compound was prepared from 2-(2,2,2-trifluoroethylthio)benzyl alcohol according to the procedure of Example 34, Step C and was isolated as a pale yellow oil:

$^1$H NMR (CDCl$_3$): δ7.63–7.59 (m, 1H), 7.41–7.32 (m, 3H), 4.61 (s, 2H), 3.44 (q, J=9.6 Hz, 2H).

Step D
2-Aminomethyl-(2,2,2-trifluoroethylthio)benzene hydrochloride

The title compound was prepared from 2-azidomethyl-(2,2,2-trifluoroethylthio)benzene according to the procedure of Example 34, Step D, and was isolated as a white solid:

¹H NMR (CDCl₃ with 1 drop DMSO-d₆): δ7.81 (d, J=7.2 Hz, 1H), 7.64 (d, J=8.0 Hz, 1H), 7.42–7.37 (m, 2H), 4.37 (br s, 2H), 3.45 (q, J=9.6 Hz, 2H). MS (ES) M+H: 222.5.

Step E
2-(2,2,2-Trifluoroethylthio)benzyl-3-(2,2-difluoro-2-(2-pyridyl-N-oxide)ethylamino)-6-chloropyrazin-2-one-1-acetamide trifluoroacetate The title compound was prepared according to the general EDC coupling procedure described in Example 33, Step E (with one equivalent Et₃N added to the reaction mixture) and was isolated as a white solid:

¹H NMR (CDCl₃): δ8.28 (d, J=6.0 Hz, 1H), 7.64 (dd, J=5.2, 2.4 Hz, 1H), 7.54–7.51 (m, 1H), 7.39–7.26 (br m, 5H), 6.86 (s, 1H), 6.44 (t, J=6.0 Hz, 1H), s, 1H), 4.80 (s, 2H), 4.65–4.54 (m, 4H), 3.43 (q, J=9.6 Hz, 2H). HRMS (ES) M+H: 564.0889.

EXAMPLE 38

Preparation of (±)-2-(2,2,2-Trifluoroethylsulfoxy)benzyl-3-(2,2-difluoro-2-(2-pyridyl-N-oxide)ethylamino)- 6-chloropyrazin-2-one-1-acetamide trifluoroacetate

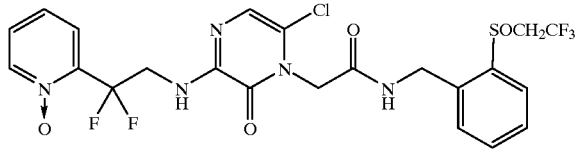

To a solution of 2-(2,2,2-trifluoroethylthio)benzyl-3-(2,2-difluoro-2-(2-pyridyl-N-oxide)ethylamino)-6-chloropyrazin-2-one-1-acetamide trifluoroacetate (29 mg, 0.052 mmol) in methanol and CH₂Cl₂ was added MCPBA (75%, 12 mg, 0.052 mmol). The mixture was stirred at room temperature for 1 h. The solvents were removed at reduced pressure and the residue was purified by reverse phase HPLC (gradient elution with 95:5 water/0.1% trifluoroacetic acid:acetonitrile/0.1% trifluoroacetic acid to 5:95 water/0.1% trifluoroacetic acid: acetonitrile/0.1% trifluoroacetic acid) to afford the title compound as a yellow solid which was dried oil a high vacuum line:

¹H NMR (DMSO-d₆): δ8.92 (t, J=6.0 Hz, 1H), 8.35 (d, J=6.8 Hz, 1H), 7.95–7.92 (m, 1H), 7.61–7.54 (br m, 3H), 7.44–7.20 (m, 2H), 6.80 (s, 1H), 4.73 (s, 2H), 4.50–4.32 (br m, 3H), 4.20–4.02 (br m, 3H). HRMS (ES) M+H: 580.0878.

EXAMPLE 39

Preparation of 2-(2,2,2-Trifluoroethylsulfonyl)benzyl-3-(2,2-difluoro-2-(2-pyridyl-N-oxide)ethylamino)- 6-chloropyrazin-2-one-1-acetamide trifluoroacetate

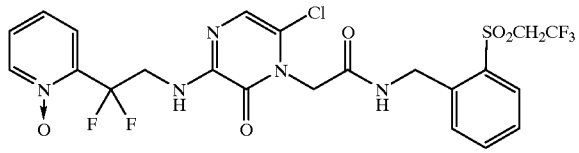

Step A
N-Boc-2-(2,2,2-Trifluoroethylthio)benzylamine

To a stirred solution of 2-aminomethyl-(2,2,2-trifluoroethylthio)benzene hydrochloride (500 mg, 1.94 mmol) in CH₂Cl₂ (20 mL) were added successively (BOC)₂O (465 mg, 2.13 mmol), DMAP (23.7 mg, 0.194 mmol) and Et₃N (0.27 mL, 1.94 mmol). The reaction mixture was stirred overnight at room temperature and was then diluted with EtOAc and washed successively with 10% aqueous citric acid, brine, and water. The organic layer was dried over MgSO₄ and concentrated at reduced pressure. Silica gel chromatography (isocratic elution with 20% EtOAc-hexanes) afforded the title compound as a colorless oil:

¹H NMR (CDCl₃): δ7.54–7.52 (m, 1H), 7.39 (d, J=7.6 Hz, 1H), 7.34–7.26 (m, 2H), 4.90 (br s, 1H), 4.51 (d, J=5.6 Hz, 2H), 3.46–3.38 (m, 2H), 1.45 (s, 9H).

Step B
N-Boc-₂-(2,2,2-Trifluoroethylsulfonyl)benzylamine

The title compound was prepared from N-Boc-2-(2,2,2-trifluoroethylthio)benzylamine according to the procedure described in Example 36, Step A and was isolated as a white solid:

¹H NMR (CDCl₃, 300 MHz): δ8.05 (d, J=8.1 Hz, 1H), 7.72–7.64 (m, 2H), 7.55–7.49 (m, 1H), 5.37 (br s, 1H), 4.61 (d, J=6.6 Hz, 2H), 4.16–4.06 (m, 2H), 1.43 (s, 9H).

Step C
2-(2,2,2-Trifluoroethylsulfonyl)benzylamine hydrochloride

To a stirred solution of N-Boc-2-(2,2,2-trifluoroethylsulfonyl)benzylamine (480 mg) in dioxane (4.0 mL) at room temperature was added excess 4.0 M HCl in dioxane. The mixture was stirred until no starting material remained by TLC and was then concentrated in vacuo to afford the title compound as an off-white solid:

¹H NMR (CD₃OD, 300 MHz) δ8.18 (d, J=7.8 Hz, 1H), 7.89–7.86 (m, 1H), 7.81–7.72 (m, 2H), 4.65 (q, J=9.3 Hz, 2H), 4.49 (s, 2H).

Step D
2-(2,2,2-Trifluoroethylsulfonyl)benzyl-3-(2,2-difluoro-2-(2-pyridyl-N-oxide)ethylamino)-6-chloropyrazin-2-one-1-acetamide trifluoroacetate The title compound was prepared according to the general EDC coupling procedure described in Example 33, Step E (with one equivalent Et₃N added to the reaction mixture) and was isolated as an off-white solid:

¹H NMR (CDCl₃): δ8.31 (d, J=6.4 Hz, 1H), 8.03 (d, J=8.0 Hz, 1H), 7.70–7.63 (m, 3H), 7.56–7.52 (m, 1H), 7.41–7.31 (m, 2H), 6.85 (s, 1H), 6.78 (m, 1H), 6.39 (m, 1H), 4.75 (s, 2H), 4.72 (d, J=6.4 Hz, 2H), 4.62 (td, J=13.6, 6.4 Hz, 2H), 406 (q, J=9.0 Hz, 2H). HRMS (FAB) M+Na: 618.0610.

EXAMPLE 40

Preparation of 3-(ethylthio)-2-pyridylmethyl-3-(2,2-difluoro-2-(2-pyridyl-N-oxide)ethylamino)-6-chloropyrazin-2-one-1-acetamide dihydrochloride

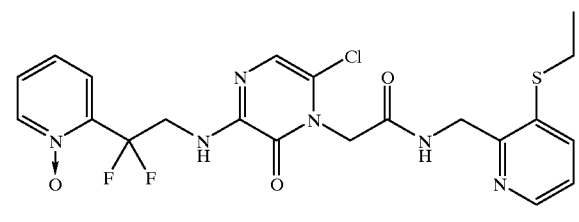

Step A
3-Bromopyridine-1-oxide

To a solution of 3-bromopyridine (1.52 mL, 15.8 mmol) in CH₂Cl₂ (35 mL) was added a solution of sodium bicarbonate (3.61 g, 42.9 mmol) in H₂O (43 mL). The biphasic mixture was cooled to 0° C. and treated with MCPBA (7.28 g, 31.6 mmol) in portions over 5 min. The mixture was stirred under N, overnight and was then transferred to a separatory funnel and the aqueous layer was determined to be basic (pH 8–9). The mixture was diluted with CHCl₃ and the layers were separated. The aqueous layer was further extracted with CHCl₃ (×3). The combined organic extracts were dried over MgSO₄ and concentrated in vacuo to afford a yellow oil. Silica gel chromatography (isocratic elution with 5% methanol-CHCl₃) afforded the title compound as a yellow oil:

¹H NMR (CDCl₃): δ8.38 (s, 1H), 8.17–8.15 (m, 1H), 7.43–7.41 (m, 1H), 7.19–7.15 (m, 1H).

Step B
3-Bromo-2-cyanopyridine

The preparation of the title compound has been described in the literature: Sakamoto, T.; Kaneda, S.; Nishimura, S.; Yamanaka, H. *Chem. Pharm. Bull.* 1985, 33 (2), 565–571.

Step C
2-Cyano-3-(ethylthio)pyridine

To a stirred suspension of sodium ethanethiolate (600 mg, 5.75 mmol) in dry THF (25 mL) was added 3-bromo-2-cyanopyridine (700 mg, 3.83 mmol). The reaction mixture was heated to reflux under N₂ for 3 h. The solvent was removed in vacuo and the resulting residue was taken Lip in CH₂Cl₂ (35 mL). The solution was filtered to remove precipitated sodium bromide and the filtrate was concentrated at reduced pressure to afford the title compound as a yellow oil:

¹H NMR (CDCl₃, 300 MHz): δ8.49 (dd, J=3.3, 1.2 Hz, 1H), 7.76 (d, J=1.2 Hz, 1H), 7.45–7.41 (m, 1H), 3.06 (q, J=7.2 Hz, 2H), 1.40–1.32 (m, 3H).

Step D
3-(ethylthio)pyridine-2-methylamine dihydrochloride

A mixture of 2-cyano-3-(ethylthio)pyridine (613 mg, 3.73 mmol) and concentrated HCl (0.93 mL, 11.2 mmol) in degassed ethanol (18 mL) was hydrogenated over 10% palladium on carbon (184 mg) at 60 psi overnight. Additional 10% palladium on carbon (180 mg) and conc. HCl (1 mL) were added to the reaction and hydrogenation was resumed at 61 psi overnight. The reaction mixture was filtered through Celite and washed with methanol. The filtrate was concentrated at reduced pressure to an orange solid which was taken up in methanol (12 mL). 10% Palladium on carbon (300 mg) and concentrated HCl (2.4 mL of a 6 M aqueous solution) were added and the mixture was hydrogenated at 57 psi for 3 days. The reaction mixture was again filtered through Celite, and the filter cake was washed with ethanol. The product was concentrated to a yellow-orange oil, which was taken up in methanol and treated with 1.0 M HCl in ether. The solvent was removed is vacuo to afford the title compound as an orange solid:

¹H NMR (CD₃OD): δ8.48 (m, 1H), 7.97 (dd, J=8.0 Hz, 12 Hz, 1H), 7.46 (dd, J=8.0, 1.2 Hz, 1H), 4.34 (s, 2H), 3.08 (q, J=7.2 Hz, 2H), 1.34 (t, J=7.2 Hz, 3H) MS (ES) M+H: 169.5

Step E
3-(ethylthio)-2-pyridylmethyl-3-(2,2-difluoro-2-(2-pyridyl-N-oxide)ethylamino)-6-chloropyrazin-2-one-1-acetamide dihydrochloride The title compound was prepared according to the general EDC coupling procedure as described in Example 33, Step E (with two equivalents Et₃N added to the reaction mixture). When the reaction was complete, the product was precipitated from the reaction mixture by addition of water. The solid residue was treated with 1.0 M HCl-ether and was collected by filtration to give the title compound as an off-white solid:

¹H NMR (CD₃OD, 300 MHz): δ8.56–8.52 (m, 2H), 8.44 (d, J=5.1 Hz, 1H), 7.95–7.90 (m, 1H), 7.78–7.75 (m, 1H), 7.65–7.62 (m, 2H), 6.81 (s, 1H), 5.25 (s, 2H), 4.68 (s, 2H), 4.58 (t, J=13.5 Hz, 2H), 3.25 (q, J=7.2 Hz, 2H), 1.41 (t, J=7.2 Hz, 3H). HRMS (ES) M+H: 511.1162.

EXAMPLE 41

Preparation of (+)-, (−)- and (±)3-(ethylsulfoxy)-2-pyridylmethyl-3-(2,2-difluoro-2-(2-pyridyl-N-oxide) ethylamino)-6-chloropyrazin-2-one-1-acetamide

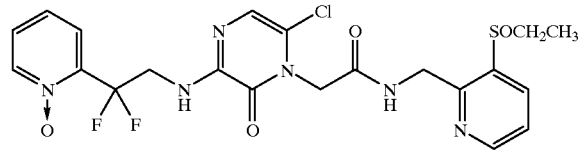

Step A
N-Phthalimido-3-(ethylthio)pyridyl-2-methylamine

The title compound was prepared from 3-(ethylthio) pyridyl-2-methylamine dihydrochloride (Example 40, Step D) according to the procedure of Example 33, Step A and was isolated as a purple solid:

¹H NMR (CDCl₃, 300 MHz): δ8.24–8.22 (m, 1H), 7.91–7.87 (m, 2H), 7.76–7.71 (m, 2H), 7.63 (dd, J=7.8, 1.5 Hz, 1H), 7.13–7.09 (m, 1H), 5.11 (s, 2H), 3.00 (q, J=7.2 Hz, 2H), 1.38 (t, J=7.2 Hz, 3H). MS (ES) M+H: 299.6

Step B
(±)-N-Phthalimido-3-(ethylsulfoxy)pyridyl-2-methylamine

The title compound was prepared from N-phthalimido-3-(ethylthio)pyridyl-2-methylamine according to the procedure of Example 35, Step B and was isolated after silica gel chromatography (isocratic elution with 70% EtOAc-hexanes) as a white solid:

¹H NMR (CDCl₃): δ8.54 (dd, J=4.8, 1.6 Hz, 1H), 8.26 (dd, J=7.6 Hz, 1.6 Hz, 1H), 7.91–7.88 (m, 2H), 7.78–7.74 (m, 2H), 7.43 7.40 (m, 1H), 5.16 (d, J$_{AB}$=16.0 Hz, 1H), 4.85 (d, J$_{AB}$=16.0 Hz, 1H), 3.25–3.16 (m, 1H), 3.00–2.91 (m, 1H), 1.35 (t, J=7.2 Hz, 3H).

Step C
(±)-3-(Ethylsulfoxy)pyridyl-2-methylamine

N-phthalimido-3-(ethylsulfoxy)pyridyl-2-methylamine was deprotected according to the procedure of Example 33, Step D. The crude product was purified by silica gel chromatography (isocratic elution with 9:0.9:0.1 CHCl₃:methanol:NH₄OH). The column fractions containing the product were concentrated at reduced pressure and the residue was dried on a high vacuum line to afford the title compound as a colorless oil:

¹H NMR (CDCl₃, 300 MHz): δ8.67–8.65 (m, 1H), 8.28–8.25 (m, 1H), 7.46–7.42 (m, 1H), 4.11 (d, J$_{AB}$=14.7 Hz, 1H), 3.92 (d, J$_{AB}$=14.7 Hz, 1H), 3.15–3.10 (br m, 1H), 2.87–2.76 (br m, 1H), 1.30–1.25 (m, 3H). MS (ES) M+H: 185.5

Step D
(+)-, (−)- and (±)3-(Ethylsulfoxy)-2-pyridylmethyl-3-(2,2-difluoro-2-(2-pyridyl-N-oxide)ethylamino)-6-chloropyrazin-2-one-1-acetamide The racemic title compound was prepared according to the general EDC coupling procedure as described in Example 33, Step E (with one equivalent Et₃N added to the reaction mixture) and was isolated as a yellow oil (trifluoroacetate salt):

¹H NMR (CDCl₃): δ8.73–8.70 (m, 1H), 8.47–8.45 (m, 2H), 8.06 (t, J=7.2 Hz, 1H), 7.78–7.63 (m, 2H), 7.54–7.47 (m, 2H), 6.83 (s, 1H), 6.42 (br s, 1H), 4.90 (br s, 2H), 4.68–4.39 (br m, 4H), 3.17–3.08 (br m, 1H), 2.94–2.81 (br m, 1H), 1.34 (t, J=7.2 Hz, 3H). MS (ES) M+H=527.7

The racemate was resolved into pure enantiomers under the following conditions:

Chiralcel OD column eluting with an 80:10:10 mixture of 0.1% diethylamine-hexanes:methanol:ethanol for 60 min, then a 30:30:40 mixture of 0.1% diethylamine-hexanes:methanol:ethanol until the isomers eluted separately. Removal of the solvents at reduced pressure afforded the enantiomers as oils (free bases):

Faster-moving enantiomer: $^1$H NMR (CDCl$_3$): δ9.40 (br s, 1H), 8.62 (dd, J=5.2, 1.6 Hz, 1H), 8.29–8.27 (m, 2H), 7.63 (dd, J=8.0, 2.4 Hz, 1H), 7.52–7.48 (m, 1H), 7.38–7.30 (br m, 2H), 6.90 (s, 1H), 6.39 (t, J=7.2 Hz, 1H), 4.89 (s, 2H), 4.69–4.49 (br m, 4H), 3.02–2.95 (br m, 1H), 2.80–2.71 (m, 1H), 1.36 (t, J=7.6 Hz, 3H). HRMS (ES) M+H: 527.1057.

Slower-moving enantiomer: $^1$H NMR (CDCl$_3$): δ9.40 (br s, 1H), 8.62 (dd, J=4.8, 1.2 Hz, 1H), 8.29–8.27 (m, 2H), 7.63 (dd, J=8.0, 2.0 Hz, 1H), 7.52–7.48 (m, 1H), 7.38–7.30 (br m, 2H), 6.90 (s, 1H), 6.39 (t, J=6.8 Hz, 1H), 4.89 (s, 2H), 4.69–4.49 (br m, 4H), 3.02–2.95 (br m, 1H), 2.80–2.71 (m, 1H), 1.34 (t, J=7.6 Hz H). MS (ES) M+H: 527.7

EXAMPLE 42

Preparation of 3-(ethylsulfonyl)-2-pyridylmethyl-3-(2,2-difluoro-2-(2-pyridyl-N-oxide)ethylamino)-6-chloropyrazin-2-one-1-acetamide trifluoroacetate

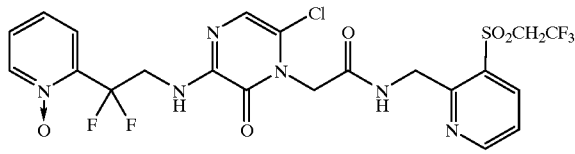

Step A
N-Phthalimido-3-(Ethylsulfonyl)pyridyl-2-methylamine

The title compound was prepared according to a procedure which was modified from that described in Giam, C. S.; Kikukawa, K.; Trujillo, D. A.; Org,. Prep. Proced. Int. 1981, 13 (2), 137–140 as follows: A solution of N-phthalimido-3-(ethylsulfoxy)pyridyl-2-methylamine (Example 41, Step B, 126 mg, 0.40 mmol) in a minimal amount of DCE was treated with 54 μL of a mixture of sodium tungstate (14 mg, 0.042 mmol) and acetic acid (1 drop) in water (4 mL). The mixture was heated to 65° C. and treated with 50% aqueous hydrogen peroxide (24 μL at the rate of 1 drop per 15 s). The mixture was refluxed for 24 h, then treated with an additional 27 μL of the tungstate mixture and refluxed for another 24 h. An additional 54 μL of the tungstate mixture was added and reflux was continued for 24 h. The solvent was removed in vacuo and the residue was taken up in water. The solution was treated with ammonium hydroxide and a small amount of sodium bisulfite to destroy residual hydrogen peroxide, and was then extracted with CHCl$_3$ (×2). The combined organic extracts were dried over Na$_2$SO$_4$ and concentrated at reduced pressure. The residue was purified by silica gel chromatography (70% EtOAc-hexanes) to give the title compound as a white foamy solid:

$^1$H NMR (CDCl$_3$, 300 MHz): δ8.64 (dd, J=4.8, 1.8 Hz, 1H), 8.27 (dd, J=8.1, 1.8 Hz, 1H), 7.92 –7.86 (m, 2H), 7.79 –7.73 (m, 2H), 7.41–7.37 (m, 1H), 5.40 (s, 2H), 3.48 (q, J=7.2 Hz, 2H), 1.40 (t, J=7.2 Hz, 3H).

Step B
3-(Ethylsulfonyl)pyridyl-2-methylamine dihydrochloride

A mixture of N-phthalimido-3-(ethylsulfonyl)pyridyl-2-methylamine (40 mg, 0. 12 mmol) and hydrazine hydrate (6.0 μL, 0. 12 mmol) in ethanol (2.5 mL) was heated to reflux overnight. The mixture was cooled to room temperature and treated with 12 M HCl (10 μL). The solvent was removed in vacuo and the residue was taken up in 1 M HCl and heated to 50° C. for 10 min. The solution was filtered and the residue rinsed with 1 M HCl. The filtrate was washed with CH$_2$Cl$_2$ (×2) and the aqueous layer was concentrated at reduced pressure. The residue was azeotroped with toluene to afford the title compound as a yellow oil (contaminated with phthalimide by-product):

$^1$H NMR (CDCl$_3$ with 1 drop DMSO-d$_6$, 300 MHz): δ8.87 (d, J=5.1 Hz, 1H), 8.32 (d, J=7.8 Hz, 1H), 7.63–7.57 (m, 1H), 4.66–4.64 (m, 2H), 3.42 (q, J=7.5 Hz, 2H), 1.32 (t, J=7.5 Hz, 3H). MS (ES) M+H=201.5. Phthalimide by-product appears in the $^1$H NMR at δ8.20–8.17 (m, 2H) and 7.82–7.79 (m, 2H).

Step D
3-(Ethylsulfonyl)-2-pyridylmethyl-3-(2,2-difluoro-2-(2-pyridyl-N-oxide)ethylamino)-6-chloropyrazin-2-one-1-acetamide trifluoroacetate The title compound was prepared according to the procedure of Example 33, Step E (with two equivalents Et$_3$N added to the reaction mixture) and was isolated as a pale yellow oil:

$^1$H NMR (CDCl$_3$): δ8.79 (dd, J=5.2, 1.6 Hz, 1H), 8.55 (d, J=6.0 Hz, 1H), 8.39 (dd, J=8.0, 1.6 Hz, 1H), 7.78–7.74 (m, 2H), 7.63–7.52 (m, 3H), 6.83 (s, 1H), 6.46 (br s, 1H), 4.97–4.96 (m, 2H), 4.88 (s, 2H), 4.62 (t, J=13.6 Hz, 2H), 3.39 (q, J=7.6 Hz, 2H), 1.32 (t, J=7.6 Hz, 3H). MS (ES) M+H: 543.7.

EXAMPLE 43

Preparation of 3-(2,2,2-Trifluoroethylthio)-2-pyridylmethyl-3(2,2-difluoro-2-(2-pyridyl-N-oxide)ethylamino)-6-chloropyrazin-2-one-1-acetamide dihydrochloride

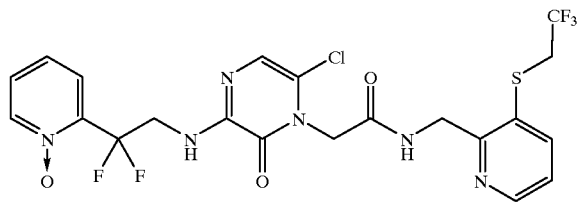

Step A
2-Cyano-3-(2,2,2-trifluoroethylthio)pyridine

A suspension of sodium hydride (60% oil dispersion, 180 mg, 4.52 mmol) in dry THF (17 mL) under N$_2$ was treated with trifluoroethanethiol (0.40 mL, 4.52 mmol) and the mixture was heated to 50° C. When gas evolution ceased (ca. 1 h), 3-bromo-2-cyanopyridine was added and the mixture was heated to reflux for 4 h. The solvent wag removed in vacuo and the residue was taken up in CH$_2$Cl$_2$ and filtered to remove precipitated sodium bromide. The filtrate was concentrated at reduced pressure to afford the title compound as an orange oil:

$^1$H NMR (CDCl$_3$): δ8.67 (dd, J=4.8, 1.6 Hz, 1H), 8.01 (dd, J=8.4, 1.6 Hz, 1H), 7.53–7.50 (m, 1H), 3.58 (q, J=9.2 Hz, 2H).

Step B
3-(2,2,2-Trifluoroethylthio)pyridyl-2-methylamine dihydrochloride

A mixture of 2-cyano-3-(2,2,2-trifluoroethylthio)pyridine (300 mg, 1.37 mmol) and 6 M HCl (1.2 mL) in degassed methanol (6.0 mL) was hydrogenated over 10% palladium on carbon (146 mg) at 55 psi for 24 h, then at 60 psi for 24 h. The reaction mixture was filtered through Celite and the filter cake was washed thoroughly with ethanol. Removal of the solvents at reduced pressure afforded the title compound as an orange oil:

$^1$H NMR (CD$_3$OD): δ8.60 (dd, J=4.8, 1.2 Hz, 1H), 8.13 (dd, J=7.6, 1.2 Hz, 1H), 7.48–7.45 (m, 1H), 4.48 (s, 2H), 3.81 (q, J=10 Hz, 2H). HRMS (ES) M+H: 223.0522.

Step C
3-(2,2,2-Trifluoroethylthio)-2-pyridylmethyl-3-(2,2-difluoro-2-(2-pyridyl-N-oxide)ethylamino)-6-chloropyrazin-2-one-1-acetamide dihydrochloride The title compound was prepared according to the general EDC coupling procedure described in Example 33, Step E (with two equivalents Et$_3$N added to the reaction mixture). After the described purification by reverse phase HPLC and removal of the solvents at reduced pressure, the dihydrochloride salt was prepared by treatment of the residue with 1 M HCl-ether and was isolated by filtration as an off-white solid:

$^1$H NMR (CD$_3$OD): δ8.75 (d, J=8.0 Hz, 1H), 8.68 (dd, J=5.6, 1.2 Hz, 1H), 8.42 (d, J=5.6 Hz, 1H), 7.97–7.93 (br m, 1H), 7.76 7.73 (m, 1H), 7.65–7.58 (br m, 2H), 6.79 (s, 1H), 4.96 (s, 2H), 4.79 (s, 2H), 4.57 (t, J=13.4 Hz, 2H), 4.07 (q, J=10 Hz, 2H). HRMS (ES) M+H: 565.0814.

EXAMPLE 44

Preparation of (±)-3-(2,2,2-Trifluoroethylsulfoxy)-2-pyridylmethyl-3-(2,2-difluoro-2-(2-pyridyl-N-oxide)ethylamino)-6-chloropyrazin-2-one-1-acetamide trifluoroacetate

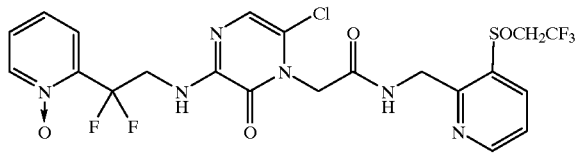

Step A
N-Boc-3-(2,2,2-trifluoroethylthio)pyridyl-2methylamine

The title compound was prepared from 3-(2,2,2-trifluoroethylthio)pyridyl-2-methylamine dihydrochloride (Example 43, Step B) according to the procedure described in Example 39, Step A and was purified by silica gel chromatography (isocratic elution with 30% EtOAc-hexanes) to afford a pale yellow oil:

$^1$H NMR (CDCl$_3$, 300 MHz): δ8.51 (dd, J=4.8, 1.5 Hz, 1H), 7.84 (d, J=7.8 Hz, 1H), 7.24–7.20 (m, 1H), 6.00 (br s, 1H), 4.64 (d, J=4.5 Hz, 2H), 3.41 (q, J=9.6 Hz, 2H), 1.46 (s, 9H).

Step B
(±)-N-Boc-3-(2,2,2-trifluoroethylsulfoxy)pyridyl-2-methylamine

The title compound was prepared from N-Boc-3-(2,2,2-trifluoroethylthio)pyridyl-2-methylamine according to the procedure of Example 35, Step B and was isolated as a white solid:

$^1$H NMR (CDCl$_3$): δ8.73 (dd, J=4.8, 1.6 Hz, 1H), 8.38 (dd, J=8.0, 1.6 Hz, 1H), 7.54–7.51 (m, 1H), 5.58 (br s, 1H), 4.49–4.37 (br m, 2H), 3.93 (br m, 1H), 3.55–3.45 (br m , 1H), 1.43 (s, 9H).

Step C
(±)-3-(2,2,2-trifluoroethylsulfoxy)pyridyl-2-methylamine dihydrochloride

The title compound was prepared from (±)-N-Boc-3-(2,2,2-trifluoroethylsulfoxy)pyridyl-2-methylamine according to the procedure of Example 39, Step C and was isolated as a yellow oil:

$^1$H NMR (CD$_3$OD): δ8.84 (dd, J=4.8, 1.6 Hz, 1H), 8.42 (dd, J=8.0, 1.6 Hz, 1H), 7.72 (dd, J=8.0, 4.8 Hz, 1H), 4.57–4.41 (br m, 2H), 4.12–4.07 (br m, 2H). MS (ES) M+H: 239.5.

Step D
(±)-3-(2,2,2-Trifluoroethylsulfoxy)-2-pyridylmethyl-3-(2,2-difluoro-2-(2-pyridyl-N-oxide)ethylamino)-6-chloropyrazin-2-one-1-acetamide trifluoroacetate The title compound was prepared according to the general EDC coupling procedure of Example 33, Step E (with two equivalents Et$_3$N added to the reaction mixture) and was isolated as a yellow oil:

$^1$H NMR (CDCl$_3$, 300 MHz): δ8.73 (d, J=4.8 Hz, 1H), 8.55–8.50 (m, 2H), 7.81 (br m, 1H), 7.76–7.71 (br m, 2H), 7.70–7.52 (m, 2H), 7.35 (br m, 1H), 6.82 (s, 1H), 4.82 (s, 2H), 4.65–4.46 (m, 4H), 4.12–4.04 (br m, 1H), 3.63 –3.51 (br m, H). MS (ES) M+H: 581.7.

EXAMPLE 45

Preparation of 3-(2,2,2-Trifluoroethylsulfonyl)-2-pyridyl-N-oxide-methyl-3-(2,2-difluoro-2-(2-pyridyl-N-oxide)ethylamino)-6-chloropyrazin-2-one-1-acetamide trifluoroacetate

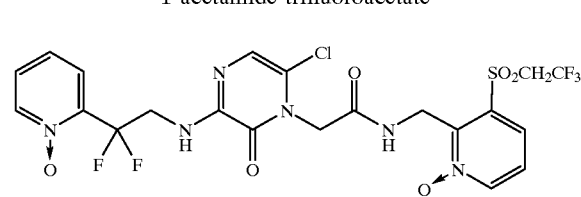

Step A
N-Boc-3-(2,2,2-trifluoroethylsulfonyl)pyridyl-N-oxide-2-methylamine

The title compound was prepared from N-Boc-3-(2,2,2-trifluoroethylthio)pyridyl-2-methylamine (Example 44, Step A) according to the procedure of Example 36, Step A (using excess MCPBA) and was isolated as a white solid:

$^1$H NMR (CDCl$_3$): δ8.46 (d, J=6.8 Hz, 1H), 7.98 (d, J=8.4 Hz, 1H), 7.52–7.45 (m, 1H), 6.43 (br s, 1H), 5.02–4.94 (br m, 4H), 1.39 (s, 9H). MS (ES) M+H: 371.6.

Step B
3-(2,2,2-trifluoroethylsulfonyl)pyridyl-N-oxide-2-methylamine dihydrochloride The title compound was prepared from N-Boc-3-(2,2,2-trifluoroethylsulfonyl)pyridyl-N-oxide-2-methylamine according to the procedure of Example 39, Step C and was isolated as a yellow oil:

$^1$H NMR (CD$_3$OD, 300 MHz): δ8.71 (d, J=6.6 Hz, 1H), 8.13 (d, J=8.4 Hz, 1H), 7.83 (dd, J=8.1, 6.6 Hz, 1H), 4.72 (s, 2H), 3.31–3.24 (m, 2H, overlaps with methanol residual peak). MS (ES) M+H: 271.5.

Step C
3-(2,2,2-Trifluoroethylsulfonyl)-2-pyridyl-N-oxide-methyl-3-(2,2-difluoro-2-(2-pyridyl-N-oxide)ethylamino)-6-chloropyrazin-2-one-1-acetamide trifluoroacetate The title compound was prepared according to the general EDC coupling procedure described in Example 33, Step E (with two equivalents Et$_3$N added to the reaction mixture) and was isolated as a yellow oil:

¹H NMR (DMSO-d₆): δ8.94 (m, 1H), 8.71 (d, J=6.0 Hz, 1H), 8.34 (d, J=6.0 Hz, 1 H), 7.87 (d, J=7.2 Hz, 1H), 7.74–7.70 (m, 1H), 7.59–7.50 (m, 3H), 7.40–7.36 (br m, 1H), 6.75 (s, 1H), 5.24 (q, J=10.4 Hz, 2H), 4.89 (m, 2H), 4.74 (s, 2H), 4.40 (m, 2H). MS (ES) M+H: 613.6.

EXAMPLE 46

Preparation of (+)- and (−)-2-(Methylsulfoxy) benzyl-3-(2,2-difluoro-2-(2-pyridyl-N-oxide) ethylamino)-6-chloropyrazin-2-one-1-acetamide trifluoroacetate

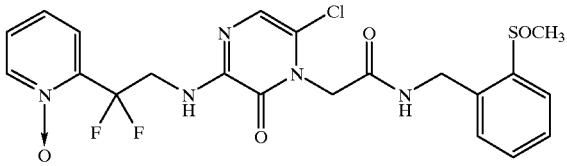

Step A
2-(Methylthio)benzyltrifluoroacetamide

The crude title compound was prepared from commercially available 2-(methylthio)benzylamine according to the procedure of Example 35, Step A and was purified by silica gel chromatography (isocratic elution with 40% EtOAc-hexanes) to afford a white solid:

¹H NMR (CDCl3, 300 MHz): d 7.37–7.15 (br m, 4H), 6.77 (br s, 1H), 4.61 (d, J=6.0 Hz, 2H), 2.51 (s, 3H).

Step B
(+)- and (−)-2-(Methylsulfoxy)benzyltrifluoroacetamide 2-(Methylthio)benzyltrifluoroacetamide was oxidized according to the procedure of Example 35, Step B. The initial crude mixture of enantiomers was separated from the 2-(methylsulfonyl)benzyltrifluoroacetamide by-product by silica gel chromatography (gradient elution with 100% EtOAc to 10% MeOH—CHCl3). The sulfoxide enantiomers were separated on a Chiralpak AD column under the following conditions: 95:5 to 85:15 hexanes/0.1% diethylamine:ethanol over 60 min, followed by 80: hexanes/0.1% diethylamine:ethanol for 1 min, followed by 65:35 hexanes/0.1% diethylamine:ethanol until the separated isomers eluted. The fractions were concentrated to yield the two isomers as white solids:

Faster moving enantiomer: ¹H NMR (300 MHz, CDCl₃): δ7.90 (br s, 1H), 7.62–7.59 (m, 1H), 7.55–7.46 (br m, 3H), 4.83–4.70 (br m, 2H), 2.87 (s, 3H).

Slower moving enantiomer: ¹H NMR (300 MHz, CDCl₃): δ7.89 (br s, 1H), 7.62–7.60 (m, 1H), 7.59–7.46 (br m, 3H), 4.84–4.70 (br m, 2H), 2.87 (s, 3H).

Step C
(+)- and (−)-2-(Methylsulfoxy)benzylamine

Potassium carbonate (120 mg, 0.871 mmol) was added to a degassed solution of the faster moving enantiomer of 2-(methylsulfoxy) benzyltrifluoroacetamide in methanol (9.7 mL) and water (0.65 mL) and the mixture was heated at 65° C. overnight under Ar atmosphere. Additional potassium carbonate (100 mg) was added and heating was resumed at 70° C. overnight. Silica gel was added to the crude mixture and the solvent was removed at reduced pressure. The residual powder was loaded onto a pre-packed silica gel column and the product was eluted with 9:0.9:0.1 CHCl3-MeOH—NH4OH. The product fractions were combined, concentrated at reduced pressure and dried on a high vacuum line to afford the title compound as a pale yellow oil:

¹H NMR (CDCl₃): δ8.05 (dd, J=7.6, 1.2 Hz, 1H), 7.54–7.50 (m, 1H), 7.48–7.44 (m, 1H), 7.38 (d, J=7.6 Hz, 1H), 4.03–3.93 (m, 2H), 2.84 (s, 3H).

The slower moving enantiomer of 2-(methylsulfoxy) benzyltrifluoroacetamide was deprotected in the same manner to afford the title compound as a pale yellow oil:

¹H NMR (300 MHz, CDCl₃): δ8.05 (dd, J=7.5, 1.5 Hz, 1H), 7.54–7.50 (m, 1H), 7.49–7.44 (m, 1H), 7.39–7.36 (m, 1H), 4.04–3.92 (m, 2H), 2.84 (s, 3H).

Step D
(+)- and (−)-2-(Methylsulfoxy)benzyl-3-(2,2-difluoro-2-(2-pyridyl-N-oxide)ethylamino)-6-chloropyrazin-2-one-1-acetamide trifluoroacetate The faster-moving enantiomer (on a Chiralpak AD column eluting with 30:70 0.1%TFA-hexanes:ethanol) of the title compound was prepared according to the general EDC coupling procedure described in Example 33, Step E using the pure enantiomer of 2-(methylsulfoxy)benzylamine which came from the faster-moving isomer of 2-(methylsulfoxy)benzyltrifluoroacetamide. The crude coupling product was purified by reverse phase HPLC (gradient elution from 95:5 water/0.1% trifluoroacetic acid:acetonitrile/0.1% trifluoroacetic acid to 5:95 water/0.1% trifluoroacetic acid:acetonitrile/0.1% trifluoroacetic acid) and the fractions containing product were concentrated and dried on a high vacuum line to afford one pure enantiomer as a white solid:

¹H NMR (300 MHz, DMSO-d₆): δ8.88 (t, J=5.6 Hz, 1H), 8.36 (d, J=6.0 Hz, 1H), 7.89–7.86 (m, 1H), 7.62–7.36 (br m, 7H), 6.80 (s, 1H), 4.73 (s, 2H), 4.52–4.29 (br m, 4H), 2.71 (s, 3H). MS (ES) M+H: 512.1.

The slower-moving enantiomer of the title compound was prepared and purified in similar fashion and was isolated as a white solid:

¹H NMR (300 MHz, DMSO-d₆): δ8.88 (t, J=5.6 Hz, 1H), 8.36 (d, J=6.3 Hz, 1H), 7.89–7.86 (m, 1H), 7.62–7.50 (br m, 5H), 7.41–7.36 (br m, 2H), 6.80 (s, 1H), 4.73 (s, 2H), 4.52–4.29 (br m, 4H), 2.71 (s, 3H). MS (ES) M+H: 512.1.

EXAMPLE 47

Preparation of 6-chloro-3-{[2,2-difluoro-2-(1-oxidopyridin-2-yl)ethyl]amino}-1-(2{-[(1S)-2-hydroxy-1-phenylethyl]amino}-2-oxoethyl)-2-oxo-1, 2-dihydropyrazin-4-ium chloride

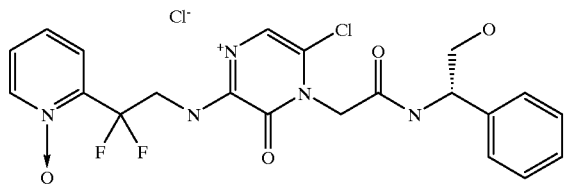

The title compound was prepared from (S) phenylglycinol and acid 16 according to the procedure in Example 1, step R. ¹H NMR (400 mHz, CD₃OD) δ8.45 (dd, 1H, J=2.1 and 7.13 Hz); 7.79 (m, 1H); 7.65 (m, 2H); 7.33–7.25 (m, 5H); 6.82 (s, 1H); 5.0 (m, 3H); 4.59 (t, 2H, J=13.5 Hz); 3.78 (dd, 1H, J=5.2 and 11.3 Hz); 3.72 (dd, 1H, J=7.5 and 11.3 Hz) Mass Spectrum (electrospray) M+H=480.1

EXAMPLE 48

Preparation of 6-chloro-1-(2-{[(1R)-1-(3-chlorophenyl)ethyl]amino}-2-oxoethyl)-3-{[2,2-difluoro-2-(1-oxidopyridin-2-yl)ethyl]amino}-2-oxo-1,2-dihydropyrazin-4-ium chloride

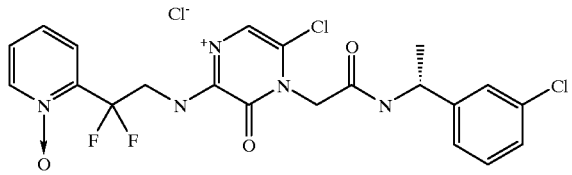

The title compound was prepared from (1R)1-(3-chlorophenyl)ethylamine (Pickard, Simeon T.; Smith, Howard E. *J. Am. Chem. Soc.* 1990, 112, 5741–7.) phenylglycinol and acid 16 according to the procedure in Example 1, step R. $^1$H NMR $^1$H NMR (400 mHz, CD$_3$OD) δ8.54 (dd, 1H, J=1.6 and 6.95 Hz); 7.90 (m, 1H); 7.75 (m, 2H); 7.3 (m, 4H); 6.98 (s, 1H); 4.9 (m, 3H); 4.5 (t, 2H, J=13.8 Hz); 1.47, (d, 3H, J=7.5 Hz). Mass Spectrum (electrospray) M+H= 498.1

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

In Vitro Assay For Determining Proteinase Inhibition

Assays of human α-thrombin and human trypsin were performed by the methods substantially as described in Thrombosis Research, Issue No. 70, page 173 (1993) by S. D. Lewis et al.

The assays were carried out at 25° C. in 0.05 M TRIS buffer pH 7.4, 0.15 M NaCl, 0. 1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human (α-thrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$ M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in the following equation.

$$V_o/V_i=1+[I]/K_i$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 49

Tablet Preparation

Tablets containing 25.0, 50.0, and 100.0 mg., respectively, of the following active compounds are prepared as illustrated below (compositions A–C). Active I is compound 3-Fluoro-2-pyridylmethyl 3-(2,2-difluoro-2-(2-pyridyl-N -oxide)ethylamino)-6-chloropyrazin-2-one-1-acetamide (Example 1).

|           | Amount-(mg) | | |
| Component | A | B | C |
| --- | --- | --- | --- |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 50

Tablet Preparation

Exemplary compositions of compound 3-Fluoro-2-pyridylmethyl 3-(2,2-difluoro-2-(2-pyridyl-N-oxide)ethylamino)-6-chloropyrazin-2-one-1-acetamide

| Component | 0.25 mg | 2 mg | 10 mg | 50 mg |
| --- | --- | --- | --- | --- |
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation Via Direct Compression

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE 51

Intravenous Formulations

Intravenous formulations of compound 3-Fluoro-2-pyridylmethyl 3-(2,2-difluoro-2-(2-pyridyl-N-oxide)ethylamino)-6-chloropyrazin-2-one-1-acetamide (Active I) were prepared according to general intravenous formulation procedures.

| Component | Estimated range |
| --- | --- |
| Active I | 0.12–0.61 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Exemplary compositions A–C are as follows:

| Component | A | B | C |
| --- | --- | --- | --- |
| Active I | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg freebase
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound having the formula:

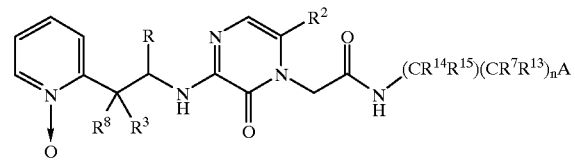

wherein
A is

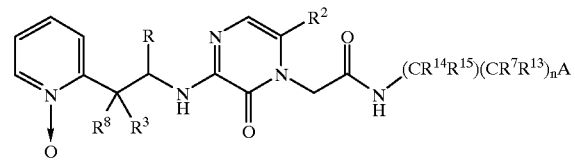

n=0–1;
R is
  hydrogen,
$R^2$ is
  hydrogen,
  $C_{1-4}$ alkyl,

CF₃,
halogen,
cyano, or
cyclo C₃₋₇ alkyl;

$R^3$, $R^7$, $R^8$, and $R^{13}$ are independently chosen from
hydrogen,
halogen,
$C_{1-4}$ alkyl;

$R^{14}$ and $R^{15}$ are independently chosen from
hydrogen,
$C_{1-2}$ alkyl, and
$C_{1-2}$ alkyl substituted with $OR^{16}$ or $COOR^{16}$, wherein $R^{16}$ is hydrogen or $C_{1-4}$ alkyl; and $R^4$, $R^5$ and $R^6$ are independently chosen from
hydrogen,
halogen,
hydroxy,
$C_{1-4}$ alkyl,
$C_{1-4}$ alkoxy,
cyano,
CF₃O,
CHF₂O,
CF₃CH₂O,
$SR^{10}$,
$SOR^{10}$,
$SO_2R^{10}$,
$OR^{11}$,
$SR^{11}$,
$NHR^{11}$
wherein
$R^{10}$ is $C_{1-4}$ alkyl unsubstituted or substituted with C(CH₃)₂NH₂, C(CH₃)₂OH, C(CH₃)₂NHCOCF₃, or CF₃, and
$R^{11}$ is phenyl unsubstituted or substituted with one or more of $C_{1-4}$ alkyl, $C_{1-4}$ alkoxy, halogen, hydroxy, COOH, CONH₂, CH₂OH, or $CO_2R^{12}$, wherein $R^{12}$ is $C_{1-4}$ alkyl.

2. A compound of claim 1, or pharmaceutically acceptable salt thereof, wherein A is

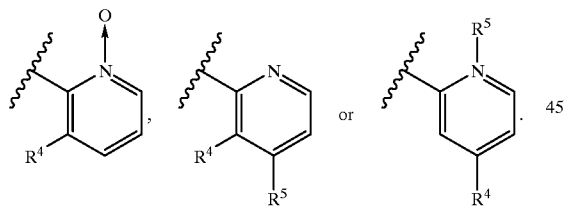

3. A compound of claim 2, or pharmaceutically acceptable salt thereof, wherein $R^2$ is Cl, CH₃ or CN; $R^4$ and $R^5$ are independently selected from the group consisting of hydrogen, $C_{1-4}$ alkyl, SMe, SOMe, SO₂Me, CN, OCH₂CF₃, OCH₃SCH₂C(CH₃)₂NH₂, OCF₃, SCH₂CH₃, SOCH₂CH₃, SO₂CH₂CH₃, SCH₂CF₃, SOCH₂CF₃, SO₂CH₂CF₃, and halogen, $R^7$ is hydrogen or fluoro; and $R^{13}$ is hydrogen or fluoro.

4. A compound of claim 3, or pharmaceutically acceptable salt thereof, wherein $R^4$ and $R^5$ are independently selected from the group consisting of hydrogen, CH₃, Cl, F, SMe, SOMe, SO₂Me, CN, OCH₂CF₃, OCH₃, SCH₂C(CH₃)₂NH₂, OCF₃, SCH₂CH₃, SOCH₂CH₃, SO₂CH₂CH₃, SCH₂CF₃, SOCH₂CF₃, and SO₂CH₂CF₃.

5. A compound of claim 4, or pharmaceutically acceptable salt thereof, wherein A is selected from the group consisting of

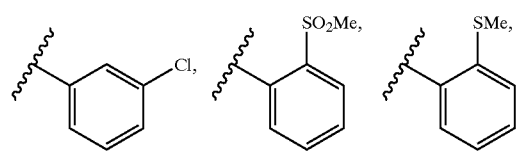

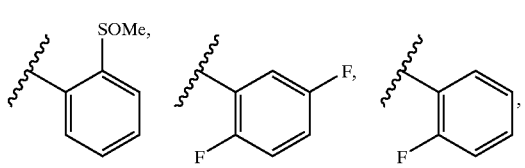

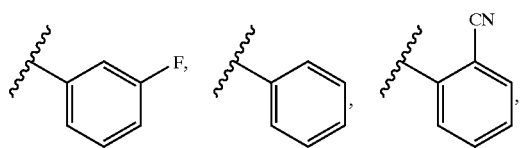

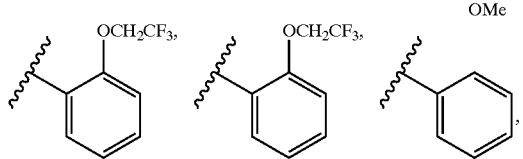

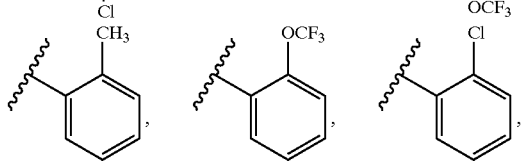

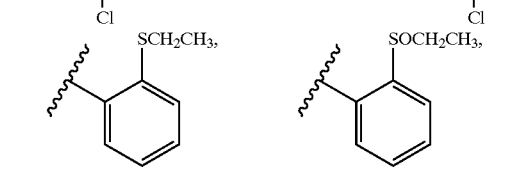

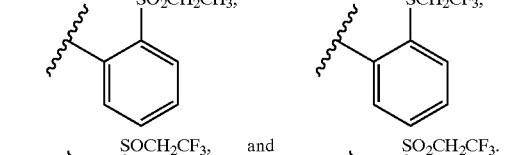

6. A compound of claim 4, or pharmaceutically acceptable salt thereof, wherein A is selected from the group consisting of

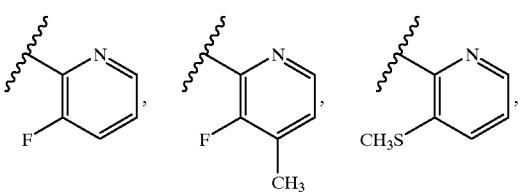

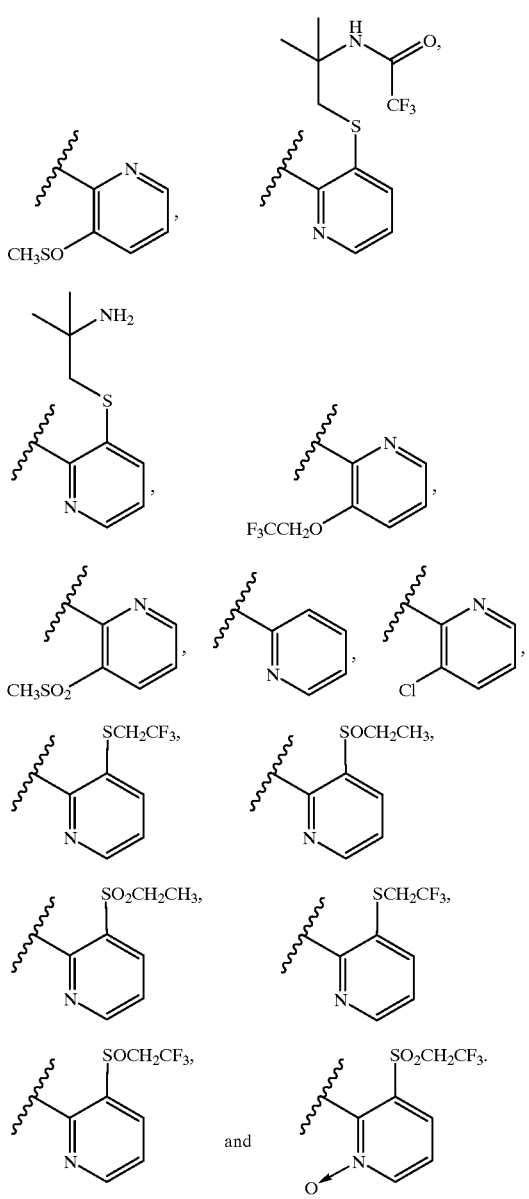
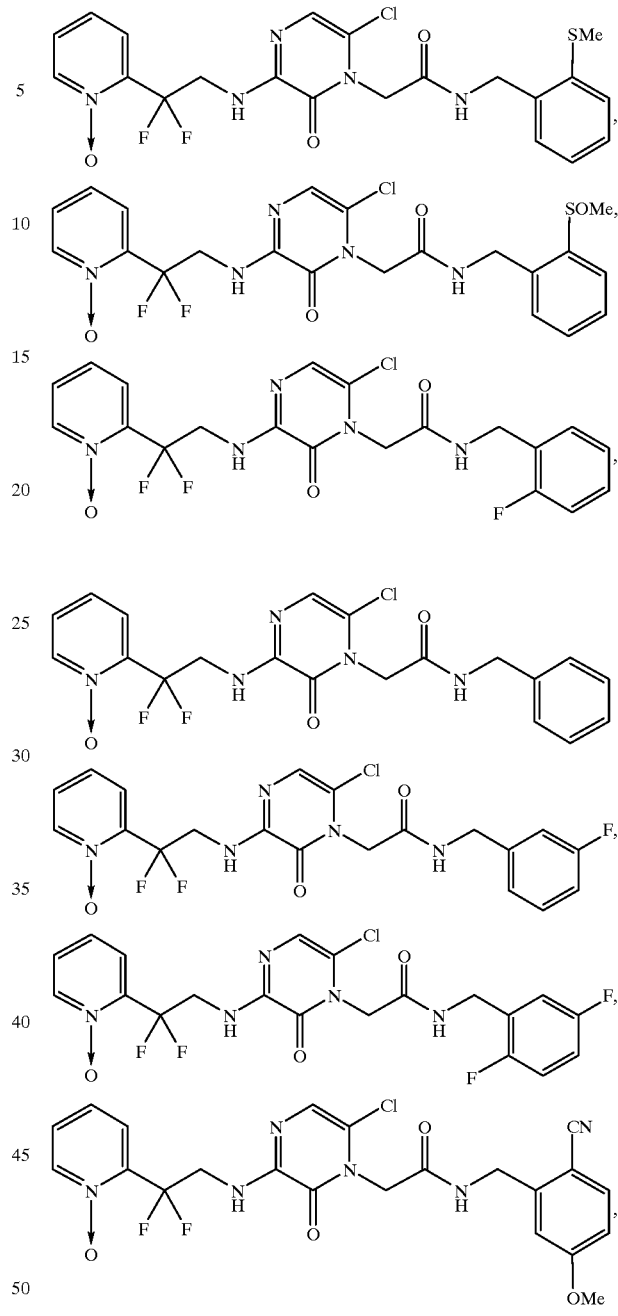
7. A compound of claim 5, or pharmaceutically acceptable salt thereof, selected from the group consisting of
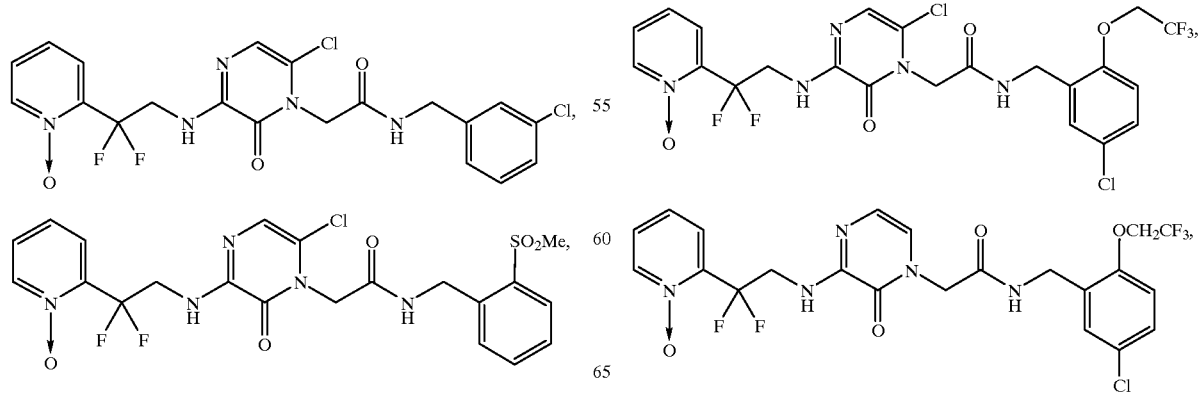

-continued

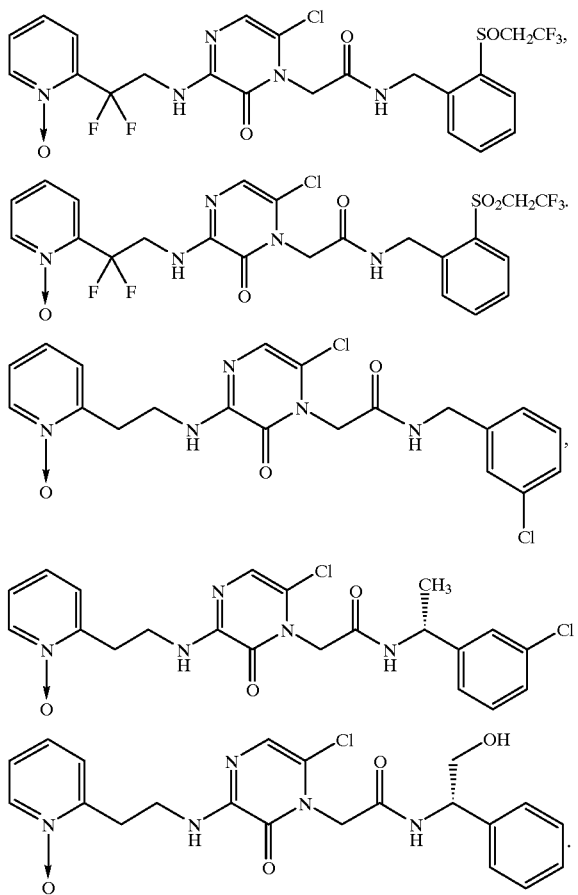
8. A compound of claim 6, or pharmaceutically acceptable salt thereof, selected from the group consisting of
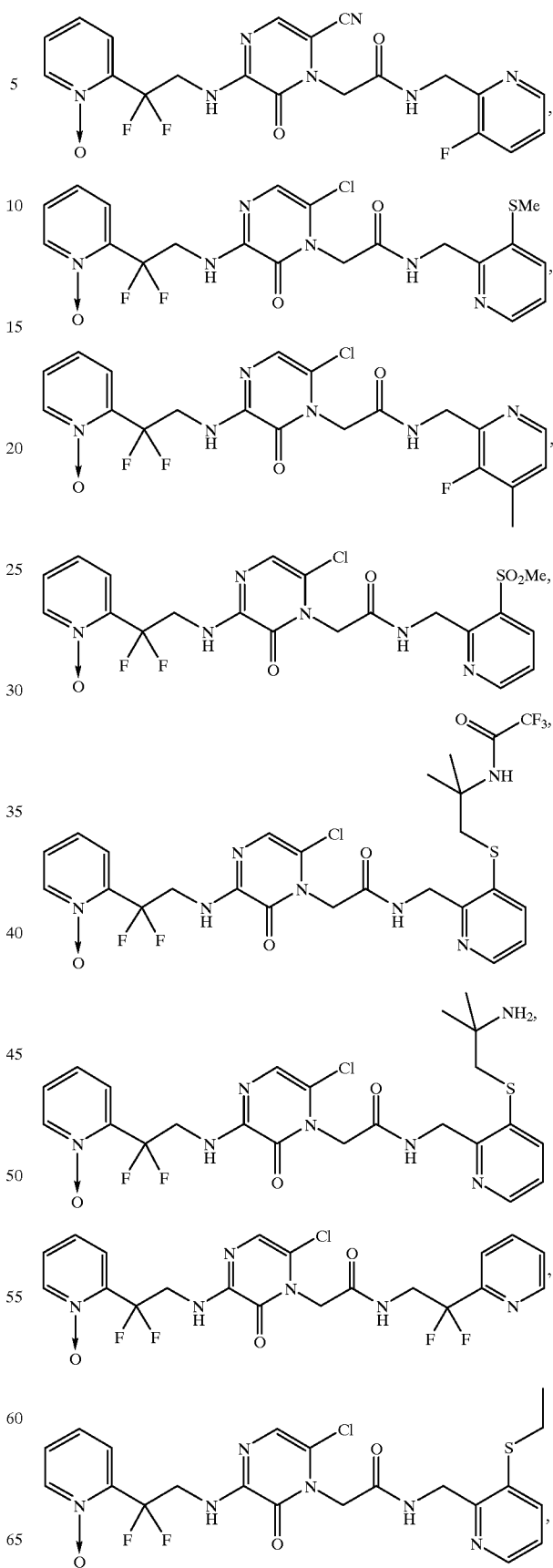

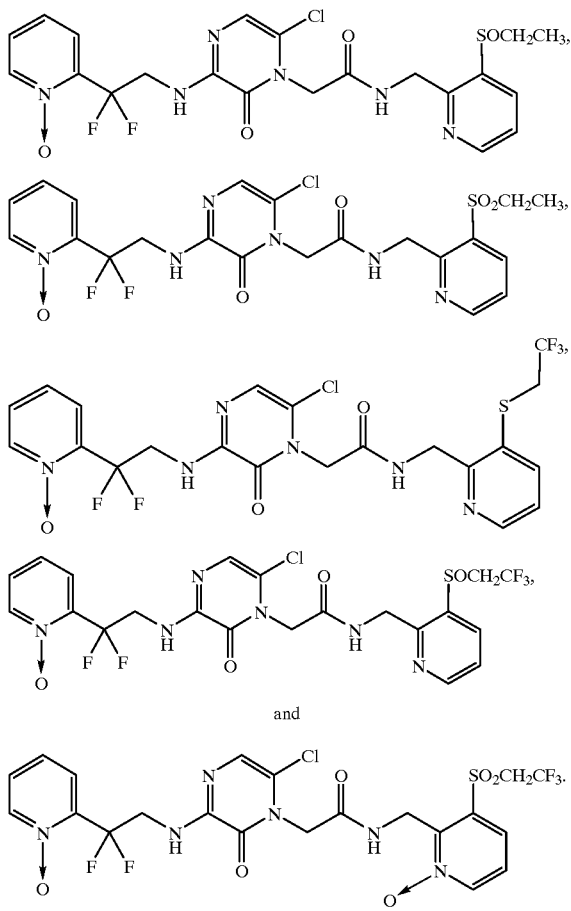

9. A compound of claim 7, or pharmaceutically acceptable salt thereof, selected from the group consisting of

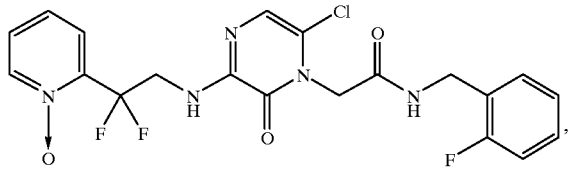

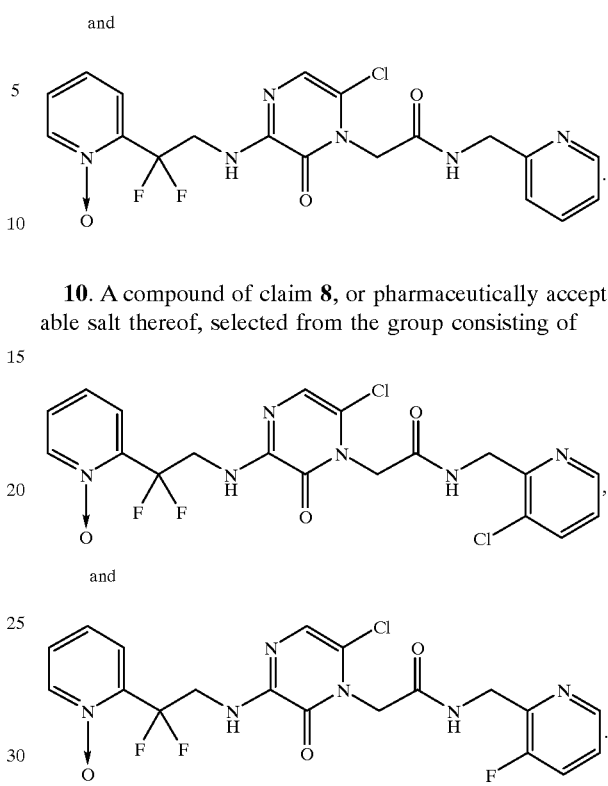

10. A compound of claim 8, or pharmaceutically acceptable salt thereof, selected from the group consisting of 11. A composition for inhibiting thrombus formation in blood comprising a compound of claim 1 and a pharmaceutically acceptable carrier.

12. A method for inhibiting thrombin in blood comprising adding to the blood a composition of claim 11.

13. A method for inhibiting formation of blood platelet aggregates in blood comprising adding to the blood a composition of claim 11.

14. A method for inhibiting thrombus formation in blood comprising adding to the blood a composition of claim 11.

* * * * *